(12) United States Patent
Nakamura et al.

(10) Patent No.: US 11,626,618 B2
(45) Date of Patent: Apr. 11, 2023

(54) ELECTROLYTE FOR LITHIUM ION SECONDARY BATTERY, LITHIUM ION SECONDARY BATTERY, AND MODULE

(71) Applicant: DAIKIN INDUSTRIES, LTD., Osaka (JP)

(72) Inventors: Hisako Nakamura, Osaka (JP); Shigeaki Yamazaki, Osaka (JP); Kenzou Takahashi, Osaka (JP); Yuuki Suzuki, Osaka (JP); Akiyoshi Yamauchi, Osaka (JP); Kotaro Hayashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 340 days.

(21) Appl. No.: 16/641,396

(22) PCT Filed: Jul. 12, 2018

(86) PCT No.: PCT/JP2018/026382
§ 371 (c)(1),
(2) Date: Feb. 24, 2020

(87) PCT Pub. No.: WO2019/039130
PCT Pub. Date: Feb. 28, 2019

(65) Prior Publication Data
US 2020/0203769 A1    Jun. 25, 2020

(30) Foreign Application Priority Data
Aug. 25, 2017 (JP) ............... JP2017-162741

(51) Int. Cl.
*H01M 10/0567* (2010.01)
*C07D 233/58* (2006.01)
*C07F 5/04* (2006.01)
*H01M 10/0525* (2010.01)

(52) U.S. Cl.
CPC ...... *H01M 10/0567* (2013.01); *C07D 233/58* (2013.01); *C07F 5/04* (2013.01); *H01M 10/0525* (2013.01); H01M 2300/0025 (2013.01)

(58) Field of Classification Search
None
See application file for complete search history.

(56) References Cited

U.S. PATENT DOCUMENTS

| | | |
|---|---|---|
| 2002/0015883 A1 | 2/2002 | Hilariius et al. |
| 2012/0058401 A1 | 3/2012 | Ihara et al. |
| 2017/0077557 A1* | 3/2017 | Zheng ............ H01M 10/0525 |

FOREIGN PATENT DOCUMENTS

| | | |
|---|---|---|
| CN | 103094610 A | 5/2013 |
| CN | 105826596 A | 8/2016 |
| JP | 1-194313 A | 8/1989 |
| JP | 2008-218487 A | 9/2008 |
| JP | 2012-54156 A | 3/2012 |
| KR | 10-2002-0017927 A | 3/2002 |

OTHER PUBLICATIONS

Larush et al., On the thermal behavior of model Li—LixCoO2 systems containing ionic liquids in standard electrolyte solutions, 2009, J Power Sources, 189, 217-223 (Year: 2009).*
L Larush et al., "On the thermal behavior of model Li—Li$_x$CoO$_2$ systems containing ionic liquids in standard electrolyte solutions", Journal of Power Sources, 2009, pp. 217-223, vol. 189.
International Search Report for PCT/JP2018/026382 dated Sep. 18, 2018 [PCT/ISA/210].
Extended European Search Report dated Mar. 30, 2021, issued by the European Patent Office in application No. 18848321.8.
International Preliminary Report on Patentability with a Translation of Written Opinion in International Application No. PCT/JP2018/026382, dated Feb. 25, 2020.

* cited by examiner

*Primary Examiner* — Daniel S Gatewood
(74) *Attorney, Agent, or Firm* — Sughrue Mion, PLLC

(57) ABSTRACT

An electrolyte solution for a lithium ion secondary battery, containing a compound (1) represented by the following formula (1):

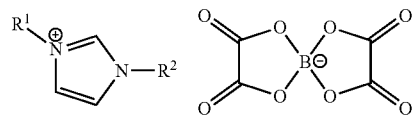

wherein $R^1$ and $R^2$ are each independently a C1-C4 alkyl group optionally containing an ether bond, and wherein chloride ion is present at a concentration of $1.0 \times 10^{-6}$ to $1.0 \times 10^3$ ppm. Also disclosed is an electrolyte solution for a lithium ion secondary battery, containing an imidazolium cation (1-1) represented by the following formula (1-1), a bis(oxalato)borate anion, and a hexafluorophosphate anion, the formula (1-1) being:

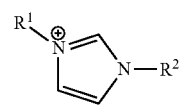

wherein $R^1$ and $R^2$ are each independently a C1-C4 alkyl group optionally containing an ether bond, and wherein chloride ion is present at a concentration of $1.0 \times 10^{-6}$ to $1.0 \times 10^3$ ppm.

11 Claims, No Drawings

ELECTROLYTE FOR LITHIUM ION SECONDARY BATTERY, LITHIUM ION SECONDARY BATTERY, AND MODULE

CROSS REFERENCE TO RELATED APPLICATIONS

This application is a National Stage of International Application No. PCT/JP2018/026382 filed Jul. 12, 2018, claiming priority based on Japanese Patent Application No. 2017-162741 filed Aug. 25, 2017.

TECHNICAL FIELD

The invention relates to electrolyte solutions for a lithium ion secondary battery, lithium ion secondary batteries, and modules.

BACKGROUND ART

Current electric appliances demonstrate a tendency to have a reduced weight and a smaller size, which leads to development of electrochemical devices such as lithium-ion secondary batteries having a high energy density. Further, electrochemical devices such as lithium-ion secondary batteries are desired to have improved characteristics as they are applied to more various fields. Improvement in battery characteristics will become more and more important particularly when lithium-ion secondary batteries are put in use for automobiles.

Capacitors have been also studied in order to improve their characteristics. For example, Patent Literature 1 discloses an electrolyte solution for an electrolytic capacitor, containing a quarternary ammonium salt or a quarternary phosphonium salt of a specific boron-containing anion as a solute.

Patent Literature 2 discloses an electrolyte solution for an electrochemical capacitor, containing an amidinium salt that contains a specific boron-containing anion and an imidazolium cation substituted with an alkyl group at the position 2.

CITATION LIST

Patent Literature

Patent Literature 1: JP H01-194313 A
Patent Literature 2: JP 2008-218487 A

SUMMARY OF INVENTION

Technical Problem

Lithium ion secondary batteries are required to have low resistance and excellent cycle characteristics, which requires electrolyte solutions capable of improving these characteristics.

The invention has been made under the current situation in the art and aims to provide an electrolyte solution capable of providing a lithium ion secondary battery having low resistance and excellent cycle characteristics, and a lithium ion secondary battery containing the electrolyte solution.

Solution to Problem

The invention relates to an electrolyte solution for a lithium ion secondary battery, including a compound (1) represented by the following formula (1):

[Chem. 1]

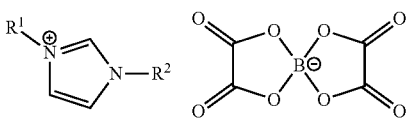

wherein $R^1$ and $R^2$ are each independently a C1-C4 alkyl group optionally containing an ether bond (hereinafter, also referred to as a first electrolyte solution of the invention).

At least one of $R^1$ or $R^2$ in the formula (1) is preferably a methyl group.

The compound (1) is preferably at least one selected from the group consisting of a compound (1-a) represented by the following formula (1-a):

[Chem. 2]

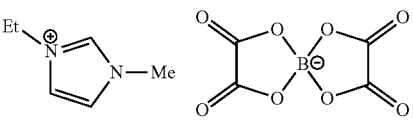

and a compound (1-b) represented by the following formula (1-b):

[Chem. 3]

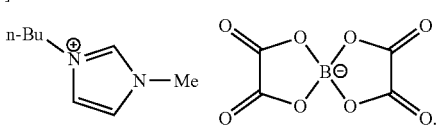

The invention also relates to an electrolyte solution for a lithium ion secondary battery, containing an imidazolium cation (1-1) represented by the following formula (1-1), a bis(oxalato)borate anion, and a hexafluorophosphate anion, the formula (1-1) being

[Chem. 4]

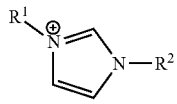

wherein $R^1$ and $R^2$ are each independently a C1-C4 alkyl group optionally containing an ether bond (hereinafter, also referred to as a second electrolyte solution of the invention).

At least one of $R^1$ or $R^2$ in the formula (1-1) is preferably a methyl group.

The imidazolium cation (1-1) is preferably at least one selected from the group consisting of an imidazolium cation (1-1a) represented by

[Chem. 5]

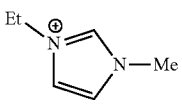

and an imidazolium cation (1-1b) represented by

[Chem. 6]

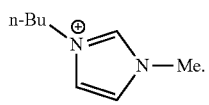

The second electrolyte solution preferably contains the imidazolium cation (1-1) at a concentration of $1.0 \times 10^{-5}$ to 1.0 mol/L, the bis(oxalato)borate anion at a concentration of $1.0 \times 10^{-5}$ to 1.0 mol/L, and the hexafluorophosphate anion at a concentration of 0.01 to 1.5 mol/L.

Preferably, the first and second electrolyte solutions of the invention each further contain a chloride ion.

Each of the first and second electrolyte solutions of the invention preferably contains the chloride ion at a concentration of $1.0 \times 10^{-6}$ to $1.0 \times 10^{3}$ ppm.

The invention also relates to a lithium ion secondary battery containing the first or second electrolyte solution of the invention.

The invention also relates to a module including the lithium ion secondary battery.

Advantageous Effects of Invention

The electrolyte solution of the invention can provide a lithium ion secondary battery having low resistance and excellent cycle characteristics.

The lithium ion secondary battery of the invention has low resistance and excellent cycle characteristics.

DESCRIPTION OF EMBODIMENTS

The invention will be specifically described hereinbelow.

The first electrolyte solution of the invention contains a compound (1) represented by the following formula (1).

[Chem. 7]

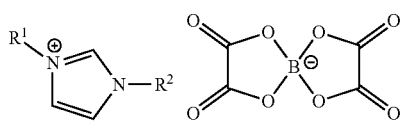

The presence of the compound (1) allows the first electrolyte solution of the invention to provide a lithium ion secondary battery having low resistance and excellent cycle characteristics.

In the formula (1), $R^1$ and $R^2$ are each independently a C1-C4 alkyl group optionally containing an ether bond. Examples of the alkyl group include a methyl group (Me), an ethyl group (Et), a propyl group (Pr), and a butyl group (Bu). At least one selected from $R^1$ and $R^2$ is preferably a methyl group. Preferably, one of $R^1$ and $R^2$ is a methyl group and the other is an ethyl group, a propyl group, or a butyl group.

Particularly preferably, the compound (1) is at least one selected from the group consisting of a compound (1-a) represented by the following formula (1-a):

[Chem. 8]

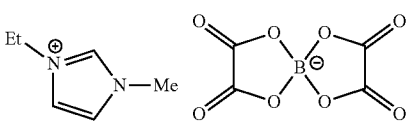

and a compound (1-b) represented by the following formula (1-b):

[Chem. 9]

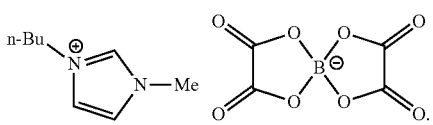

The compound (1) is preferably present in an amount of $4.0 \times 10^{-6}$ to $6.0 \times 10^{-1}$ mol/L relative to the electrolyte solution. The compound (1) in an amount within the above range allows providing a lithium ion secondary battery having much lower resistance and much better cycle characteristics. The amount of the compound (1) is more preferably $4.0 \times 10^{-4}$ mol/L or more, still more preferably $4.0 \times 10^{-3}$ mol/L or more, particularly preferably $1.6 \times 10^{-2}$ mol/L or more, while more preferably $4.0 \times 10^{-1}$ mol/L or less, still more preferably $3.2 \times 10^{-1}$ mol/L or less, further more preferably $2.0 \times 10^{-1}$ mol/L or less, particularly preferably $1.2 \times 10^{-1}$ mol/L or less, relative to the electrolyte solution.

The first electrolyte solution of the invention preferably further contains a chloride ion ($Cl^-$).

The compound (1) can be synthesized by reacting an imidazolium chloride represented by the following formula:

[Chem. 10]

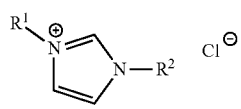

wherein $R^1$ and $R^2$ are defined as described above with lithium bis(oxalato)borate (LIBOB) represented by the following formula:

[Chem. 11]

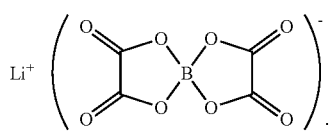

Accordingly, a chloride ion derived from the imidazolium chloride may be left as an impurity. The chloride ion content in the compound (1) can be adjusted by, for example, purifying the compound (1) by silica gel column chromatography.

In the first electrolyte solution of the invention, the chloride ion is present at a concentration of preferably $1.0 \times 10^{-6}$ to $1.0 \times 10^{3}$ ppm. The chloride ion at a concentration within the above range allows providing a lithium ion secondary battery having much lower resistance and much better cycle characteristics. The concentration of the chloride ion is more preferably $1.0 \times 10^{-5}$ ppm or more, still more preferably $1.0 \times 10^{-3}$ ppm or more, further more preferably $1.0 \times 10^{-2}$ ppm or more, particularly preferably $3.0 \times 10^{-2}$ ppm or more, most preferably $6.0 \times 10^{-1}$ ppm or more, while more preferably 100 ppm or less, still more preferably 55 ppm or less, further more preferably 30 ppm or less, still further more preferably 15 ppm or less, particularly preferably 8.0 ppm or less, most preferably 3.0 ppm or less.

The first electrolyte solution of the invention preferably further contains $LiPF_6$ as a compound containing a lithium ion.

$LiPF_6$ is preferably present in an amount of 0.01 to 5.0 mol/L relative to the electrolyte solution. $LiPF_6$ in an amount within the above range allows providing a lithium ion secondary battery having much lower resistance and much better cycle characteristics. The amount of $LiPF_6$ is more preferably 0.5 mol/L or more, still more preferably 0.7 mol/L or more, particularly preferably 0.8 mol/L or more, relative to the electrolyte solution. The amount of $LiPF_6$ is more preferably 1.8 mol/L or less, still more preferably 1.5 mol/L or less, particularly preferably 1.2 mol/L or less.

The second electrolyte solution of the invention contains an imidazolium cation (1-1) represented by the following formula (1-1):

[Chem. 12]

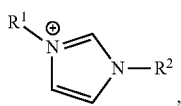

a bis(oxalato)borate anion, and a hexafluorophosphate anion. The presence of the above specific ions allows the second electrolyte solution of the invention to provide a lithium ion secondary battery having low resistance and excellent cycle characteristics.

The bis(oxalato)borate anion is an anion represented by the following formula:

[Chem. 13]

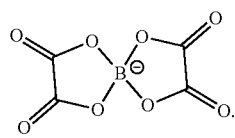

and the hexafluorophosphate anion is an anion represented by $PF_6^-$.

In the formula (1-1), $R^1$ and $R^2$ are each independently a C1-C4 alkyl group optionally containing an ether bond. Specific examples and preferred combinations of $R^1$ and $R^2$ are the same as those mentioned for the formula (1).

The imidazolium cation (1-1) is preferably at least one selected from the group consisting of an imidazolium cation (1-1a) represented by

[Chem. 14]

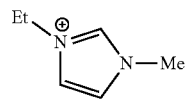

and an imidazolium cation (1-1b) represented by

[Chem. 15]

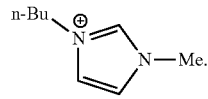

In the second electrolyte solution of the invention, preferably, the imidazolium cation (1-1) is present at a concentration of $1.0 \times 10^{-5}$ to 1.0 mol/L, the bis(oxalato)borate anion is present at a concentration of $1.0 \times 10^{-5}$ to 1.0 mol/L, and the hexafluorophosphate anion is present at a concentration of 0.01 to 1.5 mol/L. These ions at concentrations within the above respective ranges allow providing a lithium ion secondary battery having much lower resistance and much better cycle characteristics.

The concentration of the imidazolium cation (1-1) is more preferably $1.0 \times 10^{-4}$ mol/L or more, still more preferably $5.0 \times 10^{-3}$ mol/L or more, further more preferably $1.0 \times 10^{-2}$ mol/L or more, particularly preferably $3.0 \times 10^{-2}$ mol/L or more, while more preferably $5.0 \times 10^{-1}$ mol/L or less, still more preferably $4.5 \times 10^{-1}$ mol/L or less, further more preferably $3.0 \times 10^{-1}$ mol/L or less, particularly preferably $1.5 \times 10^{-1}$ mol/L or less, most preferably $1.0 \times 10^{-1}$ mol/L or less.

The concentration of the bis(oxalato)borate anion is more preferably $1.0 \times 10^{-4}$ mol/L or more, still more preferably $5.0 \times 10^{-3}$ mol/L or more, further more preferably $1.0 \times 10^{-2}$ mol/L or more, particularly preferably $3.0 \times 10^{-2}$ mol/L or more, while more preferably $5.0 \times 10^{-1}$ mol/L or less, still more preferably $4.5 \times 10^{-1}$ mol/L or less, further more preferably $3.0 \times 10^{-1}$ mol/L or less, particularly preferably $1.5 \times 10^{-1}$ mol/L or less, most preferably $1.0 \times 10^{-1}$ mol/L or less.

The concentration of the hexafluorophosphate anion is more preferably 0.10 mol/L or more, still more preferably 0.50 mol/L or more, particularly preferably 0.80 mol/L or more, while more preferably 1.2 mol/L or less, still more preferably 1.1 mol/L or less.

The second electrolyte solution of the invention preferably further contains a chloride ion. In this case, the chloride ion is preferably present at a concentration of $1.0 \times 10^{-6}$ to $1.0 \times 10^3$ ppm. The chloride ion at a concentration within the above range allows providing a lithium ion secondary battery having much lower resistance and much better cycle characteristics. The concentration of the chloride ion is more preferably $1.0 \times 10^{-5}$ ppm or more, still more preferably $1.0 \times 10^{-3}$ ppm or more, further more preferably $1.0 \times 10^{-2}$ ppm or more, particularly preferably $3.0 \times 10^{-2}$ ppm or more, most preferably $6.0 \times 10^{-1}$ ppm or more, while more preferably 100 ppm or less, still more preferably 55 ppm or less, further more preferably 30 ppm or less, still further more preferably 15 ppm or less, particularly preferably 8.0 ppm or less, most preferably 3.0 ppm or less.

Examples of ion sources of the ions contained in the second electrolyte solution of the invention include compounds that contain the target ion(s) and are soluble in the solvent constituting the electrolyte solution. One or two or more of the ion sources may be used for each ion.

Examples of the ion source of the imidazolium cation (1-1) include the above described compound (1) and a compound containing the imidazolium cation (1-1) and a counter anion other than a bis(oxalato)borate anion.

Examples of the counter anion other than a bis(oxalato)borate anion include $PF_6^-$, $N(FSO_2)_2^-$, $N(CF_3SO_2)_2^-$, $ClO_4^-$, $Cl^-$, and $BF_4^-$, with $PF_6^-$ being preferred.

Examples of the ion source of the bis(oxalato)borate anion include the above described compound (1) and a compound containing a bis(oxalato)borate anion and a counter cation other than the imidazolium cation (1-1).

Examples of the counter cation other than the imidazolium cation (1-1) include $Li^+$, an ammonium cation, a pyridinium cation, a pyrrolidinium cation, and a piperidinium cation, with $Li^+$ being preferred.

In order to provide a lithium ion secondary battery having much lower resistance and much better cycle characteristics, the compound (1) is preferably used as an ion source of both the imidazolium cation (1-1) and the bis(oxalato)borate anion.

Examples of the ion source of the hexafluorophosphate anion include a compound containing a hexafluorophosphate anion and a counter cation.

Examples of the counter cation include the imidazolium cation (1-1), $Li^+$, an ammonium cation, a pyridinium cation, a pyrrolidinium cation, and a piperidinium cation, with the imidazolium cation (1-1) and $Li^+$ being preferred and $Li^+$ being more preferred.

The chloride ion may be contained in the compound (1) as an impurity as described above. Accordingly, the compound (1) may be used as the ion source of the chloride ion. In this case, the chloride ion content in the compound (1) can be adjusted by, for example, purifying the compound (1) by silica gel column chromatography.

Examples of a different ion source of the chloride ion include chlorides such as lithium chloride, ammonium chloride, pyridinium chloride, pyrrolidinium chloride, and piperidinium chloride.

The second electrolyte solution of the invention preferably further contains a lithium ion ($Li^+$). The lithium ion present in the electrolyte solution is preferably at a concentration of 0.01 to 1.5 mol/L. The concentration of the lithium ion is more preferably 0.10 mol/L or more, still more preferably 0.50 mol/L or more, particularly preferably 0.80 mol/L or more, while more preferably 1.2 mol/L or less, still more preferably 1.1 mol/L or less.

Examples of the ion source of the lithium ion include a compound containing a lithium ion and a counter anion. Specific examples thereof include the later-described compound (5) (wherein $A^{a+}$ is a lithium ion) and a lithium salt other than the compound (5). Preferred among these are $LiPF_6$, lithium bis(oxalato)borate, and lithium chloride, more preferred are $LiPF_6$ and lithium bis(oxalato)borate, and still more preferred is $LiPF_6$.

The electrolyte solution (each of the first and second electrolyte solutions) of the invention preferably contains a solvent.

The solvent preferably contains a carbonate or an ester.

The solvent may contain a cyclic carbonate or an acyclic carbonate.

The cyclic carbonate may be either a non-fluorinated cyclic carbonate or a fluorinated cyclic carbonate.

The acyclic carbonate may be either a non-fluorinated acyclic carbonate or a fluorinated acyclic carbonate.

The solvent preferably contains at least one selected from the group consisting of a non-fluorinated saturated cyclic carbonate, a fluorinated saturated cyclic carbonate, a fluorinated acyclic carbonate, and a non-fluorinated acyclic carbonate.

An example of the non-fluorinated saturated cyclic carbonate is a non-fluorinated saturated cyclic carbonate containing a C2-C4 alkylene group.

In order to give high permittivity and suitable viscosity, the non-fluorinated saturated cyclic carbonate preferably includes at least one selected from the group consisting of ethylene carbonate, propylene carbonate, dipropyl carbonate, dibutyl carbonate, cis-2,3-pentylene carbonate, cis-2,3-butylene carbonate, 2,3-pentylene carbonate, 2,3-butylene carbonate, 1,2-pentylene carbonate, 1,2-butylene carbonate, methyl isopropyl carbonate, and butylene carbonate.

One non-fluorinated saturated cyclic carbonate may be used alone, or two or more thereof may be used in any combination at any ratio.

The non-fluorinated saturated cyclic carbonate, when contained, is preferably present in an amount of 5 to 90% by volume, more preferably 10 to 60% by volume, still more preferably 15 to 45% by volume, relative to the solvent.

Examples of the non-fluorinated acyclic carbonate include hydrocarbon-based acyclic carbonates such as $CH_3OCOOCH_3$ (dimethyl carbonate, DMC), $CH_3CH_2OCOOCH_2CH_3$ (diethyl carbonate, DEC), $CH_3CH_2OCOOCH_3$ (ethyl methyl carbonate, EMC), $CH_3OCOOCH_2CH_2CH_3$ (methyl propyl carbonate), methyl butyl carbonate, ethyl propyl carbonate, ethyl butyl carbonate, methyl-2-phenyl phenyl carbonate, phenyl-2-phenyl phenyl carbonate, trans-2,3-pentylene carbonate, trans-2,3-butylene carbonate, and ethyl phenyl carbonate. Preferred among these is at least one selected from the group consisting of ethyl methyl carbonate, diethyl carbonate, and dimethyl carbonate.

One non-fluorinated acyclic carbonate may be used alone or two or more thereof may be used in any combination at any ratio.

The non-fluorinated acyclic carbonate, when contained, is preferably present in an amount of 10 to 90% by volume, more preferably 40 to 85% by volume, still more preferably 50 to 80% by volume, relative to the solvent.

The solvent preferably contains both the non-fluorinated acyclic carbonate and the non-fluorinated cyclic carbonate. An electrolyte solution containing a solvent of such a composition can suitably be used for electrochemical devices used at relatively low voltage.

The solvent preferably contains 20 to 100% by volume, more preferably 30 to 95% by volume, still more preferably 50 to 90% by volume, in total of the non-fluorinated saturated cyclic carbonate and the non-fluorinated acyclic carbonate.

For the electrolyte solution containing both the non-fluorinated cyclic carbonate and the non-fluorinated acyclic carbonate, the non-fluorinated cyclic carbonate and the non-fluorinated acyclic carbonate preferably give a volume ratio of 5/95 to 95/5, more preferably 10/90 or higher, still more preferably 15/85 or higher, particularly preferably 20/80 or higher, while more preferably 90/10 or lower, still more preferably 60/40 or lower.

When the solvent contains at least one selected from the group consisting of the non-fluorinated acyclic carbonate and the non-fluorinated cyclic carbonate, the electrolyte solution of the invention may further contain the fluorinated saturated cyclic carbonate as an additive. In this case, preferred examples of the fluorinated saturated cyclic carbonate include fluoroethylene carbonate and difluoroethylene carbonate, and a preferred amount thereof is 0.1 to 5% by mass relative to the solvent.

The solvent may contain a cyclic ester or an acyclic ester.

The cyclic ester may be either a non-fluorinated cyclic ester or a fluorinated cyclic ester.

The acyclic carbonate may be either a non-fluorinated acyclic ester or a fluorinated acyclic ester.

The solvent preferably contains at least one selected from the group consisting of a non-fluorinated saturated cyclic ester, a fluorinated saturated cyclic ester, a fluorinated acyclic ester, and a non-fluorinated acyclic ester.

An example of the non-fluorinated saturated cyclic ester is a non-fluorinated saturated cyclic ester containing a C2-C4 alkylene group.

Specific examples of the non-fluorinated saturated cyclic ester containing a C2-C4 alkylene group include β-propiolactone, γ-butyrolactone, ε-caprolactone, δ-valerolactone, and α-methyl-γ-butyrolactone. In order to improve the degree of dissociation of lithium ions and to improve the load characteristics, particularly preferred among these are γ-butyrolactone and δ-valerolactone.

One non-fluorinated saturated cyclic ester may be used alone or two or more thereof may be used in any combination at any ratio.

Examples of the non-fluorinated acyclic ester include methyl acetate, ethyl acetate, propyl acetate, butyl acetate, methyl propionate, ethyl propionate, propyl propionate, butyl propionate, tert-butyl propionate, tert-butyl butyrate, sec-butyl propionate, sec-butyl butyrate, n-butyl butyrate, methyl pyrophosphate, ethyl pyrophosphate, tert-butyl formate, tert-butyl acetate, sec-butyl formate, sec-butyl acetate, n-hexyl pivalate, n-propyl formate, n-propyl acetate, n-butyl formate, n-butyl pivalate, n-octyl pivalate, ethyl 2-(dimethoxyphosphoryl)acetate, ethyl 2-(dimethylphosphoryl)acetate, ethyl 2-(diethoxyphosphoryl)acetate, ethyl 2-(diethylphosphoryl)acetate, isopropyl propionate, isopropyl acetate, ethyl formate, ethyl 2-propynyl oxalate, isopropyl formate, isopropyl butyrate, isobutyl formate, isobutyl propionate, isobutyl butyrate, and isobutyl acetate.

Preferred among these are butyl acetate, methyl propionate, ethyl propionate, propyl propionate, and butyl propionate, particularly preferred are ethyl propionate and propyl propionate.

One non-fluorinated acyclic ester may be used alone or two or more thereof may be used in any combination at any ratio.

The non-fluorinated saturated cyclic ester is preferably present in an amount of 0 to 90% by volume, more preferably 0.001 to 90% by volume, still more preferably 1 to 60% by volume, particularly preferably 5 to 40% by volume, relative to the solvent.

The non-fluorinated acyclic ester is preferably present in an amount of 0 to 90% by volume, more preferably 0.001 to 90% by volume, still more preferably 1 to 60% by volume, particularly preferably 5 to 40% by volume, relative to the solvent.

The sum of the non-fluorinated saturated cyclic ester and the non-fluorinated acyclic ester is preferably 0 to 90% by volume, more preferably 1 to 60% by volume, still more preferably 5 to 40% by volume, relative to the solvent.

In order to enable suitable use at high voltage, the solvent preferably contains a fluorinated cyclic carbonate. The fluorinated cyclic carbonate may be either a fluorinated saturated cyclic carbonate or a fluorinated unsaturated cyclic carbonate.

The term "high voltage" herein means a voltage of 4.2 V or higher. The upper limit of the "high voltage" is preferably 4.9 V.

The fluorinated saturated cyclic carbonate is a saturated cyclic carbonate with a fluorine atom added thereto. Specific examples thereof include a compound represented by the following formula (A):

[Chem. 16]

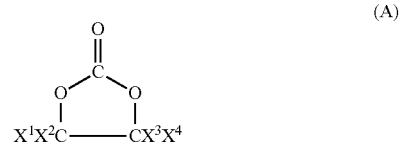
(A)

(wherein $X^1$ to $X^4$ are the same as or different from each other, and are each —H, —$CH_3$, —$C_2H_5$, —F, a fluorinated alkyl group optionally containing an ether bond, or a fluorinated alkoxy group optionally containing an ether bond; at least one selected from $X^1$ to $X^4$ is —F, a fluorinated alkyl group optionally containing an ether bond, or a fluorinated alkoxy group optionally containing an ether bond). Examples of the fluorinated alkyl group include —$CF_3$, —$CF_2H$, and —$CH_2F$.

The presence of the fluorinated saturated cyclic carbonate in the electrolyte solution of the invention when applied to a high-voltage lithium ion secondary battery, for example, can improve the oxidation resistance of the electrolyte solution, resulting in stable and excellent charge and discharge characteristics.

The term "ether bond" herein means a bond represented by —O—.

In order to give a good permittivity and oxidation resistance, one or two of $X^1$ to $X^4$ is/are each preferably —F, a fluorinated alkyl group optionally containing an ether bond, or a fluorinated alkoxy group optionally containing an ether bond.

In anticipation of a decrease in viscosity at low temperature, an increase in flash point, and improvement in solubility of an electrolyte salt, $X^1$ to $X^4$ are each preferably —H, —F, a fluorinated alkyl group (a), a fluorinated alkyl group (b) containing an ether bond, or a fluorinated alkoxy group (c).

The fluorinated alkyl group (a) is a group obtainable by replacing at least one hydrogen atom of an alkyl group by a fluorine atom. The fluorinated alkyl group (a) preferably has a carbon number of 1 to 20, more preferably 1 to 17, still more preferably 1 to 7, particularly preferably 1 to 5.

Too large a carbon number may cause poor low-temperature characteristics and low solubility of an electrolyte salt. Too small a carbon number may cause low solubility of an electrolyte salt, low discharge efficiency, and increased viscosity, for example.

Examples of the fluorinated alkyl group (a) having a carbon number of 1 include $CFH_2$—, $CF_2H$—, and $CF_3$—. In order to give good high-temperature storage characteristics, particularly preferred is $CF_2H$— or $CF_3$—. Most preferred is $CF_3$—.

In order to give good solubility of an electrolyte salt, preferred examples of the fluorinated alkyl group (a) having a carbon number of 2 or greater include fluorinated alkyl groups represented by the following formula (a-1):

$$R^1\text{-}R^2\text{—} \tag{a-1}$$

wherein $R^1$ is an alkyl group having a carbon number of 1 or greater and optionally containing a fluorine atom; $R^2$ is a C1-C3 alkylene group optionally containing a fluorine atom; and at least one selected from $R^1$ and $R^2$ contains a fluorine atom.

$R^1$ and $R^2$ each may further contain an atom other than carbon, hydrogen, and fluorine atoms.

$R^1$ is an alkyl group having a carbon number of 1 or greater and optionally containing a fluorine atom. $R^1$ is preferably a C1-C16 linear or branched alkyl group. The carbon number of $R^1$ is more preferably 1 to 6, still more preferably 1 to 3.

Specifically, for example, $CH_3-$, $CH_3CH_2-$, $CH_3CH_2CH_2-$, $CH_3CH_2CH_2CH_2-$, and groups represented by the following formulae:

[Chem. 17]

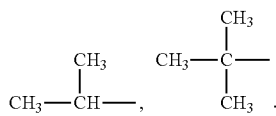

may be mentioned as linear or branched alkyl groups for $R^1$.

Examples of $R^1$ which is a linear alkyl group containing a fluorine atom include $CF_3-$, $CF_3CH_2-$, $CF_3CF_2-$, $CF_3CH_2CH_2-$, $CF_3CF_2CH_2-$, $CF_3CF_2CF_2-$, $CF_3CH_2CF_2-$, $CF_3CH_2CH_2CH_2-$, $CF_3CF_2CH_2CH_2-$, $CF_3CH_2CF_2CH_2-$, $CF_3CF_2CF_2CH_2-$, $CF_3CF_2CF_2CF_2-$, $CF_3CF_2CH_2CF_2-$, $CF_3CH_2CH_2CH_2CH_2-$, $CF_3CF_2CH_2CH_2CH_2-$, $CF_3CH_2CF_2CH_2CH_2-$, $CF_3CF_2CF_2CH_2CH_2-$, $CF_3CF_2CF_2CF_2CH_2-$, $CF_3CF_2CH_2CF_2CH_2-$, $CF_3CF_2CH_2CH_2CH_2CH_2-$, $CF_3CF_2CF_2CF_2CH_2CH_2-$, $CF_3CF_2CH_2CF_2CH_2CH_2-$, $HCF_2-$, $HCF_2CH_2-$, $HCF_2CF_2-$, $HCF_2CH_2CH_2-$, $HCF_2CF_2CH_2-$, $HCF_2CH_2CF_2-$, $HCF_2CF_2CH_2CH_2-$, $HCF_2CH_2CF_2CH_2-$, $HCF_2CF_2CF_2CF_2-$, $HCF_2CF_2CH_2CH_2CH_2-$, $HCF_2CH_2CF_2CH_2CH_2-$, $HCF_2CF_2CF_2CF_2CH_2-$, $HCF_2CF_2CF_2CF_2CH_2CH_2-$, $FCH_2-$, $FCH_2CH_2-$, $FCH_2CF_2-$, $FCH_2CF_2CH_2-$, $FCH_2CF_2CF_2-$, $CH_3CF_2CH_2-$, $CH_3CF_2CF_2-$, $CH_3CF_2CH_2CF_2-$, $CH_3CF_2CF_2CF_2-$, $CH_3CH_2CF_2CF_2-$, $CH_3CF_2CH_2CF_2CH_2-$, $CH_3CF_2CF_2CF_2CH_2-$, $CH_3CF_2CH_2CH_2CH_2-$, $CH_3CH_2CF_2CF_2CH_2-$, $CH_3CF_2CH_2CF_2CH_2CH_2-$, $CH_3CF_2CH_2CF_2CH_2CH_2-$, $CH_3CF_2CH_2CF_2CH_2CH_2-$, $HCFClCF_2CH_2-$, $HCF_2CFClCH_2-$, $HCF_2CFClCF_2CFClCH_2-$, and $HCFClCF_2CFClCF_2CH_2-$.

Examples of $R^1$ which is a branched alkyl group containing a fluorine atom include those represented by the following formulae.

[Chem. 18]

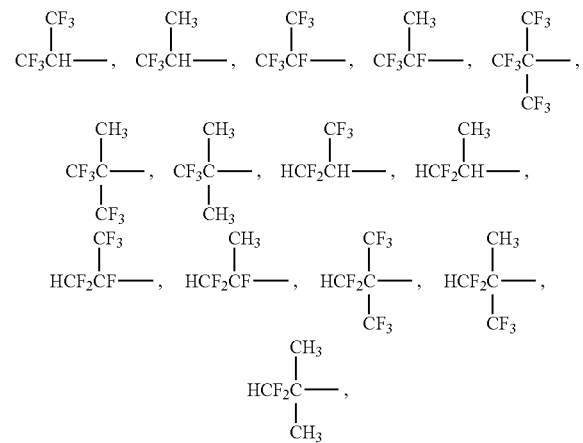

[Chem. 19]

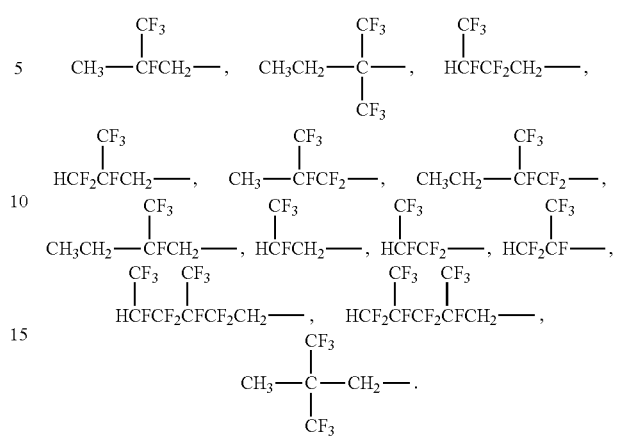

The presence of a branch such as $CH_3-$ or $CF_3-$ may easily cause high viscosity. Thus, the number of such branches is more preferably small (one) or zero.

$R^2$ is a C1-C3 alkylene group optionally containing a fluorine atom. $R^2$ may be either linear or branched. Examples of a minimum structural unit constituting such a linear or branched alkylene group are shown below. $R^2$ is constituted by one or combination of these units.

(i) Linear minimum structural units

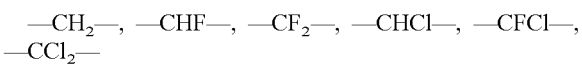

(ii) Branched minimum structural units

[Chem. 20]

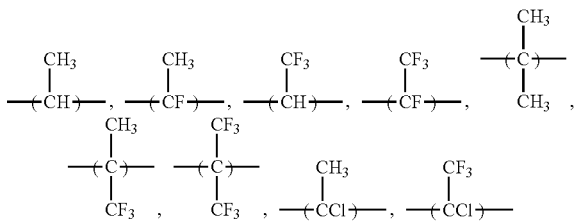

Preferred among these exemplified units are Cl-free structural units because such units may not be dehydrochlorinated by a base, and thus may be more stable.

$R^2$ which is a linear group consists only of any of the above linear minimum structural units, and is preferably $-CH_2-$, $-CH_2CH_2-$, or $CF_2-$. In order to further improve the solubility of an electrolyte salt, $-CH_2-$ or $-CH_2CH_2-$ is more preferred.

$R^2$ which is a branched group includes at least one of the above branched minimum structural units. A preferred example thereof is a group represented by $-(CX^aX^b)-$ (wherein $X^a$ is H, F, $CH_3$, or $CF_3$; $X^b$ is $CH_3$ or $CF_3$; when $X^b$ is $CF_3$, $X^a$ is H or $CH_3$). Such a group can much further improve the solubility of an electrolyte salt.

For example, $CF_3CF_2-$, $HCF_2CF_2-$, $H_2CFCF_2-$, $CH_3CF_2-$, $CF_3CHF-$, $CH_3CF_2-$, $CF_3CF_2CF_2-$, $HCF_2CF_2CF_2-$, $H_2CFCF_2CF_2-$, $CH_3CF_2CF_2-$, and those represented by the following formulae:

[Chem. 21]

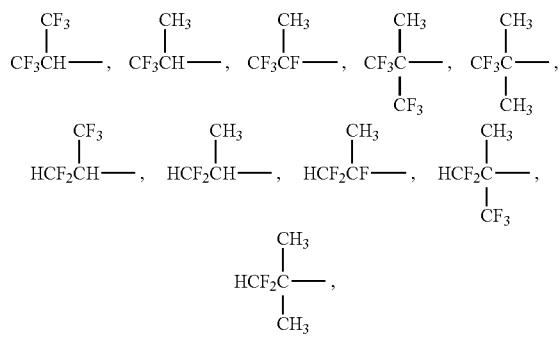

[Chem. 22]

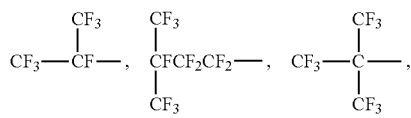

may be mentioned as preferred examples of the fluorinated alkyl group (a).

The fluorinated alkyl group (b) containing an ether bond is a group obtainable by replacing at least one hydrogen atom of an alkyl group containing an ether bond by a fluorine atom. The fluorinated alkyl group (b) containing an ether bond preferably has a carbon number of 2 to 17. Too large a carbon number may cause high viscosity of the fluorinated saturated cyclic carbonate. This may also cause the presence of many fluorine-containing groups, resulting in poor solubility of an electrolyte salt due to reduction in permittivity, and poor miscibility with other solvents. Accordingly, the carbon number of the fluorinated alkyl group (b) containing an ether bond is preferably 2 to 10, more preferably 2 to 7.

The alkylene group which constitutes the ether moiety of the fluorinated alkyl group (b) containing an ether bond is a linear or branched alkylene group. Examples of a minimum structural unit constituting such a linear or branched alkylene group are shown below.

(i) Linear minimum structural units

—$CH_2$—, —CHF—, —$CF_2$—, —CHCl—, —CFCl—, —$CCl_2$—

(ii) Branched minimum structural units

[Chem. 23]

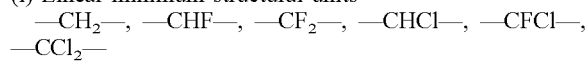

The alkylene group may be constituted by one of these minimum structural units, or may be constituted by multiple linear units (i), by multiple branched units (ii), or by a combination of a linear unit (i) and a branched unit (ii). Preferred examples will be mentioned in detail later.

Preferred among these exemplified units are Cl-free structural units because such units may not be dehydrochlorinated by a base, and thus may be more stable.

A still more preferred example of the fluorinated alkyl group (b) containing an ether bond is a group represented by the following formula (b-1):

$$R^3(OR^4)_{n1}— \qquad (b\text{-}1)$$

wherein $R^3$ is preferably a C1-C6 alkyl group optionally containing a fluorine atom; $R^4$ is preferably a C1-C4 alkylene group optionally containing a fluorine atom; n1 is an integer of 1 to 3; and at least one selected from $R^3$ and $R^4$ contains a fluorine atom.

Examples of $R^3$ and $R^4$ include the following groups, and any appropriate combination of these groups can provide the fluorinated alkyl group (b) containing an ether bond represented by the formula (b-1). Still, the groups are not limited thereto.

(1) $R^3$ is preferably an alkyl group represented by the formula: $X^e{}_3C—(R^5)_{n2}—$, wherein three $X^e$s are the same as or different from each other, and are each H or F; $R^5$ is a C1-C5 alkylene group optionally containing a fluorine atom; and n2 is 0 or 1.

When n2 is 0, $R^3$ may be $CH_3$—, $CF_3$—, $HCF_2$—, or $H_2CF$—, for example.

When n2 is 1, specific examples of $R^3$ which is a linear group include $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CH_2CF_2CH_2$—, $CF_3CF_2CF_2CF_2CH_2$—, $CF_3CF_2CF_2CH_2CH_2$—, $CF_3CF_2CH_2CF_2CH_2CH_2$—, $CF_3CF_2CH_2CF_2CH_2CH_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CH_2CF_2CH_2CH_2$—, $HCF_2CF_2CF_2CF_2CH_2$—, $HCF_2CF_2CF_2CF_2CH_2CH_2$—, $FCH_2CH_2$—, $FCH_2CF_2$—, $FCH_2CF_2CH_2$—, $CH_3CF_2$—, $CH_3CH_2$—, $CH_3CF_2CH_2$—, $CH_3CF_2CF_2$—, $CH_3CH_2CH_2$—, $CH_3CF_2CH_2CF_2$—, $CH_3CF_2CF_2CF_2$—, $CH_3CH_2CF_2CF_2$—, $CH_3CH_2CH_2CH_2$—, $CH_3CF_2CH_2CH_2$—, $CH_3CF_2CF_2CF_2CH_2$—, $CH_3CF_2CF_2CH_2CH_2$—, $CH_3CH_2CF_2CF_2CH_2$—, $CH_3CF_2CH_2CF_2CH_2CH_2$—, $CH_3CH_2CF_2CF_2CH_2CH_2$—, and $CH_3CF_2CH_2CF_2CH_2CH_2$—.

When n2 is 1, those represented by the following formulae:

[Chem. 24]

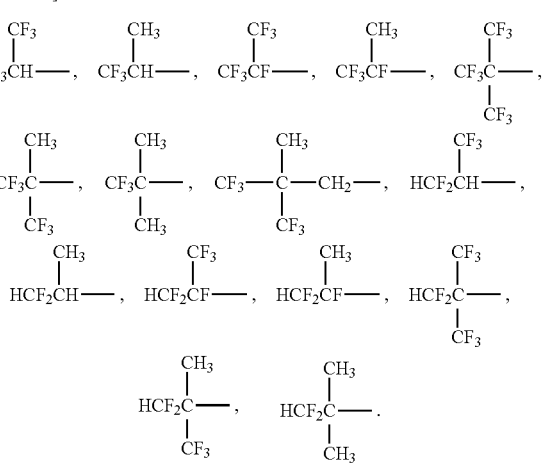

may be mentioned as examples of $R^3$ which is a branched group.

The presence of a branch such as $CH_3$— or $CF_3$— may easily cause high viscosity. Thus, $R^3$ is more preferably a linear group.

(2) In—$(OR^4)_{n1}$— of the formula (b-1), n1 is an integer of 1 to 3, preferably 1 or 2. When n1 is 2 or 3, $R^4$s may be the same as or different from each other.

Preferred specific examples of $R^4$ include the following linear or branched groups.

Examples of the linear groups include —$CH_2$—, —CHF—, —$CF_2$—, —$CH_2CH_2$—, —$CF_2CH_2$—, —$CF_2CF_2$—, —$CH_2CF_2$—, —$CH_2CH_2CH_2$—, —$CH_2CH_2CF_2$—, —$CH_2CF_2CH_2$—, —$CH_2CF_2CF_2$—, —$CF_2CH_2CH_2$—, —$CF_2CF_2CH_2$—, —$CF_2CH_2CF_2$—, and —$CF_2CF_2CF_2$—.

Those represented by the following formulae:

[Chem. 25]

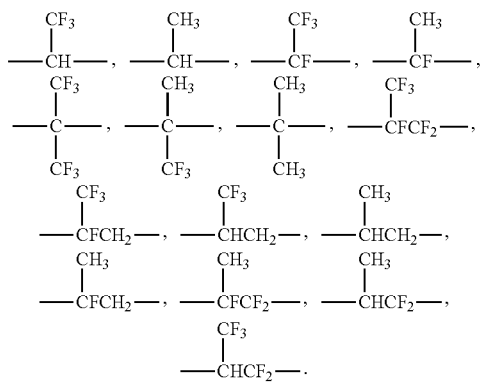

may be mentioned as examples of the branched groups.

The fluorinated alkoxy group (c) is a group obtainable by replacing at least one hydrogen atom of an alkoxy group by a fluorine atom. The fluorinated alkoxy group (c) preferably has a carbon number of 1 to 17, more preferably 1 to 6.

The fluorinated alkoxy group (c) is particularly preferably a fluorinated alkoxy group represented by $X^d{}_3C$—$(R^6)_{n3}$—O—, wherein three $X^d$s are the same as or different from each other, and are each H or F; $R^6$ is preferably a C1-C5 alkylene group optionally containing a fluorine atom; n3 is 0 or 1; and any of the three $X^d$s contain a fluorine atom.

Specific examples of the fluorinated alkoxy group (c) include fluorinated alkoxy groups in which an oxygen atom binds to an end of an alkyl group mentioned as an example for $R^1$ in the formula (a-1).

The fluorinated alkyl group (a), the fluorinated alkyl group (b) containing an ether bond, and the fluorinated alkoxy group (c) in the fluorinated saturated cyclic carbonate each preferably have a fluorine content of 10% by mass or more. Too less a fluorine content may cause a failure in sufficiently achieving an effect of reducing the viscosity at low temperature and an effect of increasing the flash point. Thus, the fluorine content is more preferably 12% by mass or more, still more preferably 15% by mass or more. The upper limit thereof is usually 76% by mass.

The fluorine content of each of the fluorinated alkyl group (a), the fluorinated alkyl group (b) containing an ether bond, and the fluorinated alkoxy group (c) is a value calculated based on the corresponding structural formula by the following formula:

{(Number of fluorine atoms×19)/(Formula weight of group)}×100(%)

In order to give good permittivity and oxidation resistance, the fluorine content in the whole fluorinated saturated cyclic carbonate is preferably 10% by mass or more, more preferably 15% by mass or more. The upper limit thereof is usually 76% by mass.

The fluorine content in the fluorinated saturated cyclic carbonate is a value calculated based on the structural formula of the fluorinated saturated cyclic carbonate by the following formula:

{(Number of fluorine atoms×19)/(Molecular weight of fluorinated saturated cyclic carbonate)}×100 (%).

Specific examples of the fluorinated saturated cyclic carbonate include the following.

Specific examples of the fluorinated saturated cyclic carbonate in which at least one selected from $X^1$ to $X^4$ is —F include those represented by the following formulae.

[Chem. 26]

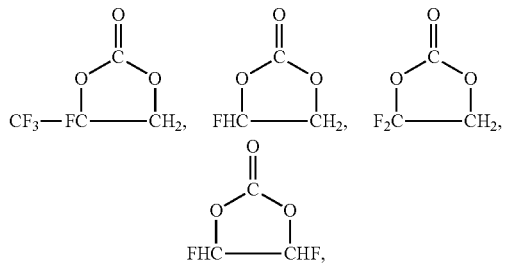

These compounds have a high withstand voltage and give good solubility of an electrolyte salt.

Alternatively, those represented by the following formulae:

[Chem. 27]

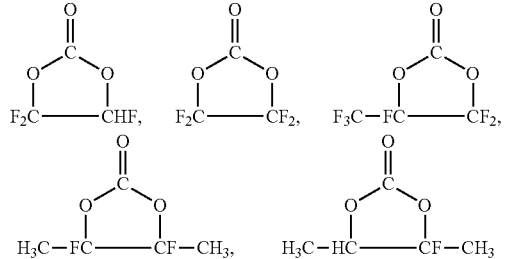

may also be used.

Those represented by the following formulae:

[Chem. 28]

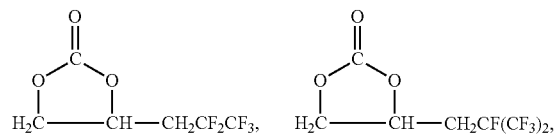

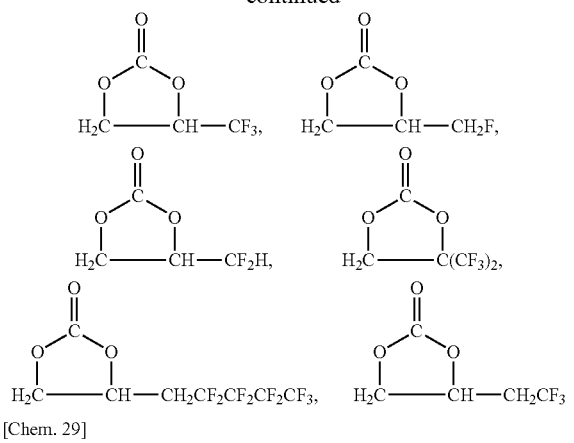
[Chem. 29]
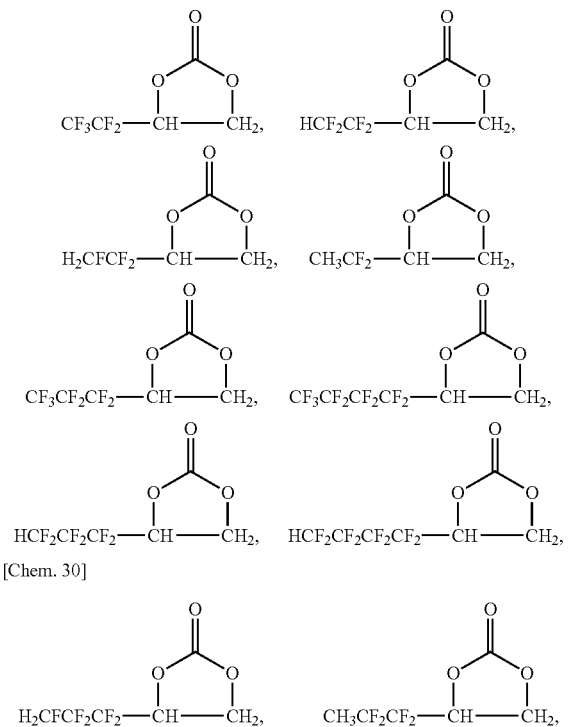
[Chem. 30]
may be mentioned as specific examples of the fluorinated saturated cyclic carbonate in which at least one selected from $X^1$ to $X^4$ is a fluorinated alkyl group (a) and the others are —H.
Those represented by the following formulae:
[Chem. 31]
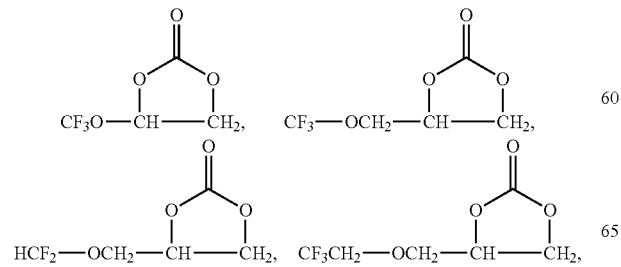
[Chem. 32]
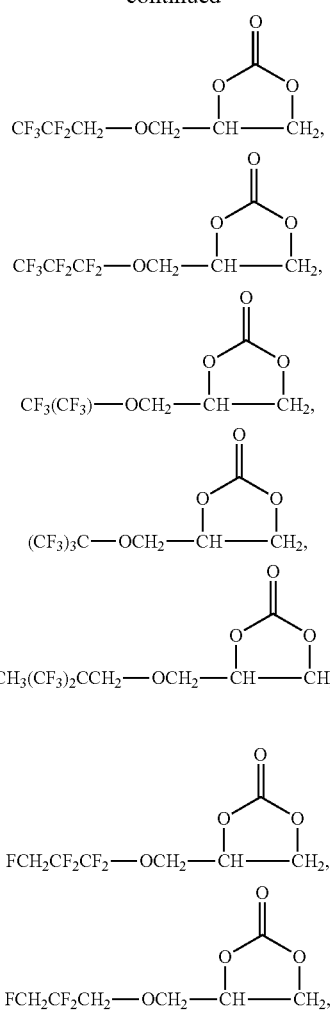
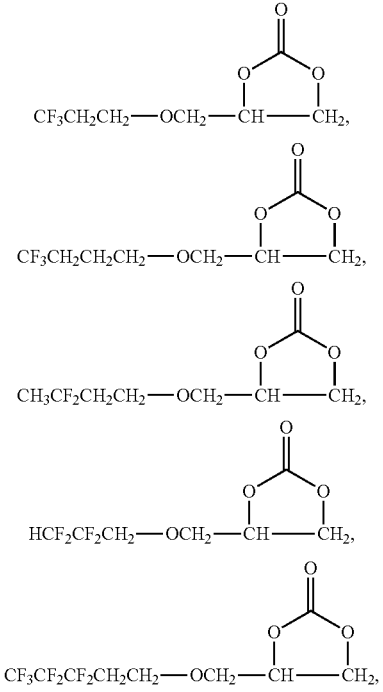

-continued
[Chem. 33]
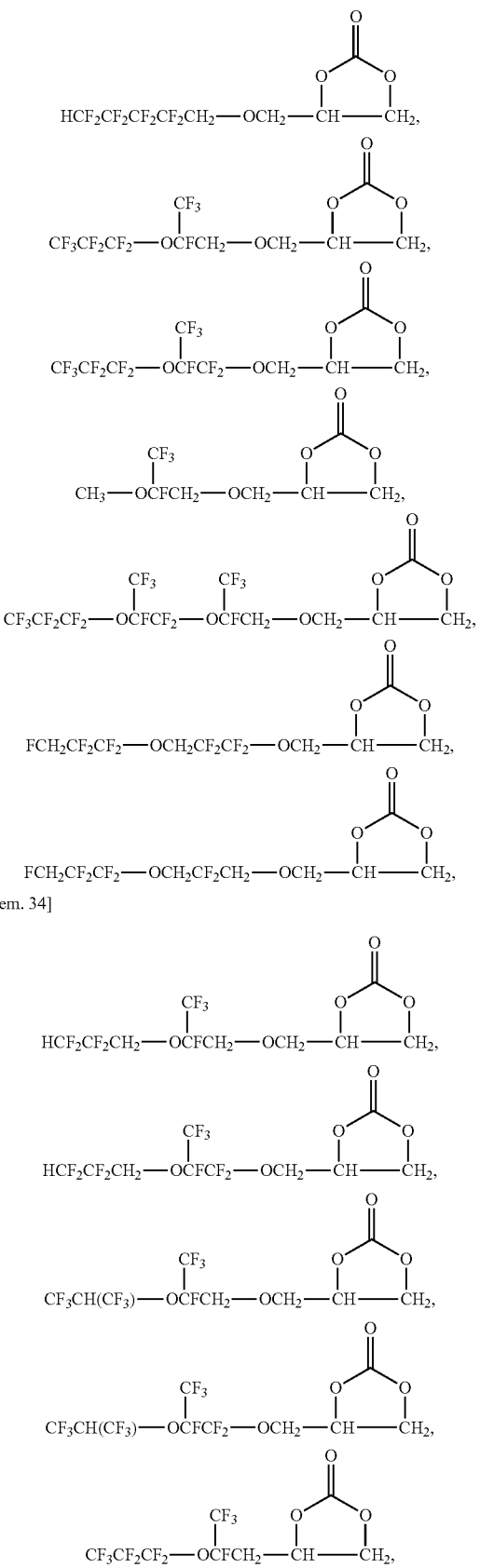
[Chem. 34]
-continued
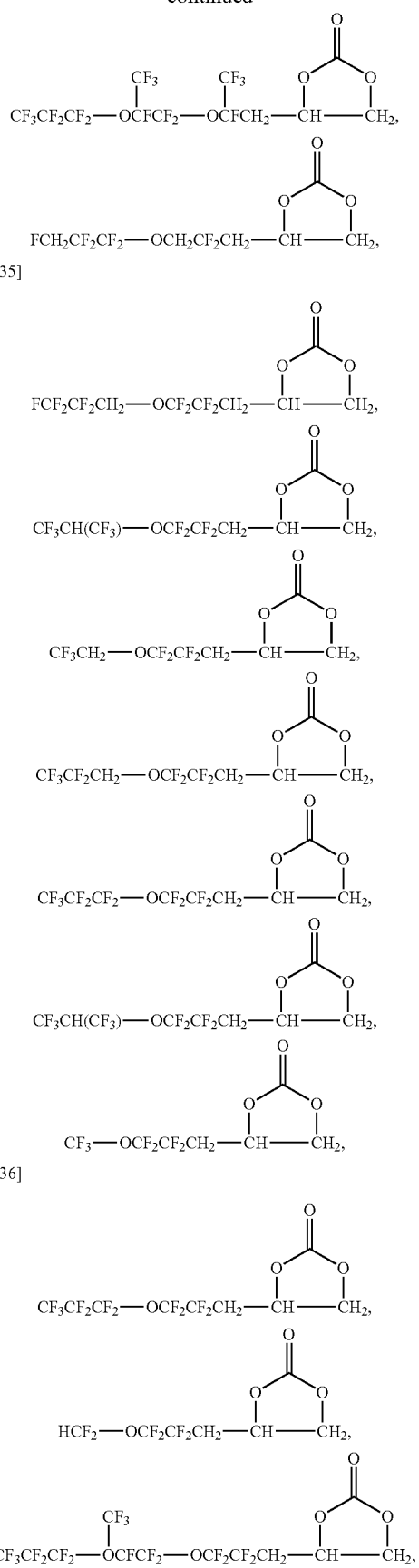
[Chem. 35]
[Chem. 36]

-continued

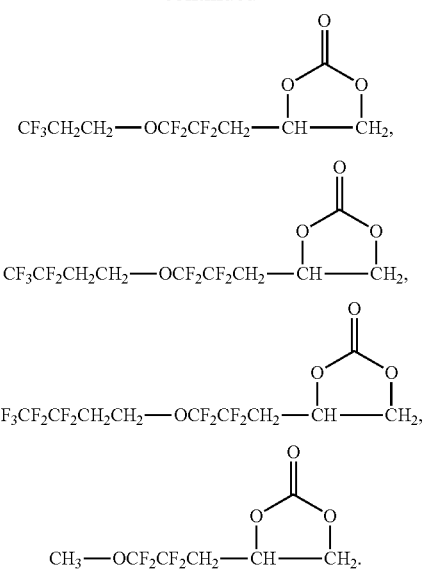

may be mentioned as specific examples of the fluorinated saturated cyclic carbonate in which at least one selected from $X^1$ to $X^4$ is a fluorinated alkyl group (b) containing an ether bond or a fluorinated alkoxy group (c) and the others are —H.

In particular, the fluorinated saturated cyclic carbonate is preferably any of the following compounds.

[Chem.37]

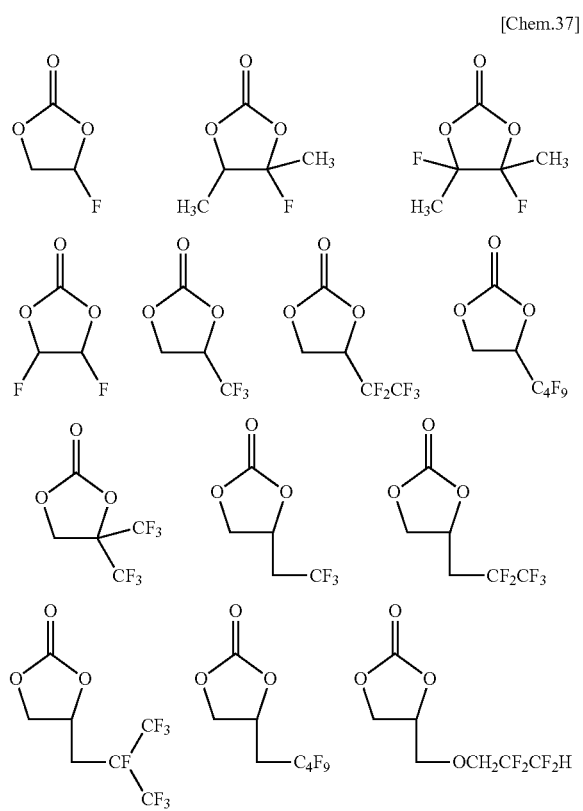

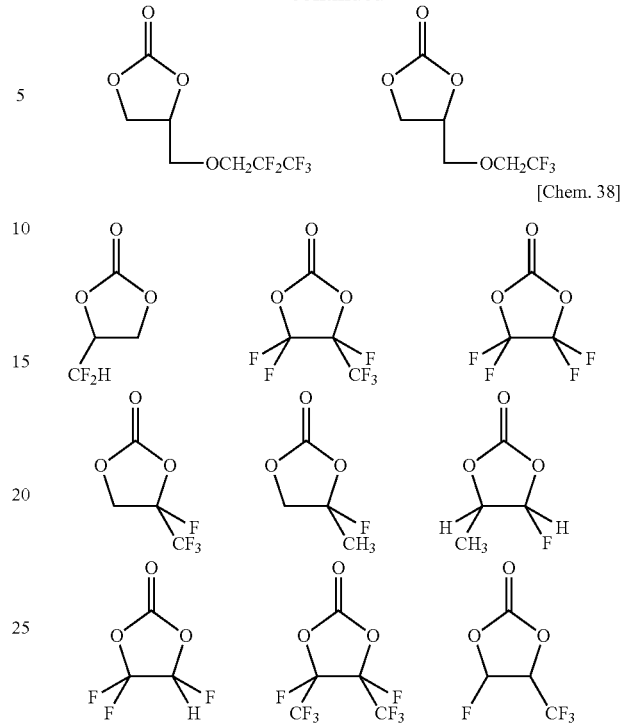

More preferred among these as the fluorinated saturated cyclic carbonate are fluoroethylene carbonate, difluoroethylene carbonate, trifluoromethylethylene carbonate, (3,3,3-trifluoropropylene carbonate), and 2,2,3,3,3-pentafluoropropylethylene carbonate.

Examples of the fluorinated saturated cyclic carbonate also include trans-4,5-difluoro-1,3-dioxolan-2-one, 5-(1,1-difluoroethyl)-4,4-difluoro-1,3-dioxolan-2-one, 4-methylene-1,3-dioxolan-2-one, 4-methyl-5-trifluoromethyl-1,3-dioxolan-2-one, 4-ethyl-5-fluoro-1,3-dioxolan-2-one, 4-ethyl-5,5-difluoro-1,3-dioxolan-2-one, 4-ethyl-4,5-difluoro-1,3-dioxolan-2-one, 4-ethyl-4,5,5-trifluoro-1,3-dioxolan-2-one, 4,4-difluoro-5-methyl-1,3-dioxolan-2-one, 4-fluoro-5-methyl-1,3-dioxolan-2-one, 4-fluoro-5-trifluoromethyl-1,3-dioxolan-2-one, 4,4-difluoro-1,3-dioxolan-2-one, and trifluoromethyl ethylene carbonate.

The fluorinated unsaturated cyclic carbonate is a cyclic carbonate containing an unsaturated bond and a fluorine atom, and is preferably a fluorinated ethylene carbonate derivative substituted with a substituent containing an aromatic ring or a carbon-carbon double bond. Specific examples thereof include 4,4-difluoro-5-phenyl ethylene carbonate, 4,5-difluoro-4-phenyl ethylene carbonate, 4-fluoro-5-phenyl ethylene carbonate, 4-fluoro-5-vinyl ethylene carbonate, 4-fluoro-4-phenyl ethylene carbonate, 4,4-difluoro-4-vinyl ethylene carbonate, 4,4-difluoro-4-allyl ethylene carbonate, 4-fluoro-4-vinyl ethylene carbonate, 4-fluoro-4,5-diallyl ethylene carbonate, 4,5-difluoro-4-vinyl ethylene carbonate, 4,5-difluoro-4,5-divinyl ethylene carbonate, and 4,5-difluoro-4,5-diallyl ethylene carbonate.

The fluorinated cyclic carbonate is not limited to the above specific examples. One fluorinated cyclic carbonate may be used alone or two or more thereof may be used in any combination at any ratio.

The fluorinated cyclic carbonate is preferably present in an amount of 5 to 90% by volume, more preferably 10 to 60% by volume, still more preferably 15 to 45% by volume, relative to the solvent.

In order to be suitably used also at high voltage, the solvent preferably contains a fluorinated acyclic carbonate.

An example of the fluorinated acyclic carbonate is a compound represented by the following formula (B):

$$Rf^2OOCOOR^7 \quad (B)$$

wherein $Rf^2$ is a C1-C7 fluorinated alkyl group; and $R^7$ is a C1-C7 alkyl group optionally containing a fluorine atom.

$Rf^2$ is a C1-C7 fluorinated alkyl group and $R^7$ is a C1-C7 alkyl group optionally containing a fluorine atom.

The fluorinated alkyl group is a group obtainable by replacing at least one hydrogen atom of an alkyl group by a fluorine atom. When $R^7$ is an alkyl group containing a fluorine atom, it is a fluorinated alkyl group.

In order to give low viscosity, $Rf^2$ and $R^7$ each preferably have a carbon number of 1 to 7, more preferably 1 to 2.

Too large a carbon number may cause poor low-temperature characteristics and low solubility of an electrolyte salt. Too small a carbon number may cause low solubility of an electrolyte salt, low discharge efficiency, and increased viscosity, for example.

Examples of the fluorinated alkyl group having a carbon number of 1 include $CFH_2$—, $CF_2H$—, and $CF_3$—. In order to give high-temperature storage characteristics, particularly preferred is $CFH_2$— or $CF_3$—.

In order to give good solubility of an electrolyte salt, preferred examples of the fluorinated alkyl group having a carbon number of 2 or greater include fluorinated alkyl groups represented by the following formula (d-1):

$$R^1\text{-}R^2\text{—} \quad (d\text{-}1)$$

wherein $R^1$ is an alkyl group having a carbon number of 1 or greater and optionally containing a fluorine atom; $R^2$ is a C1-C3 alkylene group optionally containing a fluorine atom; and at least one selected from $R^1$ and $R^2$ contains a fluorine atom.

$R^1$ and $R^2$ each may further contain an atom other than carbon, hydrogen, and fluorine atoms.

$R^1$ is an alkyl group having a carbon number of 1 or greater and optionally containing a fluorine atom. $R^1$ is preferably a C1-C6 linear or branched alkyl group. The carbon number of $R^1$ is more preferably 1 to 6, still more preferably 1 to 3.

Specifically, for example, $CH_3$—, $CF_3$—, $CH_3CH_2$—, $CH_3CH_2CH_2$—, $CH_3CH_2CH_2CH_2$—, and groups represented by the following formulae:

[Chem. 39]

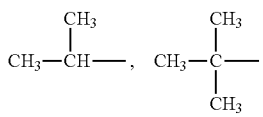

may be mentioned as linear or branched alkyl groups for $R^1$.

Examples of $R^1$ which is a linear alkyl group containing a fluorine atom include $CF_3$—, $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CF_2CF_2CH_2$—, $CF_3CF_2CH_2CH_2CH_2$—, $CF_3CF_2CH_2CF_2CH_2$—, $CF_3CF_2CF_2CF_2CH_2$—, $CF_3CF_2CH_2CF_2CH_2CH_2$—, $CF_3CF_2CF_2CF_2CH_2CH_2$—, $CF_3CH_2CH_2CF_2CH_2CH_2$—, $HCF_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CH_2CF_2CH_2CH_2$—, $HCF_2CF_2CF_2CF_2CH_2$—, $HCF_2CF_2CF_2CH_2CH_2$—, $FCH_2$—, $FCH_2CH_2$—, $FCH_2CF_2$—, $FCH_2CF_2CH_2$—, $FCH_2CF_2CF_2$—, $CH_3CF_2CH_2$—, $CH_3CF_2CF_2$—, $CH_3CF_2CH_2CF_2$—, $CH_3CF_2CF_2CF_2$—, $CH_3CH_2CF_2CF_2$—, $CH_3CF_2CH_2CF_2CH_2$—, $CH_3CF_2CF_2CF_2CH_2$—, $CH_3CF_2CF_2CH_2CH_2$—, $CH_3CH_2CF_2CF_2CH_2$—, $CH_3CF_2CH_2CF_2CH_2CH_2$—, $CH_3CF_2CH_2CF_2CH_2CH_2$—, $CH_3CF_2CH_2CF_2CH_2CH_2$—, $HCFClCF_2CH_2$—, $HCF_2CFClCH_2$—, $HCF_2CFClCF_2CFClCH_2$—, and $HCFClCF_2CFClCF_2CH_2$—.

Examples of $R^1$ which is a branched alkyl group containing a fluorine atom include those represented by the following formulae.

[Chem. 40]

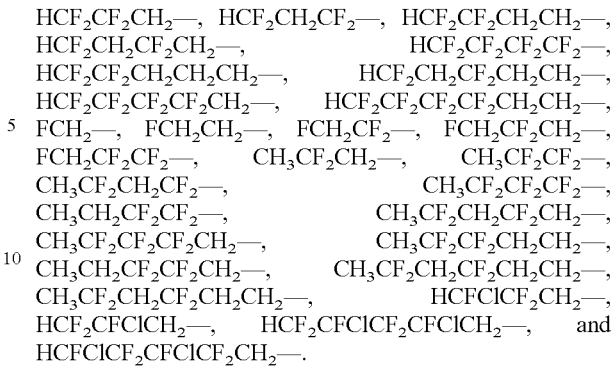

[Chem. 41]

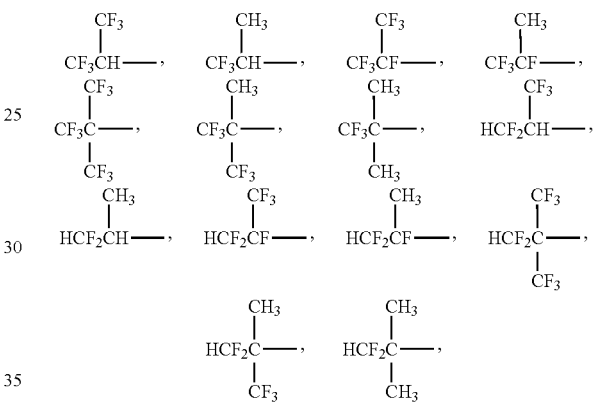

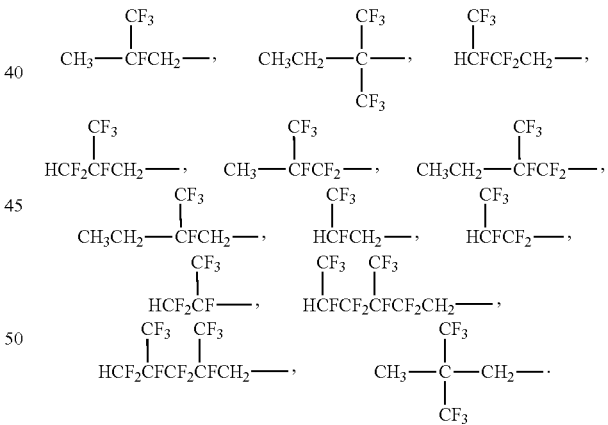

The presence of a branch such as $CH_3$— or $CF_3$— may easily cause high viscosity. Thus, the number of such branches is more preferably small (one) or zero.

$R^2$ is a C1-C3 alkylene group optionally containing a fluorine atom. $R^2$ may be either linear or branched. Examples of a minimum structural unit constituting such a linear or branched alkylene group are shown below. $R^2$ is constituted by one or combination of these units.

(i) Linear minimum structural units

—$CH_2$—, —$CHF$—, —$CF_2$—, —$CHCl$—, —$CFCl$—, —$CCl_2$—

(ii) Branched minimum structural units

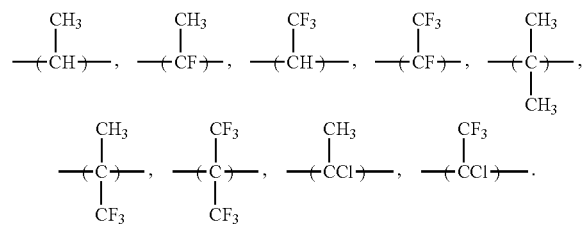
[Chem. 42]

Preferred among these exemplified units are Cl-free structural units because such units may not be dehydrochlorinated by a base, and thus may be more stable.

$R^2$ which is a linear group consists only of any of the above linear minimum structural units, and is preferably —$CH_2$—, —$CH_2CH_2$—, or —$CF_2$—. In order to further improve the solubility of an electrolyte salt, —$CH_2$— or —$CH_2CH_2$— is more preferred.

$R^2$ which is a branched group includes at least one of the above branched minimum structural units. A preferred example thereof is a group represented by —$(CX^aX^b)$— (wherein $X^a$ is H, F, $CH_3$, or $CF_3$; $X^b$ is $CH_3$ or $CF_3$; when $X^b$ is $CF_3$, $X^a$ is H or $CH_3$). Such a group can much further improve the solubility of an electrolyte salt.

For example, $CF_3CF_2$—, $HCF_2CF_2$—, $H_2CFCF_2$—, $CH_3CF_2$—, $CF_3CH_2$—, $CF_3CF_2CF_2$—, $HCF_2CF_2CF_2$—, $H_2CFCF_2CF_2$—, $CH_3CF_2CF_2$—, and those represented by the following formulae:

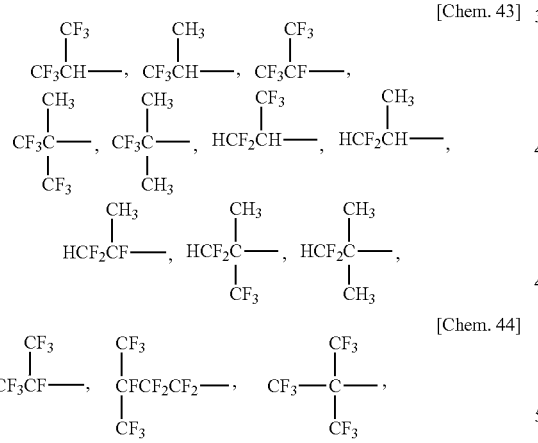
[Chem. 43]

[Chem. 44]

may be specifically mentioned as preferred examples of the fluorinated alkyl group.

The fluorinated alkyl group for $Rf^2$ and $R^7$ is preferably $CF_3$—, $CF_3CF_2$—, $(CF_3)_2CH$—, $CF_3CH_2$—, $C_2F_5CH_2$—, $CF_3CF_2CH_2$—, $HCF_2CF_2CH_2$—, $CF_3CFHCF_2CH_2$—, $CFH_2$—, and $CF_2H$—. In order to give high incombustibility and good rate characteristics and oxidation resistance, more preferred are $CF_3CH_2$—, $CF_3CF_2CH_2$—, $HCF_2CF_2CH_2$—, $CFH_2$—, and $CF_2H$—.

$R^7$, when it is an alkyl group free from a fluorine atom, is a C1-C7 alkyl group. In order to give low viscosity, $R^7$ preferably has a carbon number of 1 to 4, more preferably 1 to 3.

Examples of the alkyl group free from a fluorine atom include $CH_3$—, $CH_3CH_2$—, $(CH_3)_2CH$—, and $C_3H_7$—. In order to give low viscosity and good rate characteristics, preferred are $CH_3$— and $CH_3CH_2$—.

The fluorinated acyclic carbonate preferably has a fluorine content of 20 to 70% by mass. The fluorinated acyclic carbonate having a fluorine content within the above range can maintain the miscibility with a solvent and the solubility of a salt. The fluorine content is more preferably 30% by mass or more, still more preferably 35% by mass or more, while more preferably 60% by mass or less, still more preferably 50% by mass or less.

In the invention, the fluorine content is a value calculated based on the structural formula of the fluorinated acyclic carbonate by the following formula:

{(Number of fluorine atoms×19)/(Molecular weight of fluorinated acyclic carbonate)}×100(%).

In order to give low viscosity, the fluorinated acyclic carbonate is preferably any of the following compounds.

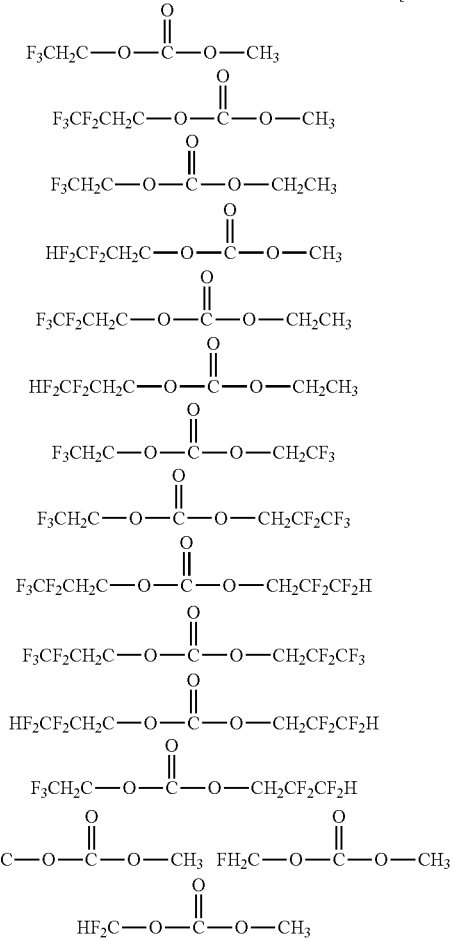
[Chem. 45]

The fluorinated acyclic carbonate is more preferably methyl 2,2,2-trifluoroethyl carbonate.

The fluorinated acyclic carbonate is preferably present in an amount of 10 to 90% by volume, more preferably 40 to 85% by volume, still more preferably 50 to 80% by volume, relative to the solvent.

The solvent preferably contains at least one selected from the group consisting of the fluorinated acyclic carbonate and the fluorinated cyclic carbonate, more preferably contains both the fluorinated acyclic carbonate and the fluorinated cyclic carbonate. An electrolyte solution containing a solvent of such a composition can suitably be used for electrochemical devices used at relatively high voltage.

The solvent preferably contains 10 to 100% by volume in total of the fluorinated cyclic carbonate and the fluorinated acyclic carbonate. The total amount is more preferably 20% by volume or more, still more preferably 30% by volume or more, particularly preferably 40% by volume or more, while more preferably 85% by volume or less, still more preferably 80% by volume or less.

For the solvent containing both the fluorinated cyclic carbonate and the fluorinated acyclic carbonate, the fluorinated cyclic carbonate and the fluorinated acyclic carbonate preferably give a volume ratio of 5/95 to 95/5, more preferably 10/90 or higher, still more preferably 20/80 or higher, particularly preferably 30/70 or higher, while more preferably 80/20 or lower, still more preferably 60/40 or lower.

In order to enable suitable use at high voltage, the solvent also preferably contains a fluorinated acyclic ester. In order to achieve good miscibility with other solvents and to give good oxidation resistance, the fluorinated acyclic ester is preferably a fluorinated acyclic ester represented by the following formula:

$$Rf^{31}COORf^{32}$$

wherein $Rf^{31}$ is a C1-C4 fluorinated alkyl group; and $Rf^{32}$ is a C1-C4 alkyl group optionally containing a fluorine atom.

Examples of $Rf^{31}$ include $HCF_2-$, $CF_3-$, $CF_3CF_2-$, $HCF_2CF_2-$, $CH_3CF_2-$, and $CF_3CH_2-$. In order to achieve good viscosity and oxidation resistance, particularly preferred are $HCF_2-$, $CF_3-$, $CF_3CF_2-$, and $CF_3CH_2-$.

Examples of $Rf^{32}$ include $CH_3-$, $C_2H_5-$, $CF_3-$, $CF_3CF_2-$, $(CF_3)_2CH-$, $CF_3CH_2-$, $CF_3CH_2CH_2-$, $CF_3CFHCF_2CH_2-$, $C_2F_5CH_2-$, $CF_2HCF_2CH_2-$, $C_2F_5CH_2CH_2-$, $CF_3CF_2CH_2-$, and $CF_3CF_2CF_2CH_2-$. In order to achieve good miscibility with other solvents, particularly preferred are $CH_3-$, $C_2H_5-$, $CF_3CH_2-$, and $CF_3CH_2CH_2-$.

Specific examples of the fluorinated acyclic ester include one or two or more of $CF_3CH_2C(=O)OCH_3$, $HCF_2C(=O)OCH_3$, $CF_3C(=O)OCH_2CH_2CF_3$, $CF_3C(=O)OCH_2C_2F_5$, $CF_3C(=O)OCH_2CF_2CF_2H$, $CF_3C(=O)OCH_2CF_3$, and $CF_3C(=O)OCH(CF_3)_2$. In order to achieve good miscibility with other solvents and to give good rate characteristics, particularly preferred among these are $CF_3CH_2C(=O)OCH_3$, $HCF_2C(=O))OCH_3$, $CF_3C(=O)OCH_2C_2F_5$, $CF_3C(=O)OCH_2CF_2CF_2H$, $CF_3C(=O)OCH_2CF_3$, $CF_3C(=O)OCH(CF_3)_2$, ethyl pentafluorobutyrate, methyl pentafluoropropionate, ethyl pentafluoropropionate, methyl pentafluoroisobutyrate, isopropyl trifluorobutyrate, ethyl trifluoroacetate, tert-butyl trifluoroacetate, n-butyl trifluoroacetate, 2,2,3,3-tetrafluoropropyl trifluoroacetate, methyl tetrafluoro-2-(methoxy)propionate, methyl difluoroacetate, ethyl difluoroacetate, 2,2-difluoroethyl acetate, 2,2,3,3-tetrafluoropropyl acetate, 2,2,2-trifluoroethyl acetate, 1H,1H-heptafluorobutyl acetate, methyl 4,4,4-trifluorobutyrate, ethyl 4,4,4-trifluorobutyrate, methyl 3,3,3-trifluoropropionate, ethyl 3,3,3-trifluoropropionate, 3,3,3-trifluoropropyl 3,3,3-trifluoropropionate, ethyl 3-(trifluoromethyl)butyrate, methyl 2,3,3,3-tetrafluoropropionate, butyl 2,2-difluoroacetate, methyl 2,2,3,3-tetrafluoropropionate, methyl 2-(trifluoromethyl)-3,3,3-trifluoropropionate, and methyl heptafluorobutyrate.

The fluorinated acyclic ester is preferably present in an amount of 5 to 90% by volume, more preferably 15 to 70% by volume, relative to the solvent.

The solvent may also contain at least one fluorinated carbonate selected from the group consisting of the fluorinated acyclic carbonate and the fluorinated cyclic carbonate and the fluorinated acyclic ester. An electrolyte solution containing a solvent of such a composition can suitably be used for electrochemical devices used at relatively high voltage.

The solvent, when containing the fluorinated carbonate and the fluorinated acyclic ester, preferably contains 10 to 100% by volume in total of the fluorinated carbonate and the fluorinated acyclic ester. The total amount is more preferably 20% by volume or more, still more preferably 30% by volume or more, particularly preferably 40% by volume or more, while more preferably 95% by volume or less, still more preferably 90% by volume or less, particularly preferably 85% by volume or less.

For the solvent containing the fluorinated carbonate and the fluorinated acyclic ester, the fluorinated carbonate and the fluorinated acyclic ester preferably give a volume ratio of 5/95 to 95/5, more preferably 10/90 or higher, still more preferably 20/80 or higher, particularly preferably 30/70 or higher, while more preferably 90/10 or lower.

The solvent preferably consists only of a compound containing no fluorine atom (non-fluorinated solvent).

The solvent is preferably a non-aqueous solvent and the electrolyte solution of the invention is preferably a non-aqueous electrolyte solution.

The electrolyte solution of the invention may further contain a compound (5) represented by the following formula (5).

The formula (5) is as follows:

[Chem. 46]

$$A^{a+}_{p} \left[ (L^{201})_{n201}-Z^{201} \underset{Y^{202}}{\overset{Y^{201}}{\diagup \diagdown}} \begin{pmatrix} O \\ \diagdown \\ (X^{201})_{n202} \\ \diagup \\ O \end{pmatrix}_{n203} \right]^{b-}$$

wherein $A^{a+}$ is a metal ion, a hydrogen ion, or an onium ion;

a is an integer of 1 to 3;

b is an integer of 1 to 3;

p is b/a;

$n^{203}$ is an integer of 1 to 4;

$n^{201}$ is an integer of 0 to 8;

$n^{202}$ is 0 or 1;

$Z^{201}$ is a transition metal or an element in group III, group IV, or group V of the Periodic Table;

$X^{201}$ is O, S, a C1-C10 alkylene group, a C1-C10 halogenated alkylene group, a C6-C20 arylene group, or a C6-C20 halogenated arylene group, with the alkylene group, the halogenated alkylene group, the arylene group, and the halogenated arylene group each optionally containing a substituent and/or a hetero atom in the structure thereof, and when $n^{202}$ is 1 and $n^{203}$ is 2 to 4, $n^{203}$ $X^{201}$s optionally bind to each other;

$L^{201}$ is a halogen atom, a cyano group, a C1-C10 alkyl group, a C1-C10 halogenated alkyl group, a C6-C20 aryl group, a C6-C20 halogenated aryl group, or $-Z^{203}Y^{203}$, with the alkylene group, the halogenated alkylene group, the arylene group, and the halogenated arylene group each optionally containing a substituent and/or a hetero atom in the structure thereof, and when $n^{201}$ is 2 to 8, $n^{201}$ $L^{201}$s optionally bind to each other to form a ring;

$Y^{201}$, $Y^{202}$, and $Z^{203}$ are each individually O, S, $NY^{204}$, a hydrocarbon group, or a fluorinated hydrocarbon group;

$Y^{203}$ and $Y^{204}$ are each individually H, F, a C1-C10 alkyl group, a C1-C10 halogenated alkyl group, a C6-C20 aryl group, or a C6-C20 halogenated aryl group, with the alkyl group, the halogenated alkyl group, the aryl group, and the halogenated aryl group each optionally containing a substituent and/or a hetero atom in the structure thereof, and when multiple $Y^{203}$s or multiple $Y^{204}$s are present, they optionally bind to each other to form a ring.

Examples of $A^{a+}$ include a lithium ion, a sodium ion, a potassium ion, a magnesium ion, a calcium ion, a barium ion, a caesium ion, a silver ion, a zinc ion, a copper ion, a cobalt ion, an iron ion, a nickel ion, a manganese ion, a titanium ion, a lead ion, a chromium ion, a vanadium ion, a ruthenium ion, an yttrium ion, lanthanoid ions, actinoid ions, a tetrabutyl ammonium ion, a tetraethyl ammonium ion, a tetramethyl ammonium ion, a triethyl methyl ammonium ion, a triethyl ammonium ion, a pyridinium ion, an imidazolium ion, a hydrogen ion, a tetraethyl phosphonium ion, a tetramethyl phosphonium ion, a tetraphenyl phosphonium ion, a triphenyl sulfonium ion, and a triethyl sulfonium ion.

In applications such as electrochemical devices, $A^{a+}$ is preferably a lithium ion, a sodium ion, a magnesium ion, a tetraalkyl ammonium ion, or a hydrogen ion, particularly preferably a lithium ion. The valence a of the cation $A^{a+}$ is an integer of 1 to 3. If the valence a is greater than 3, the crystal lattice energy is high and the compound (5) has difficulty in dissolving in a solvent. Thus, the valence a is more preferably 1 when good solubility is needed. The valence b of the anion is also an integer of 1 to 3, particularly preferably 1. The constant p that represents the ratio between the cation and the anion is naturally defined by the ratio b/a between the valences thereof.

Next, ligands in the formula (5) are described. The ligands herein mean organic or inorganic groups binding to $Z^{201}$ in the formula (5).

$Z^{201}$ is preferably Al, B, V, Ti, Si, Zr, Ge, Sn, Cu, Y, Zn, Ga, Nb, Ta, Bi, P, As, Sc, Hf, or Sb, more preferably Al, B, or P.

$X^{201}$ is O, S, a C1-C10 alkylene group, a C1-C10 halogenated alkylene group, a C6-C20 arylene group, or a C6-C20 halogenated arylene group. These alkylene groups and arylene groups each may have a substituent and/or a hetero atom in the structure. Specifically, instead of a hydrogen atom in the alkylene group or the arylene group, the structure may have a halogen atom, a linear or cyclic alkyl group, an aryl group, an alkenyl group, an alkoxy group, an aryloxy group, a sulfonyl group, an amino group, a cyano group, a carbonyl group, an acyl group, an amide group, or a hydroxy group as a substituent; or, instead of a carbon atom in the alkylene or the arylene, the structure may have nitrogen, sulfur, or oxygen introduced therein. When $n^{202}$ is 1 and $n^{203}$ is 2 to 4, $n^{203}$ $X^{201}$s may bind to each other. One such example is a ligand such as ethylenediaminetetraacetic acid.

$L^{201}$ is a halogen atom, a cyano group, a C1-C10 alkyl group, a C1-C10 halogenated alkyl group, a C6-C20 aryl group, a C6-C20 halogenated aryl group, or —$Z^{203}Y^{203}$ ($Z^{203}$ and $Y^{203}$ will be described later). Similar to $X^{20}$, the alkyl groups and the aryl groups each may have a substituent and/or a hetero atom in the structure, and when $n^{201}$ is 2 to 8, $n^{201}$ $L^{201}$s optionally bind to each other to form a ring.

$L^{201}$ is preferably a fluorine atom or a cyano group. This is because a fluorine atom can improve the solubility and the degree of dissociation of a salt of an anion compound, thereby improving the ion conductivity. This is also because a fluorine atom can improve the oxidation resistance, reducing occurrence of side reactions.

$Y^{201}$, $Y^{202}$, and $Z^{203}$ are each individually O, S, $NY^{204}$, a hydrocarbon group, or a fluorinated hydrocarbon group. $Y^{201}$ and $Y^{202}$ are each preferably O, S, or $NY^{204}$, more preferably O. The compound (5) characteristically has a bond between $Y^{201}$ and $Z^{201}$ and a bond between $Y^{202}$ and $Z^{201}$ in the same ligand. Such a ligand forms a chelate structure with $Z^{201}$. This chelate has an effect of improving the heat resistance, the chemical stability, and the hydrolysis resistance of this compound. The constant n20² of the ligand is 0 or 1. In particular, $n^{22}$ is preferably 0 because the chelate ring becomes a five-membered ring, leading to the most strongly exerted chelate effect and improved stability.

The term "fluorinated hydrocarbon group" herein means a group obtainable by replacing at least one hydrogen atom of a hydrocarbon group by a fluorine atom.

$Y^{203}$ and $Y^{204}$ are each individually H, F, a C1-C10 alkyl group, a C1-C10 halogenated alkyl group, a C6-C20 aryl group, or a C6-C20 halogenated aryl group. These alkyl groups and aryl groups each may contain a substituent or a hetero atom in the structure. When multiple $Y^{203}$s or multiple $Y^{204}$s are present, they optionally bind to each other to form a ring.

The constant $n^{203}$ relating to the number of the aforementioned ligands is an integer of 1 to 4, preferably 1 or 2, more preferably 2. The constant $n^{201}$ relating to the number of the aforementioned ligands is an integer of 0 to 8, preferably an integer of 0 to 4, more preferably 0, 2, or 4. In addition, when $n^{203}$ is 1, $n^{201}$ is preferably 2; and when $n^{203}$ is 2, $n^{201}$ is preferably 0.

In the formula (5), the alkyl group, the halogenated alkyl group, the aryl group, and the halogenated aryl group include those having any other functional groups such as branches, hydroxy groups, and ether bonds.

The compound (5) is preferably a compound represented by the following formula:

[Chem. 47]

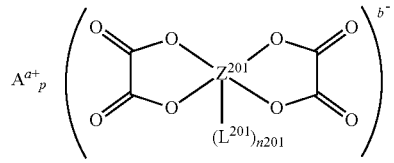

(wherein $A^{a+}$, a, b, p, $n^{201}$, $Z^{201}$, and $L^{201}$ are defined as described above), or a compound represented by the following formula:

[Chem. 48]

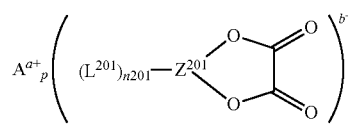

(wherein $A^{a+}$, a, b, p, $n^{201}$, $Z^{201}$, and $L^{201}$ are defined as described above).

The compound (5) may be a lithium oxalatoborate salt. Examples thereof include lithium bis(oxalato)borate (Li-BOB) represented by the following formula:

[Chem. 49]

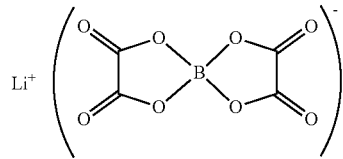

and lithium difluorooxalatoborate (LiDFOB) represented by the following formula:

[Chem. 50]

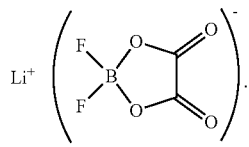

Examples of the compound (5) also include
lithium difluorooxalatophosphanite (LiDFOP) represented by the following formula:

[Chem.51]

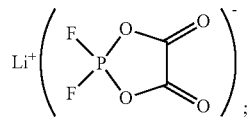

lithium tetrafluorooxalatophosphanite (LITFOP) represented by the following formula:

[Chem. 52]

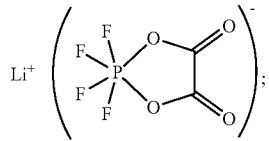

and
lithium bis(oxalato)difluorophosphanite represented by the following formula:

[Chem. 53]

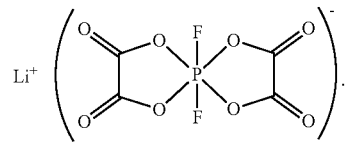

In addition, specific examples of dicarboxylic acid complex salts containing boron as a comlex center element include lithium bis(malonato)borate, lithium difluoro(malonato)borate, lithium bis(methylmalonato)borate, lithium difluoro(methylmalonato)borate, lithium bis(dimethylmalonato)borate, and lithium difluoro(dimethylmalonato)borate.

Specific examples of dicarboxylic acid complex salts contianing phosphorus as a complex center element include lithium tris(oxalato)phosphate, lithium tris(malonato)phosphate, lithium difluorobis(malonato)phosphate, lithium tetrafluoro(malonato)phosphate, lithium tris(methylmalonato) phosphate, lithium difluorobis(methylmalonato)phosphate, lithium tetrafluoro(methylmalonato)phosphate, lithium tris (dimethylmalonato)phosphate, lithium difluorobis(dimethylmalonato)phosphate, and lithium tetrafluoro(dimethylmalonato)phosphate.

Specific examples of dicarboxylic acid complex salts containing aluminum as a complex center element include $LiAl(C_2O_4)_2$ and $LiAlF_2 (C_2O_4)$.

In order to enable easy availability and contribute to formation of a stable film-shaped structure, more preferred among these are lithium bis(oxalato)borate, lithium difluoro (oxalato)borate, lithium tris(oxalato)phosphate, lithium difluorobis(oxalato)phosphate, and lithium tetrafluoro(oxalato) phosphate.

In order to give much better cycle characteristics, the compound (5) is preferably in an amount of 0.001% by mass or more, more preferably 0.01% by mass or more, while preferably 10% by mass or less, more preferably 3% by mass or less, relative to the solvent.

The electrolyte solution of the invention preferably further contains an electrolyte salt other than the compound (5) and $LiPF_6$. Examples of the electrolyte salt used include any of those to be used for electrolyte solutions for a lithium ion secondary battery.

The electrolyte salt is preferably a lithium salt other than the compound (5) and $LiPF_6$.

Any lithium salt may be used. Specific examples thereof include the following:

inorganic lithium salts such as $LiBF_4$, $LiClO_4$, $LiAlF_4$, $LiSbF_6$, $LiTaF_6$, $LiWF_7$, $LiAsF_6$, $LiAlCl_4$, LiI, LiBr, LiCl, $LiB_{10}Cl_{10}$, $Li_2SiF_6$, $Li_2PFO_3$, and $LiPO_2F_2$;

lithium tungstates such as $LiWOFs$;

lithium carboxylates such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$, and $CF_3CF_2CF_2CF_2CO_2Li$;

lithium salts containing an S=O group such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$, $CF_3CF_2CF_2CF_2SO_3Li$, lithium methylsulfate, lithium ethylsulfate, and lithium 2,2,2-trifluoroethylsulfate;

lithium imide salts such as $LiN(FCO)_2$, $LiN(FCO)(FSO_2)$, $LiN(FSO_2)_2$, $LiN(FSO_2)(CF_3SO_2)$, $LiN(CF_3SO_2)_2$, $LiN(C_2F_5SO_2)_2$, lithium bis-perfluoroethanesulfonyl imide, lithium cyclic 1,2-perfluoroethanedisulfonyl imide, lithium cyclic 1,3-perfluoropropanedisulfonyl imide, lithium cyclic 1,2-ethanedisulfonyl imide, lithium cyclic 1,3-propanedisulfonyl imide, lithium cyclic 1,4-perfluorobutanedisulfonyl imide, $LiN(CF_3SO_2) (FSO_2)$, $LiN(CF_3SO_2) (C_3F_7SO_2)$ r, $LiN(CF_3SO_2) (C_4F_9SO_2)$, and $LiN(POF_2)_2$;

lithium methide salts such as $LiC(FSO_2)_3$, $LiC(CF_3SO_2)_3$, and $LiC(C_2F_5SO_2)_3$; and fluorine-containing organic lithium salts such as salts represented by the formula: $LiPF_a(C_nF_{2n+1})_{6-a}$ (wherein a is an integer of 0 to 5; and n is an integer of 1 to 6) such as $LiPF_3(C_2F_5)_3$, $LiPF_3(CF_3)_3$, $LiPF_3(iso-C_3F_7)_3$, $LiPF_5(iso-C_3F_7)$, $LiPF_4(CF_3)_2$, and $LiPF_4(C_2F_5)_2$, as well as $LiPF_4 (CF_3SO_2)_2$, $LiPF_4 (C_2FsSO_2)_2$, $LiBF_3CF_3$, $LiBF_3C_2F_5$, $LiBF_3C_3F_7$, $LiBF_2 (CF_3)_2$, $LiBF_2(C_2F_5)_2$, $LiBF_2(CF_3SO_2)_2$, and LiBF$_2$(C$_2$F$_5$SO$_2$)$_2$, and LiSCN, LiB(CN)$_4$, LiB(C$_6$H$_5$)$_4$, Li$_2$(C$_2$O$_4$), LiP(C$_2$O$_4$)$_3$, and Li$_2$B$_{12}$F$_b$H$_{12-b}$ (wherein b is an integer of 0 to 3).

In order to achieve an effect of improving properties such as output characteristics, high-rate charge and discharge characteristics, high-temperature storage characteristics, and cycle characteristics, particularly preferred among these are LiBF$_4$, LiSbF$_6$, LiTaF$_6$, LiPO$_2$F$_2$, FSO$_3$Li, CF$_3$SO$_3$Li, LiN(FSO$_2$)$_2$, LiN(FSO$_2$)(CF$_3$SO$_2$), LiN(CF$_3$SO$_2$)$_2$, LiN(C$_2$F$_5$SO$_2$)$_2$, lithium cyclic 1,2-perfluoroethanedisulfonyl imide, lithium cyclic 1,3-perfluoropropanedisulfonyl imide, LiC(FSO$_2$)$_3$, LiC(CF$_3$SO$_2$)$_3$, LiC(C$_2$F$_5$SO$_2$)$_3$, LiBF$_3$CF$_3$, LiBF$_3$C$_2$F$_5$, LiPF$_3$(CF$_3$)$_3$, LiPF$_3$(C$_2$F$_5$)$_3$, and the like.

These electrolyte salts may be used alone or in combination of two or more. Any combination use of LiPF$_6$ and LiBF$_4$, FSO$_3$Li, LiPO$_2$F$_2$, or the like is also preferred because these combinations have an effect of improving the load characteristics and the cycle characteristics.

In this case, LiBF$_4$, FSO$_3$Li, or LiPO$_2$F$_2$ may be present in any amount that does not significantly impair the effects of the invention in 100% by mass of the whole electrolyte solution. The amount thereof is usually 0.01% by mass or more, preferably 0.1% by mass or more, while the upper limit thereof is usually 30% by mass or less, preferably 20% by mass or less, relative to the electrolyte solution of the invention.

In another example, an inorganic lithium salt and an organic lithium salt are used in combination. Such a combination has an effect of reducing deterioration due to high-temperature storage. The organic lithium salt is preferably CF$_3$SO$_3$Li, LiN(FSO$_2$)$_2$, LiN(FSO$_2$)(CF$_3$SO$_2$), LiN(CF$_3$SO$_2$)$_2$, LiN(C$_2$F$_5$SO$_2$)$_2$, lithium cyclic 1,2-perfluoroethanedisulfonyl imide, lithium cyclic 1,3-perfluoropropanedisulfonyl imide, LiC(FSO$_2$)$_3$, LiC(CF$_3$SO$_2$)$_3$, LiC(C$_2$F$_5$SO$_2$)$_3$, LiBF$_3$CF$_3$, LiBF$_3$C$_2$F$_5$, LiPF$_3$(CF$_3$)$_3$, LiPF$_3$(C$_2$F$_5$)$_3$, or the like. In this case, the proportion of the organic lithium salt is preferably 0.1% by mass or more, particularly preferably 0.5% by mass or more, while preferably 30% by mass or less, particularly preferably 20% by mass or less, of 100% by mass of the whole electrolyte solution.

The electrolyte salt in the electrolyte solution may have any concentration that does not impair the effects of the invention. In order to make the electric conductivity of the electrolyte solution within a favorable range and to ensure good battery performance, the lithium in the electrolyte solution preferably has a total mole concentration of 0.3 mol/L or higher, more preferably 0.4 mol/L or higher, still more preferably 0.5 mol/L or higher, while preferably 3 mol/L or lower, more preferably 2.5 mol/L or lower, still more preferably 2.0 mol/L or lower.

Too low a total mole concentration of lithium may cause insufficient electric conductivity of the electrolyte solution, while too high a concentration may cause an increase in viscosity and then reduction in electric conductivity, impairing the battery performance.

The electrolyte solution of the invention preferably further contains a compound (2) represented by the following formula (2):

[Chem. 54]

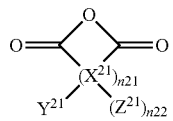

(wherein $X^{21}$ is a group containing at least H or C; $n^{21}$ is an integer of 1 to 3; $Y^{21}$ and $Z^{21}$ are the same as or different from each other, and are each a group containing at least H, C, O, or F; $n^{22}$ is 0 or 1; and $Y^{21}$ and $Z^{21}$ optionally bind to each other to form a ring). The electrolyte solution containing the compound (2) can cause much less reduction in capacity retention and can cause a much less increase in amount of gas generated even when stored at high temperature.

When $n^{21}$ is 2 or 3, the two or three $X^{21}$s may be the same as or different from each other.

When multiple Y21s and multiple Z21s are present, the multiple Y21s may be the same as or different from each other and the multiple Z21s may be the same as or different from each other.

$X^{21}$ is preferably a group represented by —$CY^{21}Z^{21}$— (wherein $Y^{21}$ and $Z^{21}$ are defined as described above) or a group represented by —$CY^{21}$=$CZ^{21}$— (wherein $Y^{21}$ and $Z^{21}$ are defined as described above).

$Y^{21}$ preferably includes at least one selected from the group consisting of H—, F—, CH$_3$—, CH$_3$CH$_2$—, CH$_3$CH$_2$CH$_2$—, CF$_3$—, CF$_3$CF$_2$—, CH$_2$FCH$_2$—, and CF$_3$CF$_2$CF$_2$—.

$Z^{21}$ preferably includes at least one selected from the group consisting of H—, F—, CH$_3$—, CH$_3$CH$_2$—, CH$_3$CH$_2$CH$_2$—, CF$_3$—, CF$_3$CF$_2$—, CH$_2$FCH$_2$—, and CF$_3$CF$_2$CF$_2$—.

Alternatively, $Y^{21}$ and $Z^{21}$ may bind to each other to form a carbon ring or heterocycle that may contain an unsaturated bond and may have aromaticity. The ring preferably has a carbon number of 3 to 20.

Next, specific examples of the compound (2) are described. In the following examples, the term "analog" means an acid anhydride obtainable by replacing part of the structure of an acid anhydride mentioned as an example by another structure within the scope of the invention. Examples thereof include dimers, trimers, and tetramers each composed of a plurality of acid anhydrides, structural isomers such as those having a substituent that has the same carbon number but also has a branch, and those having a different site at which a substituent binds to the acid anhydride.

Specific examples of an acid anhydride having a 5-membered cyclic structure include succinic anhydride, methylsuccinic anhydride (4-methylsuccinic anhydride), dimethylsuccinic anhydride (e.g., 4,4-dimethylsuccinic anhydride, 4,5-dimethylsuccinic anhydride), 4,4,5-trimethylsuccinic anhydride, 4,4,5,5-tetramethylsuccinic anhydride, 4-vinylsuccinic anhydride, 4,5-divinylsuccinic anhydride, phenylsuccinic anhydride (4-phenylsuccinic anhydride), 4,5-diphenylsuccinic anhydride, 4,4-diphenylsuccinic anhydride, citraconic anhydride, maleic anhydride, methylmaleic anhydride (4-methylmaleic anhydride), 4,5-dimethylmaleic anhydride, phenylmaleic anhydride (4-phenylmaleic anhydride), 4,5-diphenylmaleic anhydride, itaconic anhydride, 5-methylitaconic anhydride, 5,5-dimethylitaconic anhydride, phthalic anhydride, and 3,4,5,6-tetrahydrophthalic anhydride, and analogs thereof.

Specific examples of an acid anhydride having a 6-membered cyclic structure include cyclohexanedicarboxylic anhydride (e.g., cyclohexane-1,2-dicarboxylic anhydride), 4-cyclohexene-1,2-dicarboxylic anhydride, glutaric anhydride, glutaconic anhydride, and 2-phenylglutaric anhydride, and analogs thereof.

Specific examples of an acid anhydride having a different cyclic structure include 5-norbornene-2,3-dicarboxylic anhydride, cyclopentanetetracarboxylic dianhydride, pyromellitic anhydride, and diglycolic anhydride, and analogs thereof.

Specific examples of an acid anhydride having a cyclic structure and substituted with a halogen atom include monofluorosuccinic anhydride (e.g., 4-fluorosuccinic anhydride), 4,4-difluorosuccinic anhydride, 4,5-difluorosuccinic anhydride, 4,4,5-trifluorosuccinic anhydride, trifluoromethylsuccinic anhydride, tetrafluorosuccinic anhydride (4,4,5,5-tetrafluorosuccinic anhydride), 4-fluoromaleic anhydride, 4,5-difluoromaleic anhydride, trifluoromethylmaleic anhydride, 5-fluoroitaconic anhydride, and 5,5-difluoroitaconic anhydride, and analogs thereof.

Preferred among these as the compound (2) are glutaric anhydride, citraconic anhydride, glutaconic anhydride, itaconic anhydride, diglycolic anhydride, cyclohexanedicarboxylic anhydride, cyclopentanetetracarboxylic dianhydride, 4-cyclohexene-1,2-dicarboxylic anhydride, 3,4,5,6-tetrahydrophthalic anhydride, 5-norbornene-2,3-dicarboxylic anhydride, phenylsuccinic anhydride, 2-phenylglutaric anhydride, maleic anhydride, methylmaleic anhydride, trifluoromethylmaleic anhydride, phenylmaleic anhydride, succinic anhydride, methylsuccinic anhydride, dimethylsuccinic anhydride, trifluoromethylsuccinic anhydride, monofluorosuccinic anhydride, and tetrafluorosuccinic anhydride. More preferred are maleic anhydride, methylmaleic anhydride, trifluoromethylmaleic anhydride, succinic anhydride, methylsuccinic anhydride, trifluoromethylsuccinic anhydride, and tetrafluorosuccinic anhydride. Still more preferred are maleic anhydride and succinic anhydride.

The compound (2) preferably includes at least one selected from the group consisting of: a compound (3) represented by the following formula (3):

[Chem. 55]

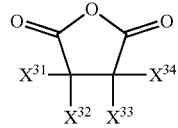

(wherein $X^{31}$ to $X^{34}$ are the same as or different from each other, and are each a group containing at least H, C, O, or F); and a compound (4) represented by the following formula

[Chem. 56]

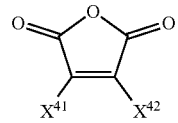

(wherein $X^{41}$ and $X^{42}$ are the same as or different from each other, and are each a group containing at least H, C, O, or F).

$X^{31}$ to $X^{34}$ are the same as or different from each other, and preferably include at least one selected from the group consisting of an alkyl group, a fluorinated alkyl group, an alkenyl group, and a fluorinated alkenyl group. $X^{31}$ to $X^{34}$ each preferably have a carbon number of 1 to 10, more preferably 1 to 3.

$X^{31}$ to $X^{34}$ are the same as or different from each other, and more preferably include at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

$X^{41}$ and $X^{42}$ are the same as or different from each other, and preferably include at least one selected from the group consisting of an alkyl group, a fluorinated alkyl group, an alkenyl group, and a fluorinated alkenyl group. $X^{41}$ and $X^{42}$ each preferably have a carbon number of 1 to 10, more preferably 1 to 3.

$X^{41}$ and $X^{42}$ are the same as or different from each other, and more preferably include at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

The compound (3) is preferably any of the following compounds.

[Chem. 57]

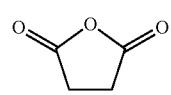

[Chem. 58]

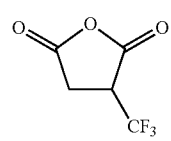

[Chem. 59]

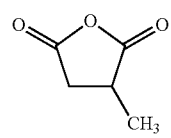

[Chem. 60]

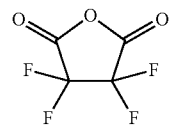

The compound (4) is preferably any of the following compounds.

[Chem. 61]

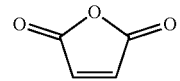

[Chem. 62]

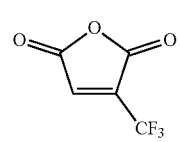

[Chem. 63]

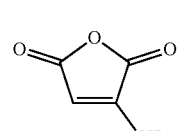

In order to cause much less reduction in capacity retention and a much less increase in amount of gas generated even when stored at high temperature, the electrolyte solution preferably contains 0.0001 to 15% by mass of the compound (2) relative to the electrolyte solution. The amount of the compound (2) is more preferably 0.01 to 10% by mass, still more preferably 0.1 to 3% by mass, particularly preferably 0.1 to 1.0% by mass.

In order to cause much less reduction in capacity retention and a much less increase in amount of gas generated even when stored at high temperature, the electrolyte solution, when containing both the compounds (3) and (4), preferably contains 0.08 to 2.50% by mass of the compound (3) and 0.02 to 1.50% by mass of the compound (4), more preferably 0.80 to 2.50% by mass of the compound (3) and 0.08 to 1.50% by mass of the compound (4), relative to the electrolyte solution.

The electrolyte solution of the invention may contain at least one selected from the group consisting of nitrile compounds represented by the following formulae (1a), (1b), and (1c):

[Chem. 64]

(1a)

(wherein $R^a$ and $R^b$ are each individually a hydrogen atom, a cyano group (CN), a halogen atom, an alkyl group, or a group obtainable by replacing at least one hydrogen atom of an alkyl group by a halogen atom; and n is an integer of 1 to 10);

[Chem. 65]

(1b)

(wherein $R^c$ is a hydrogen atom, a halogen atom, an alkyl group, a group obtainable by replacing at least one hydrogen atom of an alkyl group by a halogen atom, or a group represented by NC—$R^{c1}$—$X^{c1}$— (wherein $R^{c1}$ is an alkylene group, $X^{c1}$ is an oxygen atom or a sulfur atom); $R^d$ and $R^e$ are each individually a hydrogen atom, a halogen atom, an alkyl group, or a group obtainable by replacing at least one hydrogen atom of an alkyl group by a halogen atom; and m is an integer of 1 to 10);

[Chem. 66]

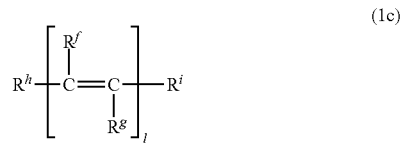

(1c)

(wherein $R^f$, $R^g$, $R^h$, and $R^i$ are each individually a group containing a cyano group (CN), a hydrogen atom (H), a halogen atom, an alkyl group, or a group obtainable by replacing at least one hydrogen atom of an alkyl group by a halogen atom; at least one selected from $R^f$, $R^g$, $R^h$, and $R^i$ is a group containing a cyano group; and l is an integer of 1 to 3).

This can improve the high-temperature storage characteristics of an electrochemical device. One nitrile compound may be used alone, or two or more thereof may be used in any combination at any ratio.

In the formula (1a), $R^a$ and $R^b$ are each individually a hydrogen atom, a cyano group (CN), a halogen atom, an alkyl group, or a group obtainable by replacing at least one hydrogen atom of an alkyl group by a halogen atom.

Examples of the halogen atom include a fluorine atom, a chlorine atom, a bromine atom, and an iodine atom. Preferred among these is a fluorine atom.

The alkyl group is preferably a C1-C5 alkyl group. Specific examples of the alkyl group include a methyl group, an ethyl group, a propyl group, an isopropyl group, a butyl group, an isobutyl group, and a tert-butyl group.

An example of the group obtainable by replacing at least one hydrogen atom of an alkyl group by a halogen atom is a group obtainable by replacing at least one hydrogen atom of the aforementioned alkyl group by the aforementioned halogen atom.

When $R^a$ and $R^b$ are alkyl groups or groups each obtainable by replacing at least one hydrogen atom of an alkyl group by a halogen atom, $R^a$ and $R^b$ may bind to each other to form a cyclic structure (e.g., a cyclohexane ring).

$R^a$ and $R^b$ are each preferably a hydrogen atom or an alkyl group.

In the formula (1a), n is an integer of 1 to 10. When n is 2 or greater, all of n $R^a$s may be the same as each other, or at least part of them may be different from the others. The same applies to $R^b$. In the formula, n is preferably an integer of 1 to 7, more preferably an integer of 2 to 5.

Preferred as the nitrile compound represented by the formula (1a) are dinitriles and tricarbonitriles.

Specific examples of the dinitriles include malononitrile, succinonitrile, glutaronitrile, adiponitrile, pimelonitrile, suberonitrile, azelanitrile, sebaconitrile, undecanedinitrile, dodecanedinitrile, methylmalononitrile, ethylmalononitrile, isopropylmalononitrile, tert-butylmalononitrile, methylsuccinonitrile, 2,2-dimethylsuccinonitrile, 2,3-dimethylsuccinonitrile, 2,3,3-trimethylsuccinonitrile, 2,2,3,3-tetramethylsuccinonitrile, 2,3-diethyl-2,3-dimethylsuccinonitrile, 2,2-diethyl-3,3-dimethylsuccinonitrile, bicyclohexyl-1,1-dicarbonitrile, bicyclohexyl-2,2-dicarbonitrile, bicyclohexyl-3,3-dicarbonitrile, 2,5-dimethyl-2,5-hexanedicarbonitrile, 2,3-diisobutyl-2,3-dimethylsuccinonitrile, 2,2-diisobutyl-3,3-dimethylsuccinonitrile, 2-methylglutaronitrile, 2,3-dimethylglutaronitrile, 2,4-dimethylglutaronitrile, 2,2,3,3-tetramethylglutaronitrile, 2,2,4,4-tetramethylglutaronitrile, 2,2,3,4-tetramethylglutaronitrile, 2,3,3,4-tetramethylglutaronitrile, 1,4-dicyanopentane, 2,6-dicyanoheptane, 2,7-dicyanooctane, 2,8-dicyanononane, 1,6-dicyanodecane, 1,2-dicyanobenzene, 1,3-dicyanobenzene, 1,4-dicyanobenzene, 3,3'-(ethylenedioxy)dipropionitrile, 3,3'-(ethylenedithio)dipropionitrile, 3,9-bis(2-cyanoethyl)-2,4,8,10-tetraoxaspiro[5,5]undecane, butanenitrile, and phthalonitrile. Particularly preferred among these are succinonitrile, glutaronitrile, and adiponitrile, and most preferred is adiponitrile.

Specific examples of the tricarbonitriles include pentanetricarbonitrile, propanetricarbonitrile, 1,3,5-hexanetricarbonitrile, 1,3,6-hexanetricarbonitrile, heptanetricarbonitrile, 1,2,3-propanetricarbonitrile, 1,3,5-pentanetricarbonitrile, cyclohexanetricarbonitrile, triscyanoethylamine, triscyanoethoxypropane, tricyanoethylene, and tris(2-cyanoethyl)

amine. Particularly preferred are 1,3,6-hexanetricarbonitrile and cyclohexanetricarbonitrile, and most preferred is cyclohexanetricarbonitrile.

In the formula (1b), $R^c$ is a hydrogen atom, a halogen atom, an alkyl group, a group obtainable by replacing at least one hydrogen atom of an alkyl group by a halogen atom, or a group represented by NC—$R^{c1}$—$X^{c1}$— (wherein $R^{c1}$ is an alkylene group; and $X^{c1}$ is an oxygen atom or a sulfur atom); $R^d$ and $R^e$ are each individually a hydrogen atom, a halogen atom, an alkyl group, or a group obtainable by replacing at least one hydrogen atom of an alkyl group by a halogen atom.

Examples of the halogen atom, the alkyl group, and the group obtainable by replacing at least one hydrogen atom of an alkyl group by a halogen atom include those mentioned as examples thereof for the formula (1a).

$R^{c1}$ in NC—$R^{c1}$—$X^{c1}$— is an alkylene group. The alkylene group is preferably a C1-C3 alkylene group.

$R^c$, $R^d$, and $R^e$ are each preferably individually a hydrogen atom, a halogen atom, an alkyl group, or a group obtainable by replacing at least one hydrogen atom of an alkyl group by a halogen atom.

At least one selected from $R^c$, $R^d$, and $R^e$ is preferably a halogen atom or a group obtainable by replacing at least one hydrogen atom of an alkyl group by a halogen atom, more preferably a fluorine atom or a group obtainable by replacing at least one hydrogen atom of an alkyl group by a fluorine atom.

When $R^d$ and $R^e$ are each an alkyl group or a group obtainable by replacing at least one hydrogen atom of an alkyl group by a halogen atom, $R^d$ and $R^e$ may bind to each other to form a cyclic structure (e.g., a cyclohexane ring).

In the formula (1b), m is an integer of 1 to 10. When m is 2 or greater, all of m $R^d$s may be the same as each other, or at least part of them may be different from the others. The same applies to $R^e$. In the formula, m is preferably an integer of 2 to 7, more preferably an integer of 2 to 5.

Examples of the nitrile compound represented by the formula (1b) include acetonitrile, propionitrile, butyronitrile, isobutyronitrile, valeronitrile, isovaleronitrile, lauronitrile, 3-methoxypropionitrile, 2-methylbutyronitrile, trimethylacetonitrile, hexanenitrile, cyclopentanecarbonitrile, cyclohexanecarbonitrile, fluoroacetonitrile, difluoroacetonitrile, trifluoroacetonitrile, 2-fluoropropionitrile, 3-fluoropropionitrile, 2,2-difluoropropionitrile, 2,3-difluoropropionitrile, 3,3-difluoropropionitrile, 2,2,3-trifluoropropionitrile, 3,3,3-trifluoropropionitrile, 3,3'-oxydipropionitrile, 3,3'-thiodipropionitrile, pentafluoropropionitrile, methoxyacetonitrile, and benzonitrile. Particularly preferred among these is 3,3,3-trifluoropropionitrile.

In the formula (1c), $R^f$, $R^g$, $R^h$, and $R^i$ are each individually a group containing a cyano group (CN), a hydrogen atom, a halogen atom, an alkyl group, or a group obtainable by replacing at least one hydrogen atom of an alkyl group by a halogen atom.

Examples of the halogen atom, the alkyl group, and the group obtainable by replacing at least one hydrogen atom of an alkyl group by a halogen atom include those mentioned as examples thereof for the formula (1a).

Examples of the group containing a cyano group include a cyano group and a group obtainable by replacing at least one hydrogen atom of an alkyl group by a cyano group. Examples of the alkyl group in this case include those mentioned as examples for the formula (1a).

At least one selected from $R^f$, $R^g$, $R^h$, and $R^i$ is a group containing a cyano group. Preferably, at least two selected from $R^f$, $R^g$, $R^h$, and $R^i$ are each a group containing a cyano group. More preferably, $R^h$ and $R^i$ are each a group containing a cyano group. When $R^h$ and $R^i$ are each a group containing a cyano group, $R^f$ and $R^g$ are preferably hydrogen atoms.

In the formula (1c), 1 is an integer of 1 to 3. When 1 is 2 or greater, all of 1 $R^f$s may be the same as each other, or at least part of them may be different from the others. The same applies to $R^g$. In the formula, 1 is preferably an integer of 1 or 2.

Examples of the nitrile compound represented by the formula (1c) include 3-hexenedinitrile, mucononitrile, maleonitrile, fumaronitrile, acrylonitrile, methacrylonitrile, crotononitrile, 3-methylcrotononitrile, 2-methyl-2-butenenitrile, 2-pentenenitrile, 2-methyl-2-pentenenitrile, 3-methyl-2-pentenenitrile, and 2-hexenenitrile. Preferred are 3-hexenedinitrile and mucononitrile, particularly preferred is 3-hexenedinitrile.

The nitrile compounds are preferably present in an amount of 0.2 to 7% by mass relative to the electrolyte solution. This can further improve the high-temperature storage characteristics and safety of an electrochemical device at high voltage. The lower limit of the total amount of the nitrile compounds is more preferably 0.3% by mass, still more preferably 0.5% by mass. The upper limit thereof is more preferably 5% by mass, still more preferably 2% by mass, particularly preferably 0.5% by mass.

The electrolyte solution of the invention may contain a compound containing an isocyanate group (hereinafter, also abbreviated as "isocyanate"). The isocyanate used may be any isocyanate. Examples of the isocyanate include monoisocyanates, diisocyanates, and triisocyanates.

Specific examples of the monoisocyanate include isocyanatomethane, isocyanatoethane, 1-isocyanatopropane, 1-isocyanatobutane, 1-isocyanatopentane, 1-isocyanatohexane, 1-isocyanatoheptane, 1-isocyanatooctane, 1-isocyanatononane, 1-isocyanatodecane, isocyanatocyclohexane, methoxycarbonyl isocyanate, ethoxycarbonyl isocyanate, propoxycarbonyl isocyanate, butoxycarbonyl isocyanate, methoxysulfonyl isocyanate, ethoxysulfonyl isocyanate, propoxysulfonyl isocyanate, butoxysulfonyl isocyanate, fluorosulfonyl isocyanate, methyl isocyanate, butyl isocyanate, phenyl isocyanate, 2-isocyanatoethyl acrylate, 2-isocyanatoethyl methacrylate, and ethyl isocyanate.

Specific examples of the diisocyanates include 1,4-diisocyanatobutane, 1,5-diisocyanatopentane, 1,6-diisocyanatohexane, 1,7-diisocyanatoheptane, 1,8-diisocyanatooctane, 1,9-diisocyanatononane, 1,10-diisocyanatodecane, 1,3-diisocyanatopropene, 1,4-diisocyanato-2-butene, 1,4-diisocyanato-2-fluorobutane, 1,4-diisocyanato-2,3-difluorobutane, 1,5-diisocyanato-2-pentene, 1,5-diisocyanato-2-methylpentane, 1,6-diisocyanato-2-hexene, 1,6-diisocyanato-3-hexene, 1,6-diisocyanato-3-fluorohexane, 1,6-diisocyanato-3,4-difluorohexane, toluene diisocyanate, xylene diisocyanate, tolylene diisocyanate, 1,2-bis(isocyanatomethyl)cyclohexane, 1,3-bis(isocyanatomethyl)cyclohexane, 1,4-bis(isocyanatomethyl)cyclohexane, 1,2-diisocyanatocyclohexane, 1,3-diisocyanatocyclohexane, 1,4-diisocyanatocyclohexane, dicyclohexylmethane-1,1'-diisocyanate, dicyclohexylmethane-2,2'-diisocyanate, dicyclohexylmethane-3,3'-diisocyanate, dicyclohexylmethane-4,4'-diisocyanate, isophorone diisocyanate, bicyclo[2.2.1]heptane-2,5-diylbis (methyl=isocyanate), bicyclo[2.2.1]heptane-2,6-diylbis (methyl=isocyanate), 2,4,4-trimethylhexamethylene diisocyanate, 2,2,4-trimethylhexamethylene diisocyanate, hexamethylene diisocyanate, 1,4-phenylene diisocyanate, octamethylene diisocyanate, and tetramethylene diisocyanate.

Specific examples of the triisocyanates include 1,6,11-triisocyanatoundecane, 4-isocyanatomethyl-1,8-octamethylene diisocyanate, 1,3,5-triisocyanatomethylbenzene, 1,3,5-tris(6-isocyanatohex-1-yl)-1,3,5-triazine-2,4,6(1H,3H,5H)-trione, and 4-(isocyanatomethyl) octamethylene=diisocyanate.

In order to enable industrially easy availability and cause low cost in production of an electrolyte solution, preferred among these are 1,6-diisocyanatohexane, 1,3-bis(isocyanatomethyl)cyclohexane, 1,3,5-tris(6-isocyanatohex-1-yl)-1,3,5-triazine-2,4,6(1H,3H,5H)-trione, 2,4,4-trimethylhexamethylene diisocyanate, and 2,2,4-trimethylhexamethylene diisocyanate. From the technical viewpoint, they can contribute to formation of a stable film-shaped structure and can therefore more suitably be used.

The isocyanate may be present in any amount that does not significantly impair the effects of the invention. The amount is preferably, but not limited to, 0.001% by mass or more and 1.0% by mass or less relative to the electrolyte solution. The isocyanate in an amount of not smaller than this lower limit can give a sufficient effect of improving the cycle characteristics to a non-aqueous electrolyte secondary battery. The isocyanate in an amount of not larger than this upper limit can eliminate an initial increase in resistance of a non-aqueous electrolyte secondary battery. The amount of the isocyanate is more preferably 0.01% by mass or more, still more preferably 0.1% by mass or more, particularly preferably 0.2% by mass or more, while more preferably 0.8% by mass or less, still more preferably 0.7% by mass or less, particularly preferably 0.6% by mass or less.

The electrolyte solution of the invention may contain a cyclic sulfonate. The cyclic sulfonate may be any cyclic sulfonate. Examples of the cyclic sulfonate include a saturated cyclic sulfonate, an unsaturated cyclic sulfonate, a saturated cyclic disulfonate, and an unsaturated cyclic disulfonate.

Specific examples of the saturated cyclic sulfonate include 1,3-propanesultone, 1-fluoro-1,3-propanesultone, 2-fluoro-1,3-propanesultone, 3-fluoro-1,3-propanesultone, 1-methyl-1,3-propanesultone, 2-methyl-1,3-propanesultone, 3-methyl-1,3-propanesultone, 1,3-butanesultone, 1,4-butanesultone, 1-fluoro-1,4-butanesultone, 2-fluoro-1,4-butanesultone, 3-fluoro-1,4-butanesultone, 4-fluoro-1,4-butanesultone, 1-methyl-1,4-butanesultone, 2-methyl-1,4-butanesultone, 3-methyl-1,4-butanesultone, 4-methyl-1,4-butanesultone, and 2,4-butanesultone.

Specific examples of the unsaturated cyclic sulfonate include 1-propene-1,3-sultone, 2-propene-1,3-sultone, 1-fluoro-1-propene-1,3-sultone, 2-fluoro-1-propene-1,3-sultone, 3-fluoro-1-propene-1,3-sultone, 1-fluoro-2-propene-1,3-sultone, 2-fluoro-2-propene-1,3-sultone, 3-fluoro-2-propene-1,3-sultone, 1-methyl-1-propene-1,3-sultone, 2-methyl-1-propene-1,3-sultone, 3-methyl-1-propene-1,3-sultone, 1-methyl-2-propene-1,3-sultone, 2-methyl-2-propene-1,3-sultone, 3-methyl-2-propene-1,3-sultone, 1-butene-1,4-sultone, 2-butene-1,4-sultone, 3-butene-1,4-sultone, 1-fluoro-1-butene-1,4-sultone, 2-fluoro-1-butene-1,4-sultone, 3-fluoro-1-butene-1,4-sultone, 4-fluoro-1-butene-1,4-sultone, 1-fluoro-2-butene-1,4-sultone, 2-fluoro-2-butene-1,4-sultone, 3-fluoro-2-butene-1,4-sultone, 4-fluoro-2-butene-1,4-sultone, 1,3-propenesultone, 1-fluoro-3-butene-1,4-sultone, 2-fluoro-3-butene-1,4-sultone, 3-fluoro-3-butene-1,4-sultone, 4-fluoro-3-butene-1,4-sultone, 1-methyl-1-butene-1,4-sultone, 2-methyl-1-butene-1,4-sultone, 3-methyl-1-butene-1,4-sultone, 4-methyl-1-butene-1,4-sultone, 1-methyl-2-butene-1,4-sultone, 2-methyl-2-butene-1,4-sultone, 3-methyl-2-butene-1,4-sultone, 4-methyl-2-butene-1,4-sultone, 1-methyl-3-butene-1,4-sultone, 2-methyl-3-butene-1,4-sultone, 3-methyl-3-butene-1,4-sultone, and 4-methyl-3-butene-14-sultone.

In order to enable easy availability and contribute to formation of a stable film-shaped structure, more preferred among these are 1,3-propanesultone, 1-fluoro-1,3-propanesultone, 2-fluoro-1,3-propanesultone, 3-fluoro-1,3-propanesultone, and 1-propene-1,3-sultone. The cyclic sulfonate may be in any amount that does not significantly impair the effects of the invention. The amount is preferably, but not limited to, 0.001% by mass or more and 3.0% by mass or less relative to the electrolyte solution.

The cyclic sulfonate in an amount of not smaller than this lower limit can give a sufficient effect of improving the cycle characteristics to a non-aqueous electrolyte secondary battery. The cyclic sulfonate in an amount of not larger than this upper limit can eliminate an increase in the cost of producing a non-aqueous electrolyte secondary battery. The amount of the cyclic sulfonate is more preferably 0.01% by mass or more, still more preferably 0.1% by mass or more, particularly preferably 0.2% by mass or more, while more preferably 2.5% by mass or less, still more preferably 2.0% by mass or less, particularly preferably 1.8% by mass or less.

The electrolyte solution of the invention may further contain a polyethylene oxide that has a weight average molecular weight of 2000 to 4000 and has —OH, —OCOOH, or —COOH at an end.

The presence of such a compound can improve the stability at the interfaces with the respective electrodes, improving the characteristics of an electrochemical device.

Examples of the polyethylene oxide include polyethylene oxide monool, polyethylene oxide carboxylate, polyethylene oxide diol, polyethylene oxide dicarboxylate, polyethylene oxide triol, and polyethylene oxide tricarboxylate. These may be used alone or in combination of two or more.

In order to give better characteristics of an electrochemical device, preferred are a mixture of polyethylene oxide monool and polyethylene oxide diol and a mixture of polyethylene carboxylate and polyethylene dicarboxylate.

The polyethylene oxide having too small a weight average molecular weight may be easily oxidatively decomposed. The weight average molecular weight is more preferably 3000 to 4000.

The weight average molecular weight can be determined by gel permeation chromatography (GPC) in polystyrene equivalent.

The polyethylene oxide is preferably present in an amount of $1\times10^{-6}$ to $1\times10^{-2}$ mol/kg in the electrolyte solution. Too large an amount of the polyethylene oxide may cause poor characteristics of an electrochemical device.

The amount of the polyethylene oxide is more preferably $5\times10^{-6}$ mol/kg or more.

The electrolyte solution of the invention may further contain any of other components such as an unsaturated cyclic carbonate, an overcharge inhibitor, and a known different aid. This can reduce impairment of the characteristics of an electrochemical device.

Examples of the unsaturated cyclic carbonate include vinylene carbonate compounds, ethylene carbonate compounds substituted with a substituent that contains an aromatic ring, a carbon-carbon double bond, or a carbon-carbon triple bond, phenyl carbonate compounds, vinyl carbonate compounds, allyl carbonate compounds, and catechol carbonate compounds.

Examples of the vinylene carbonate compounds include vinylene carbonate, methylvinylene carbonate, 4,5-dimethylvinylene carbonate, phenylvinylene carbonate, 4,5-diphenylvinylene carbonate, vinylvinylene carbonate, 4,5-divinylvinylene carbonate, allylvinylene carbonate, 4,5-diallylvinylene carbonate, 4-fluorovinylene carbonate, 4-fluoro-5-methylvinylene carbonate, 4-fluoro-5-phenylvinylene carbonate, 4-fluoro-5-vinylvinylene carbonate, 4-allyl-5-fluorovinylene carbonate, ethynylethylene carbonate, propargylethylene carbonate, methylvinylene carbonate, and dimethylvinylene carbonate.

Specific examples of the ethylene carbonate compounds substituted with a substituent that contains an aromatic ring, a carbon-carbon double bond, or a carbon-carbon triple bond include vinylethylene carbonate, 4,5-divinylethylene carbonate, 4-methyl-5-vinylethylene carbonate, 4-allyl-5-vinylethylene carbonate, ethynylethylene carbonate, 4,5-diethynylethylene carbonate, 4-methyl-5-ethynylethylene carbonate, 4-vinyl-5-ethynylethylene carbonate, 4-allyl-5-ethynylethylene carbonate, phenylethylene carbonate, 4,5-diphenylethylene carbonate, 4-phenyl-5-vinylethylene carbonate, 4-allyl-5-phenylethylene carbonate, allylethylene carbonate, 4,5-diallylethylene carbonate, 4-methyl-5-allylethylene carbonate, 4-methylene-1,3-dioxolan-2-one, 4,5-dimethylene-1,3-dioxolan-2-one, and 4-methyl-5-allylethylene carbonate.

The unsaturated cyclic carbonate is preferably vinylene carbonate, methylvinylene carbonate, 4,5-dimethylvinylene carbonate, vinylvinylene carbonate, 4,5-vinylvinylene carbonate, allylvinylene carbonate, 4,5-diallylvinylene carbonate, vinylethylene carbonate, 4,5-divinylethylene carbonate, 4-methyl-5-vinylethylene carbonate, allylethylene carbonate, 4,5-diallylethylene carbonate, 4-methyl-5-allylethylene carbonate, 4-allyl-5-vinylethylene carbonate, ethynylethylene carbonate, 4,5-diethynylethylene carbonate, 4-methyl-5-ethynylethylene carbonate, and 4-vinyl-5-ethynylethylene carbonate. In order to form a more stable interface protecting film, particularly preferred are vinylene carbonate, vinylethylene carbonate, and ethynylethylene carbonate, and most preferred are vinylene carbonate and vinylethylene carbonate.

The unsaturated cyclic carbonate may have any molecular weight that does not significantly impair the effects of the invention. The molecular weight is preferably 50 or higher and 250 or lower. The unsaturated cyclic carbonate having a molecular weight within this range can easily ensure its solubility in the electrolyte solution and can easily lead to sufficient achievement of the effects of the invention. The molecular weight of the unsaturated cyclic carbonate is more preferably 80 or higher and 150 or lower.

The unsaturated cyclic carbonate may be produced by any production method, and may be produced by a known method selected as appropriate.

One unsaturated cyclic carbonate may be used alone or two or more thereof may be used in any combination at any ratio.

The unsaturated cyclic carbonate may be present in any amount that does not significantly impair the effects of the invention. The amount of the unsaturated cyclic carbonate is preferably 0.001% by mass or more, more preferably 0.01% by mass or more, still more preferably 0.1% by mass or more, of 100% by mass of the solvent in the invention. The amount is preferably 5% by mass or less, more preferably 4% by mass or less, still more preferably 3% by mass or less. The unsaturated cyclic carbonate in an amount within the above range allows an electrochemical device containing the electrolyte solution to easily exhibit a sufficient effect of improving the cycle characteristics, and can easily avoid a situation with impaired high-temperature storage characteristics, generation of a large amount of gas, and a reduced discharge capacity retention.

In addition to the aforementioned non-fluorinated unsaturated cyclic carbonates, a fluorinated unsaturated cyclic carbonate may also suitably be used as an unsaturated cyclic carbonate.

The fluorinated unsaturated cyclic carbonate is a cyclic carbonate containing an unsaturated bond and a fluorine atom. The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives and fluorinated ethylene carbonate derivatives substituted with a substituent that contains an aromatic ring or a carbon-carbon double bond.

Examples of the fluorinated vinylene carbonate derivatives include 4-fluorovinylene carbonate, 4-fluoro-5-methylvinylene carbonate, 4-fluoro-5-phenylvinylene carbonate, 4-allyl-5-fluorovinylene carbonate, and 4-fluoro-5-vinylvinylene carbonate.

Examples of the fluorinated ethylene carbonate derivatives substituted with a substituent that contains an aromatic ring or a carbon-carbon double bond include 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, 4,5-difluoro-4,5-diallylethylene carbonate, 4-fluoro-4-phenylethylene carbonate, 4-fluoro-5-phenylethylene carbonate, 4,4-difluoro-5-phenylethylene carbonate, and 4,5-difluoro-4-phenylethylene carbonate.

In order to form a stable interface protecting film, more preferably used as the fluorinated unsaturated cyclic carbonate are 4-fluorovinylene carbonate, 4-fluoro-5-methylvinylene carbonate, 4-fluoro-5-vinylvinylene carbonate, 4-allyl-5-fluorovinylene carbonate, 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, and 4,5-difluoro-4,5-diallylethylene carbonate.

The fluorinated unsaturated cyclic carbonate may have any molecular weight that does not significantly impair the effects of the invention. The molecular weight is preferably 50 or higher and 500 or lower. The fluorinated unsaturated cyclic carbonate having a molecular weight within this range can easily ensure the solubility of the fluorinated unsaturated cyclic carbonate in the electrolyte solution.

The fluorinated unsaturated cyclic carbonate may be produced by any method, and may be produced by any known method selected as appropriate. The molecular weight is more preferably 100 or higher and 200 or lower.

One fluorinated unsaturated cyclic carbonate may be used alone or two or more thereof may be used in any combination at any ratio. The fluorinated unsaturated cyclic carbonate may be contained in any amount that does not significantly impair the effects of the invention. The amount of the fluorinated unsaturated cyclic carbonate is usually preferably 0.01% by mass or more, more preferably 0.1% by mass or more, still more preferably 0.2% by mass or more, while preferably 5% by mass or less, more preferably 4% by mass or less, still more preferably 3% by mass or less, of 100% by mass of the electrolyte solution. The fluorinated unsaturated cyclic carbonate in an amount within this range allows an electrochemical device containing the electrolyte solution to exhibit an effect of sufficiently improving the cycle characteristics and can easily avoid a situation with reduced high-temperature storage characteristics, generation of a large amount of gas, and a reduced discharge capacity retention.

The electrolyte solution of the invention may contain a compound containing a triple bond. This compound may be of any type as long as it contains one or more triple bonds in the molecule.

Specific examples of the compound containing a triple bond include the following compounds:

hydrocarbon compounds such as 1-penthyne, 2-penthyne, 1-hexyne, 2-hexyne, 3-hexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-dodecyne, 2-dodecyne, 3-dodecyne, 4-dodecyne, 5-dodecyne, phenyl acetylene, 1-phenyl-1-propyne, 1-phenyl-2-propyne, l-phenyl-1-butyne, 4-phenyl-1-butyne, 4-phenyl-1-butyne, 1-phenyl-1-penthyne, 5-phenyl-1-penthyne, 1-phenyl-1-hexyne, 6-phenyl-1-hexyne, diphenyl acetylene, 4-ethynyl toluene, and dicyclohexyl acetylene;

monocarbonates such as 2-propynylmethyl carbonate, 2-propynylethyl carbonate, 2-propynylpropyl carbonate, 2-propynylbutyl carbonate, 2-propynylphenyl carbonate, 2-propynylcyclohexyl carbonate, di-2-propynylcarbonate, 1-methyl-2-propynylmethyl carbonate, 1,1-dimethyl-2-propynylmethyl carbonate, 2-butynylmethyl carbonate, 3-butynylmethyl carbonate, 2-pentynylmethyl carbonate, 3-pentynylmethyl carbonate, and 4-pentynylmethyl carbonate;

dicarbonates such as 2-butyne-1,4-diol dimethyl dicarbonate, 2-butyne-1,4-diol diethyl dicarbonate, 2-butyne-1,4-diol dipropyl dicarbonate, 2-butyne-1,4-diol dibutyl dicarbonate, 2-butyne-1,4-diol diphenyl dicarbonate, and 2-butyne-1,4-diol dicyclohexyl dicarbonate;

monocarboxylates such as 2-propynyl acetate, 2-propynyl propionate, 2-propynyl butyrate, 2-propynyl benzoate, 2-propynyl cyclohexylcarboxylate, 1,1-dimethyl-2-propynyl acetate, 1,1-dimethyl-2-propynyl propionate, 1,1-dimethyl-2-propynyl butyrate, 1,1-dimethyl-2-propynyl benzoate, 1,1-dimethyl-2-propynyl cyclohexylcarboxylate, 2-butynyl acetate, 3-butynyl acetate, 2-pentynyl acetate, 3-pentynyl acetate, 4-pentynyl acetate, methyl acrylate, ethyl acrylate, propyl acrylate, vinyl acrylate, 2-propenyl acrylate, 2-butenyl acrylate, 3-butenyl acrylate, methyl methacrylate, ethyl methacrylate, propyl methacrylate, vinyl methacrylate, 2-propenyl methacrylate, 2-butenyl methacrylate, 3-butenyl methacrylate, methyl 2-propynoate, ethyl 2-propynoate, propyl 2-propynoate, vinyl 2-propynoate, 2-propenyl 2-propynoate, 2-butenyl 2-propynoate, 3-butenyl 2-propynoate, methyl 2-butynoate, ethyl 2-butynoate, propyl 2-butynoate, vinyl 2-butynoate, 2-propenyl 2-butynoate, 2-butenyl 2-butynoate, 3-butenyl 2-butynoate, methyl 3-butynoate, ethyl 3-butynoate, propyl 3-butynoate, vinyl 3-butynoate, 2-propenyl 3-butynoate, 2-butenyl 3-butynoate, 3-butenyl 3-butynoate, methyl 2-penthynoate, ethyl 2-penthynoate, propyl 2-penthynoate, vinyl 2-penthynoate, 2-propenyl 2-penthynoate, 2-butenyl 2-penthynoate, 3-butenyl 2-penthynoate, methyl 3-penthynoate, ethyl 3-penthynoate, propyl 3-penthynoate, vinyl 3-penthynoate, 2-propenyl 3-penthynoate, 2-butenyl 3-penthynoate, 3-butenyl 3-penthynoate, methyl 4-penthynoate, ethyl 4-penthynoate, propyl 4-penthynoate, vinyl 4-penthynoate, 2-propenyl 4-penthynoate, 2-butenyl 4-penthynoate, and 3-butenyl 4-penthynoate, fumarates, methyl trimethylacetate, and ethyl trimethylacetate;

dicarboxylates such as 2-butyne-1,4-diol diacetate, 2-butyne-1,4-diol dipropionate, 2-butyne-1,4-diol dibutyrate, 2-butyne-1,4-diol dibenzoate, 2-butyne-1,4-diol dicyclohexanecarboxylate, hexahydrobenzo[1,3,2]dioxathiolane-2-oxide (1,2-cyclohexane diol, 2,2-dioxide-1,2-oxathiolan-4-yl acetate, and 2,2-dioxide-1,2-oxathiolan-4-yl acetate;

oxalic acid diesters such as methyl 2-propynyl oxalate, ethyl 2-propynyl oxalate, propyl 2-propynyl oxalate, 2-propynyl vinyl oxalate, allyl 2-propynyl oxalate, di-2-propynyl oxalate, 2-butynyl methyl oxalate, 2-butynyl ethyl oxalate, 2-butynyl propyl oxalate, 2-butynyl vinyl oxalate, allyl 2-butynyl oxalate, di-2-butynyl oxalate, 3-butynyl methyl oxalate, 3-butynyl ethyl oxalate, 3-butynyl propyl oxalate, 3-butynyl vinyl oxalate, allyl 3-butynyl oxalate, and di-3-butynyl oxalate;

phosphine oxides such as methyl(2-propynyl) (vinyl) phosphine oxide, divinyl(2-propynyl)phosphine oxide, di(2-propynyl) (vinyl)phosphine oxide, di(2-propenyl)2(-propynyl)phosphine oxide, di(2-propynyl) (2-propenyl)phosphine oxide, di(3-butenyl)(2-propynyl)phosphine oxide, and di(2-propynyl) (3-butenyl)phosphine oxide;

phosphinates such as 2-propynyl methyl(2-propenyl) phosphinate, 2-propynyl 2-butenyl(methyl)phosphinate, 2-propynyl di(2-propenyl)phosphinate, 2-propynyl di(3-butenyl)phosphinate, 1,1-dimethyl-2-propynyl methyl(2-propenyl)phosphinate, 1,1-dimethyl-2-propynyl 2-butenyl (methyl)phosphinate, 1,1-dimethyl-2-propynyl di(2-propenyl)phosphinate, 1,1-dimethyl-2-propynyl di(3-butenyl)phosphinate, 2-propenyl methyl(2-propynyl) phosphinate, 3-butenyl methyl(2-propynyl)phosphinate, 2-propenyl di(2-propynyl)phosphinate, 3-butenyl di(2-propynyl)phosphinate, 2-propenyl 2-propynyl(2-propenyl) phosphinate, and 3-butenyl 2-propynyl(2-propenyl)phosphinate;

phosphonates such as methyl 2-propynyl 2-propenylphosphonate, methyl(2-propynyl) 2-butenylphosphonate, (2-propynyl)(2-propenyl) 2-propenylphosphonate, (3-butenyl) (2-propynyl) 3-butenylphosphonate, (1,1-dimethyl-2-propynyl) (methyl) 2-propenylphosphonate, (1,1-dimethyl-2-propynyl) (methyl) 2-butenylphosphonate, (1,1-dimethyl-2-propynyl)(2-propenyl) 2-propenylphosphonate, (3-butenyl) (1,1-dimethyl-2-propynyl) 3-butenylphosphonate, (2-propynyl)(2-propenyl) methylphosphonate, (3-butenyl) (2-propynyl) methylphosphonate, (1,1-dimethyl-2-propynyl)(2-propenyl) methylphosphonate, (3-butenyl) (1,1-dimethyl-2-propynyl) methylphosphonate, (2-propynyl)(2-propenyl) ethylphosphonate, (3-butenyl) (2-propynyl) ethylphosphonate, (1,1-dimethyl-2-propynyl) (2-propenyl) ethylphosphonate, and (3-butenyl) (1,1-dimethyl-2-propynyl) ethylphosphonate; and phosphates such as (methyl) (2-propenyl)(2-propynyl) phosphate, (ethyl) (2-propenyl) (2-propynyl) phosphate, (2-butenyl) (methyl) (2-propynyl) phosphate, (2-butenyl) (ethyl) (2-propynyl) phosphate, (1,1-dimethyl-2-propynyl) (methyl) (2-propynyl) phosphate, (1,1-dimethyl-2-propynyl) (ethyl) (2-propenyl) phosphate, (2-butenyl) (1,1-dimethyl-2-propynyl) (methyl) phosphate, and (2-butenyl) (ethyl) (1,1-dimethyl-2-propynyl) phosphate.

In order to more stably form a negative electrode film in the electrolyte solution, preferred among these are compounds containing an alkynyloxy group.

In order to improve the storage characteristics, particularly preferred are compounds such as 2-propynylmethyl carbonate, di-2-propynyl carbonate, 2-butyne-1,4-diol dimethyl dicarbonate, 2-propynyl acetate, 2-butyne-1,4-diol diacetate, methyl 2-propynyl oxalate, and di-2-propynyl oxalate.

One compound containing a triple bond may be used alone or two or more thereof may be used in any combination at any ratio. The compound containing a triple bond may be present in any amount that does not significantly impair the effects of the invention relative to the whole electrolyte solution of the invention. The compound is usually contained at a concentration of 0.01% by mass or more, preferably 0.05% by mass or more, more preferably 0.1% by mass or more, while usually 5% by mass or less, preferably 3% by mass or less, more preferably 1% by mass or less, relative to the electrolyte solution of the invention. The compound satisfying the above range can further improve the effects such as output characteristics, load characteristics, cycle characteristics, and high-temperature storage characteristics.

In order to effectively reduce burst or combustion of a battery in case of overcharge, for example, of an electrochemical device containing the electrolyte solution, the electrolyte solution of the invention may contain an overcharge inhibitor.

Examples of the overcharge inhibitor include aromatic compounds, including unsubstituted or alkyl-substituted terphenyl derivatives such as biphenyl, o-terphenyl, m-terphenyl, and p-terphenyl, partially hydrogenated products of unsubstituted or alkyl-substituted terphenyl derivatives, cyclohexylbenzene, t-butylbenzene, t-amylbenzene, diphenyl ether, dibenzofuran, diphenyl cyclohexane, 1,1,3-trimethyl-3-phenylindan, cyclopentylbenzene, cyclohexylbenzene, cumene, 1,3-diisopropylbenzene, 1,4-diisopropylbenzene, t-butylbenzene, t-amylbenzene, t-hexylbenzene, and anisole; partially fluorinated products of the aromatic compounds such as 2-fluorobiphenyl, 4-fluorobiphenyl, o-cyclohexylfluorobenzene, p-cyclohexylfluorobenzene, o-cyclohexylfluorobenzene, p-cyclohexylfluorobenzene, fluorobenzene, fluorotoluene, and benzotrifluoride; fluorine-containing anisole compounds such as 2,4-difluoroanisole, 2,5-difluoroanisole, 1,6-difluoroanisole, 2,6-difluoroanisole, and 3,5-difluoroanisole; aromatic acetates such as 3-propylphenyl acetate, 2-ethylphenyl acetate, benzylphenyl acetate, methylphenyl acetate, benzyl acetate, and phenethylphenyl acetate; aromatic carbonates such as diphenyl carbonate and methylphenyl carbonate; toluene derivatives such as toluene and xylene, and unsubstituted or alkyl-substituted biphenyl derivatives such as 2-methylbiphenyl, 3-methylbiphenyl, 4-methylbiphenyl, and o-cyclohexylbiphenyl. Preferred among these are aromatic compounds such as biphenyl, alkylbiphenyl, terphenyl, partially hydrogenated terphenyl, cyclohexylbenzene, t-butylbenzene, t-amylbenzene, diphenyl ether, and dibenzofuran, diphenyl cyclohexane, 1,1,3-trimethyl-3-phenylindan, 3-propylphenyl acetate, 2-ethylphenyl acetate, benzylphenyl acetate, methylphenyl acetate, benzyl acetate, diphenyl carbonate, and methylphenyl carbonate. These compounds may be used alone or in combination of two or more. In order to achieve good balance between the overcharge inhibiting characteristics and the high-temperature storage characteristics with a combination use of two or more thereof, preferred is a combination of cyclohexylbenzene and t-butylbenzene or t-amylbenzene, or a combination of at least one oxygen-free aromatic compound selected from biphenyl, alkylbiphenyl, terphenyl, partially hydrogenated terphenyl, cyclohexylbenzene, t-butylbenzene, t-amylbenzene, and the like and at least one oxygen-containing aromatic compound selected from diphenyl ether, dibenzofuran, and the like.

The electrolyte solution used in the invention may contain a carboxylic anhydride other than the compound (2). Preferred is a compound represented by the following formula (6). The carboxylic anhydride may be produced by any method which may be selected from known methods as appropriate.

[Chem. 67]

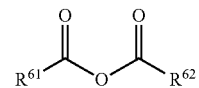

In the formula (6), $R^{61}$ and $R^{62}$ are each individually a hydrocarbon group having a carbon number of 1 or greater and 15 or smaller and optionally containing a substituent.

$R^{61}$ and $R^{62}$ each may be any monovalent hydrocarbon group. For example, each of them may be either an aliphatic hydrocarbon group or an aromatic hydrocarbon group, or may be a bond of an aliphatic hydrocarbon group and an aromatic hydrocarbon group. The aliphatic hydrocarbon group may be a saturated hydrocarbon group and may contain an unsaturated bond (carbon-carbon double bond or carbon-carbon triple bond). The aliphatic hydrocarbon group may be either acyclic or cyclic. In the case of an acyclic group, it may be either linear or branched. The group may be a bond of an acyclic group and a cyclic group. $R^{61}$ and $R^{62}$ may be the same as or different from each other.

When the hydrocarbon group for $R^{61}$ and $R^{62}$ contains a substituent, the substituent may be of any type as long as it is not beyond the scope of the invention. Examples thereof include halogen atoms such as a fluorine atom, a chlorine atom, a bromine atom, and an iodine atom. Preferred is a fluorine atom. Examples of the substituent other than the halogen atoms include substituents containing a functional group such as an ester group, a cyano group, a carbonyl group, or an ether group. Preferred are a cyano group and a carbonyl group. The hydrocarbon group for $R^{61}$ and $R^{62}$ may contain only one of these substituents or may contain two or more thereof. When two or more substituents are contained, these substituents may be the same as or different from each other.

The hydrocarbon group for $R^{61}$ and $R^{62}$ has a carbon number of usually 1 or greater, while usually 15 or smaller, preferably 12 or smaller, more preferably 10 or smaller, still more preferably 9 or smaller. When $R^1$ and $R^2$ bind to each other to form a divalent hydrocarbon group, the divalent hydrocarbon group has a carbon number of usually 1 or greater, while usually 15 or smaller, preferably 13 or smaller, more preferably 10 or smaller, still more preferably 8 or smaller. When the hydrocarbon group for $R^{61}$ and $R^{62}$ contains a substituent that contains a carbon atom, the carbon number of the whole $R^{61}$ or $R^{62}$ including the substituent preferably satisfies the above range.

Next, specific examples of the acid anhydride represented by the formula (6) are described. In the following examples, the term "analog" means an acid anhydride obtainable by replacing part of the structure of an acid anhydride mentioned as an example by another structure within the scope of the invention. Examples thereof include dimers, trimers, and tetramers each composed of a plurality of acid anhydrides, structural isomers such as those having a substituent that has the same carbon number but also has a branch, and those having a different site at which a substituent binds to the acid anhydride.

First, specific examples of an acid anhydride in which $R^{61}$ and $R^{62}$ are the same as each other are described.

Specific examples of an acid anhydride in which $R^{61}$ and $R^{62}$ are linear alkyl groups include acetic anhydride, propionic anhydride, butanoic anhydride, 2-methylpropionic anhydride, 2,2-dimethylpropionic anhydride, 2-methylbutanoic anhydride, 3-methylbutanoic anhydride, 2,2-dimethylbutanoic anhydride, 2,3-dimethylbutanoic anhydride, 3,3-dimethylbutanoic anhydride, 2,2,3-trimethylbutanoic anhydride, 2,3,3-trimethylbutanoic anhydride, 2,2,3,3-tetramethylbutanoic anhydride, and 2-ethylbutanoic anhydride, and analogs thereof.

Specific examples of an acid anhydride in which $R^{61}$ and $R^{62}$ are cyclic alkyl groups include cyclopropanecarboxylic anhydride, cyclopentanecarboxylic anhydride, and cyclohexanecarboxylic anhydride, and analogs thereof.

Specific examples of an acid anhydride in which $R^{61}$ and $R^{62}$ are alkenyl groups include acrylic anhydride, 2-methylacrylic anhydride, 3-methylacrylic anhydride, 2,3-dimethylacrylic anhydride, 3,3-dimethylacrylic anhydride, 2,3,3-trimethylacrylic anhydride, 2-phenylacrylic anhydride, 3-phenylacrylic anhydride, 2,3-diphenylacrylic anhydride, 3,3-diphenylacrylic anhydride, 3-butenoic anhydride, 2-methyl-3-butenoic anhydride, 2,2-dimethyl-3-butenoic anhydride, 3-methyl-3-butenoic anhydride, 2-methyl-3-methyl-3-butenoic anhydride, 2,2-dimethyl-3-methyl-3-butenoic anhydride, 3-pentenoic anhydride, 4-pentenoic anhydride, 2-cyclopentenecarboxylic anhydride, 3-cyclopentenecarboxylic anhydride, and 4-cyclopentenecarboxylic anhydride, and analogs thereof.

Specific examples of an acid anhydride in which $R^{61}$ and $R^{62}$ are alkynyl groups include propynoic anhydride, 3-phenylpropynoic anhydride, 2-butynoic anhydride, 2-penthynoic anhydride, 3-butynoic anhydride, 3-penthynoic anhydride, and 4-penthynoic anhydride, and analogs thereof.

Specific examples of an acid anhydride in which $R^{61}$ and $R^{62}$ are aryl groups include benzoic anhydride, 4-methylbenzoic anhydride, 4-ethylbenzoic anhydride, 4-tert-butylbenzoic anhydride, 2-methylbenzoic anhydride, 2,4,6-trimethylbenzoic anhydride, 1-naphthalenecarboxylic anhydride, and 2-naphthalenecarboxylic anhydride, and analogs thereof.

Examples of an acid anhydride substituted with a fluorine atom are mainly listed below as examples of the acid anhydride in which $R^{61}$ and $R^{62}$ are substituted with a halogen atom. Acid anhydrides obtainable by replacing any or all of the fluorine atoms thereof with a chlorine atom, a bromine atom, or an iodine atom are also included in the exemplary compounds.

Examples of an acid anhydride in which $R^{61}$ and $R^{62}$ are halogen-substituted linear alkyl groups include fluoroacetic anhydride, difluoroacetic anhydride, trifluoroacetic anhydride, 2-fluoropropionic anhydride, 2,2-difluoropropionic anhydride, 2,3-difluoropropionic anhydride, 2,2,3-trifluoropropionic anhydride, 2,3,3-trifluoropropionic anhydride, 2,2,3,3-tetrapropionic anhydride, 2,3,3,3-tetrapropionic anhydride, 3-fluoropropionic anhydride, 3,3-difluoropropionic anhydride, 3,3,3-trifluoropropionic anhydride, and perfluoropropionic anhydride, and analogs thereof.

Examples of an acid anhydride in which $R^{61}$ and $R^{62}$ are halogen-substituted cyclic alkyl groups include 2-fluorocyclopentanecarboxylic anhydride, 3-fluorocyclopentanecarboxylic anhydride, and 4-fluorocyclopentanecarboxylic anhydride, and analogs thereof.

Examples of an acid anhydride in which $R^{61}$ and $R^{62}$ are halogen-substituted alkenyl groups include 2-fluoroacrylic anhydride, 3-fluoroacrylic anhydride, 2,3-difluoroacrylic anhydride, 3,3-difluoroacrylic anhydride, 2,3,3-trifluoroacrylic anhydride, 2-(trifluoromethyl)acrylic anhydride, 3-(trifluoromethyl)acrylic anhydride, 2,3-bis(trifluoromethyl)acrylic anhydride, 2,3,3-tris(trifluoromethyl)acrylic anhydride, 2-(4-fluorophenyl)acrylic anhydride, 3-(4-fluorophenyl)acrylic anhydride, 2,3-bis(4-fluorophenyl)acrylic anhydride, 3,3-bis(4-fluorophenyl)acrylic anhydride, 2-fluoro-3-butenoic anhydride, 2,2-difluoro-3-butenoic anhydride, 3-fluoro-2-butenoic anhydride, 4-fluoro-3-butenoic anhydride, 3,4-difluoro-3-butenoic anhydride, and 3,3,4-trifluoro-3-butenoic anhydride, and analogs thereof.

Examples of an acid anhydride in which $R^{61}$ and $R^{62}$ are halogen-substituted alkynyl groups include 3-fluoro-2-propynoic anhydride, 3-(4-fluorophenyl)-2-propynoic anhydride, 3-(2,3,4,5,6-pentafluorophenyl)-2-propynoic anhydride, 4-fluoro-2-butynoic anhydride, 4,4-difluoro-2-butynoic anhydride, and 4,4,4-trifluoro-2-butynoic anhydride, and analogs thereof.

Examples of an acid anhydride in which $R^{61}$ and $R^{62}$ are halogen-substituted aryl groups include 4-fluorobenzoic anhydride, 2,3,4,5,6-pentafluorobenzoic anhydride, and 4-trifluoromethylbenzoic anhydride, and analogs thereof.

Examples of an acid anhydride in which $R^{61}$ and $R^{62}$ each contains a substituent containing a functional group such as an ester, a nitrile, a ketone, an ether, or the like include methoxyformic anhydride, ethoxyformic anhydride, methyloxalic anhydride, ethyloxalic anhydride, 2-cyanoacetic anhydride, 2-oxopropionic anhydride, 3-oxobutanoic anhydride, 4-acetylbenzoic anhydride, methoxyacetic anhydride, and 4-methoxybenzoic anhydride, and analogs thereof.

Then, specific examples of an acid anhydride in which $R^{61}$ and $R^{62}$ are different from each other are described below.

$R^{61}$ and $R^{62}$ may be in any combination of those mentioned as examples above and analogs thereof. The following gives representative examples.

Examples of a combination of linear alkyl groups include acetic propionic anhydride, acetic butanoic anhydride, butanoic propionic anhydride, and acetic 2-methylpropionic anhydride.

Examples of a combination of a linear alkyl group and a cyclic alkyl group include acetic cyclopentanoic anhydride, acetic cyclohexanoic anhydride, and cyclopentanoic propionic anhydride.

Examples of a combination of a linear alkyl group and an alkenyl group include acetic acrylic anhydride, acetic 3-methylacrylic anhydride, acetic 3-butenoic anhydride, and acrylic propionic anhydride.

Examples of a combination of a linear alkyl group and an alkynyl group include acetic propynoic anhydride, acetic 2-butynoic anhydride, acetic 3-butynoic anhydride, acetic 3-phenyl propynoic anhydride, and propionic propynoic anhydride.

Examples of a combination of a linear alkyl group and an aryl group include acetic benzoic anhydride, acetic 4-methylbenzoic anhydride, acetic 1-naphthalenecarboxylic anhydride, and benzoic propionic anhydride.

Examples of a combination of a linear alkyl group and a hydrocarbon group containing a functional group include acetic fluoroacetic anhydride, acetic trifluoroacetic anhydride, acetic 4-fluorobenzoic anhydride, fluoroacetic propionic anhydride, acetic alkyloxalic anhydride, acetic 2-cyanoacetic anhydride, acetic 2-oxopropionic anhydride, acetic methoxyacetic anhydride, and methoxyacetic propionic anhydride.

Examples of a combination of cyclic alkyl groups include cyclopentanoic cyclohexanoic anhydride.

Examples of a combination of a cyclic alkyl group and an alkenyl group include acrylic cyclopentanoic anhydride, 3-methylacrylic cyclopentanoic anhydride, 3-butenoic cyclopentanoic anhydride, and acrylic cyclohexanoic anhydride.

Examples of a combination of a cyclic alkyl group and an alkynyl group include propynoic cyclopentanoic anhydride, 2-butynoic cyclopentanoic anhydride, and propynoic cyclohexanoic anhydride.

Examples of a combination of a cyclic alkyl group and an aryl group include benzoic cyclopentanoic anhydride, 4-methylbenzoic cyclopentanoic anhydride, and benzoic cyclohexanoic anhydride.

Examples of a combination of a cyclic alkyl group and a hydrocarbon group containing a functional group include fluoroacetic cyclopentanoic anhydride, cyclopentanoic trifluoroacetic anhydride, cyclopentanoic 2-cyanoacetic anhydride, cyclopentanoic methoxyacetic anhydride, and cyclohexanoic fluoroacetic anhydride.

Examples of a combination of alkenyl groups include acrylic 2-methylacrylic anhydride, acrylic 3-methylacrylic anhydride, acrylic 3-butenoic anhydride, and 2-methylacrylic 3-methylacrylic anhydride.

Examples of a combination of an alkenyl group and an alkynyl group include acrylic propynoic anhydride, acrylic 2-butynoic anhydride, and 2-methylacrylic propynoic anhydride.

Examples of a combination of an alkenyl group and an aryl group include acrylic benzoic anhydride, acrylic 4-methylbenzoic anhydride, and 2-methylacrylic benzoic anhydride.

Examples of a combination of an alkenyl group and a hydrocarbon group containing a functional group include acrylic fluoroacetic anhydride, acrylic trifluoroacetic anhydride, acrylic 2-cyanoacetic anhydride, acrylic methoxyacetic anhydride, and 2-methylacrylic fluoroacetic anhydride.

Examples of a combination of alkynyl groups include propynoic 2-butynoic anhydride, propynoic 3-butynoic anhydride, and 2-butynoic 3-butynoic anhydride.

Examples of a combination of an alkynyl group and an aryl group include benzoic propynoic anhydride, 4-methylbenzoic propynoic anhydride, and benzoic 2-butynoic anhydride.

Examples of a combination of an alkynyl group and a hydrocarbon group containing a functional group include propynoic fluoroacetic anhydride, propynoic trifluoroacetic anhydride, propynoic 2-cyanoacetic anhydride, propynoic methoxyacetic anhydride, and 2-butynoic fluoroacetic anhydride.

Examples of a combination of aryl groups include benzoic 4-methylbenzoic anhydride, benzoic 1-naphthalenecarboxylic anhydride, and 4-methylbenzoic 1-naphthalenecarboxylic anhydride.

Examples of a combination of an aryl group and a hydrocarbon group containing a functional group include benzoic fluoroacetic anhydride, benzoic trifluoroacetic anhydride, benzoic 2-cyanoacetic anhydride, benzoic methoxyacetic anhydride, and 4-methylbenzoic fluoroacetic anhydride.

Examples of a combination of hydrocarbon groups each containing a functional group include fluoroacetic trifluoroacetic anhydride, fluoroacetic 2-cyanoacetic anhydride, fluoroacetic methoxyacetic anhydride, and trifluoroacetic 2-cyanoacetic anhydride.

Preferred among the acid anhydrides having an acyclic structure are acetic anhydride, propionic anhydride, 2-methylpropionic anhydride, cyclopentanecarboxylic anhydride, cyclohexanecarboxylic anhydride, acrylic anhydride, 2-methylacrylic anhydride, 3-methylacrylic anhydride, 2,3-dimethylacrylic anhydride, 3,3-dimethylacrylic anhydride, 3-butenoic anhydride, 2-methyl-3-butenoic anhydride, propynoic anhydride, 2-butynoic anhydride, benzoic anhydride, 2-methylbenzoic anhydride, 4-methylbenzoic anhydride, 4-tert-butylbenzoic anhydride, trifluoroacetic anhydride, 3,3,3-trifluoropropionic anhydride, 2-(trifluoromethyl)acrylic anhydride, 2-(4-fluorophenyl)acrylic anhydride, 4-fluorobenzoic anhydride, 2,3,4,5,6-pentafluorobenzoic anhydride, methoxyformic anhydride, and ethoxyformic anhydride. More preferred are acrylic anhydride, 2-methylacrylic anhydride, 3-methylacrylic anhydride, benzoic anhydride, 2-methylbenzoic anhydride, 4-methylbenzoic anhydride, 4-tert-butylbenzoic anhydride, 4-fluorobenzoic anhydride, 2,3,4,5,6-pentafluorobenzoic anhydride, methoxyformic anhydride, and ethoxyformic anhydride.

These compounds are preferred because they can appropriately form a bond with lithium oxalate to provide a film having excellent durability, thereby improving especially the charge and discharge rate characteristics after a durability test, input and output characteristics, and impedance characteristics.

The carboxylic anhydride may have any molecular weight that does not significantly impair the effects of the invention. The molecular weight is usually 90 or higher, preferably 95 or higher, while usually 300 or lower, preferably 200 or lower. The carboxylic anhydride having a molecular weight within the above range can reduce an increase in viscosity of an electrolyte solution and can give a reasonable film density, appropriately improving the durability.

The carboxylic anhydride may be formed by any production method which may be selected from known methods. One of the carboxylic anhydrides described above alone may be contained in the non-aqueous electrolyte solution of the invention, or two or more thereof may be contained in any combination at any ratio.

The carboxylic anhydride may be contained in any amount that does not significantly impair the effects of the invention relative to the electrolyte solution of the invention. The carboxylic anhydride is usually contained at a concentration of 0.01% by mass or more, preferably 0.1% by mass or more, while usually 5% by mass or less, preferably 3% by mass or less, relative to the electrolyte solution of the invention. The carboxylic anhydride in an amount within the above range can easily achieve an effect of improving the cycle characteristics and have good reactivity, easily improving the battery characteristics.

The electrolyte solution of the invention may further contain a known different aid. Examples of the different aid include carbonate compounds such as erythritan carbonate, spiro-bis-dimethylene carbonate, and methoxyethyl-methyl carbonate; spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, methyl fluorosulfonate, ethyl fluorosulfonate, methyl methanesulfonate, ethyl methanesulfonate, busulfan, sulfolene, ethylene sulfate, vinylene sulfate, diphenyl sulfone, N,N-dimethylmethanesulfonamide, N,N-diethylmethanesulfonamide, acetamide, N-methyl formamide, N,N-dimethyl formamide, N,N-dimethyl acetamide, methyl vinyl sulfonate, ethyl vinyl sulfonate, allyl vinyl sulfonate, propargyl vinyl sulfonate, methyl allyl sulfonate, ethyl allyl sulfonate, allyl allyl sulfonate, propargyl allyl sulfonate, 1,2-bis(vinylsulfonyloxy) ethane, propanedisulfonic anhydride, sulfobutyric anhydride, sulfobenzoic anhydride, sulfopropionic anhydride, ethanedisulfonic anhydride, methylene methanedisulfonate, 2-propynyl methanesulfonate, pentene sulfite, pentafluorophenyl methanesulfonate, propylene sulfate, propylene sulfite, propane sultone, butylene sulfite, butane-2,3-diyl dimethanesulfonate, 2-butyne-1,4-diyl dimethanesulfonate, 2-phenyl bicyclohexyl, 2-butyne-1,4-diyl diformate, 2-propynyl vinyl sulfonate, bis(2-vinylsulfonylethyl)ether, 5-vinyl-hexahydro-1,3,2-benzodioxathiol-2-oxide, 2-propynyl 2-(methanesulfonyloxy)propionate, 5,5-dimethyl-1,2-oxathiolan-4-one 2,2-dioxide, 3-sulfo-propionic anhydride, trimethylene methanedisulfonate, 2-methyl tetrahydrofuran, trimethylene methanedisulfonate, tetramethylene sulfoxide, dimethylene methanedisulfonate, difluoroethyl methyl sulfone, divinyl sulfone, 1,2-bis(vinylsulfonyl)ethane, methyl ethylenebisphosphonate, ethyl ethylenebisphosphonate, and ethylene sulfate; nitrogen-containing compounds such as 1-methyl-2-pyrrolidinone, 1-methyl-2-piperidone, 3-methyl-2-oxazolidinone, 1,3-dimethyl-2-imidazolidinone, N-methylsuccinimide, nitromethane, nitroethane, thiophene 1-oxide, and ethylene diamine; phosphorus-containing compounds such as trimethyl phosphite, triethyl phosphite, triphenyl phosphite, trimethyl phosphate, triethyl phosphate, triphenyl phosphate, dimethyl methyl phosphonate, diethyl ethyl phosphonate, dimethyl vinyl phosphonate, diethyl vinyl phosphonate, ethyl diethyl phosphonoacetate, methyl dimethyl phosphinate, ethyl diethyl phosphinate, trimethylphosphine oxide, triethylphosphine oxide, bis(2,2-difluoroethyl) 2,2,2-trifluoroethyl phosphate, bis(2,2,3,3-tetrafluoropropyl)2,2,2-trifluoroethyl phosphate, bis(2,2,2-trifluoroethyl)methyl phosphate, bis(2,2,2-trifluoroethyl) ethyl phosphate, bis(2,2,2-trifluoroethyl)2,2-difluoroethyl phosphate, bis(2,2,2-trifluoroethyl)2,2,3,3-tetrafluoropropyl phosphate, tributyl phosphate, tris(2,2,2-trifluoroethyl) phosphate, tris(1,1,1,3,3,3-hexafluoropropan-2-yl) phosphate, trioctyl phosphate, 2-phenylphenyldimethyl phosphate, 2-phenylphenyldiethyl phosphate, (2,2,2-trifluoroethyl) (2,2,3,3-tetrafluoropropyl)methyl phosphate, phosphoric acid triester, methyl methylenebisphosphonate, ethyl methylenebisphosphonte, methyl 2-(dimethoxyphosphoryl)acetate, methyl 2-(dimethylphosphoryl)acetate, methyl 2-(diethoxyphosphoryl)acetate, methyl 2-(diethylphosphoryl)acetate, methyl butylenebisphosphonate, ethyl butylenebisphosphonate, 2-propynyl 2-(dimethoxyphosphoryl)acetate, 2-propynyl 2-(dimethylphosphoryl)acetate, 2-propynyl 2-(diethoxyphosphoryl)acetate, 2-propynyl 2-(diethylphosphoryl)acetate, tris(trimethylsilyl)phosphate, tris(trimethylsilyl)phosphite, tris(triethylsilyl)phosphate, and tris(triethylsilyl)phosphite; hydrocarbon compounds such as heptane, octane, nonane, decane, cycloheptane, methyl formate, methyl 2-propynyloxalate, 2-propynyl methacrylate, dimethyl malonate, malonic acid ester, pentane, benzene, furan, naphthalene, 2,5,8,11-tetraoxadodecane, 2,5,8,11,14-pentaoxapentadecane, 3-pentanone, 2-phenyl bicyclohexyl, 3-allyl succinic anhydride, ethoxymethoxyethane, trimethoxymethane, and cyclohexane; fluorine-containing aromatic compounds such as fluorobenzene, difluorobenzene, hexafluorobenzene, benzotrifluoride, monofluorobenzene, 1-fluoro-2-cyclohexylbenzene, 1-fluoro-4-tert-butylbenzene, 1-fluoro-3-cyclohexylbenzene, 1-fluoro-2-cyclohexylbenzene, and fluorinated biphenyl; silane compounds such as tris(trimethylsilyl) borate, tris(trimethoxysilyl) borate, tris(trimethylsilyl) phosphate, tris(trimethoxysilyl) phosphate, dimethoxyaluminoxytrimethoxysilane, diethoxyaluminoxytriethoxysilane, dipropoxyaluminoxytriethoxysilane, dibutoxyaluminoxytrimethoxysilane, dibutoxyaluminoxytriethoxysilane, titanium tetrakis(trimethylsiloxide), titanium tetrakis(triethylsiloxide), tris(trimethylsilyl) phosphite, trimethylsilyl polyphosphate, and tetramethylsilane; and oxygen-containing compounds such as dimethyl oxalate, dioxolane, dioxane, dimethyl ketone, diethyl ketone, diethyl oxalate, di(2-propynyl)oxalate, dimethyl succinate, di(2-propynyl) glutarate, 2-propynyl formate, ethyl formate, glyme, ethyl monoglyme, ethylmethyl oxalate, and ethyl formate. One of these compounds may be used alone or two or more thereof may be used in combination. These aids can improve the capacity retention characteristics and the cycle characteristics after high-temperature storage.

Preferred among these as the different aid are phosphorus-containing compounds, especially preferred is tris(trimethylsilyl)phosphate.

The different aid may be present in any amount that does not significantly impair the effects of the invention. The amount of the different aid is preferably 0.01% by mass or more and 5% by mass or less of 100% by mass of the electrolyte solution. The different aid in an amount within this range can easily sufficiently exhibit the effects thereof and can easily avoid a situation with impairment of battery characteristics such as high-load discharge characteristics. The amount of the different aid is more preferably 0.1% by mass or more, still more preferably 0.2% by mass or more, while more preferably 3% by mass or less, still more preferably 1% by mass or less.

The electrolyte solution of the invention may further contain as an additive any of a cyclic carboxylate, an acyclic carboxylate, an ether compound, a nitrogen-containing compound, a boron-containing compound, an organosilicon-containing compound, a fireproof agent (flame retardant), a surfactant, an additive for increasing the permittivity, an improver for cycle characteristics and rate characteristics, and a sulfone-based compound to the extent that the effects of the invention are not impaired.

Examples of the cyclic carboxylate include those having a carbon number of 3 to 12 in total in the structural formula. Specific examples thereof include gamma-butyrolactone, gamma-valerolactone, gamma-caprolactone, epsilon-caprolactone, and 3-methyl-γ-butyrolactone. In order to improve the characteristics of an electrochemical device owing to improvement in the degree of dissociation of lithium ions, particularly preferred is gamma-butyrolactone.

In general, the cyclic carboxylate as an additive is preferably present in an amount of 0.1% by mass or more, more preferably 1% by mass or more, of 100% by mass of the solvent. The cyclic carboxylate in an amount within this range can easily improve the electric conductivity of the electrolyte solution, improving the large-current discharge characteristics of an electrochemical device. The amount of the cyclic carboxylate is also preferably 10% by mass or less, more preferably 5% by mass or less. Such an upper limit may allow the electrolyte solution to have a viscosity within an appropriate range, may make it possible to avoid a reduction in the electric conductivity, may reduce an increase in the resistance of the negative electrode, and may allow an electrochemical device to have large-current discharge characteristics within a favorable range.

The cyclic carboxylate to be suitably used may also be a fluorinated cyclic carboxylate (fluorine-containing lactone).

Examples of the fluorine-containing lactone include fluorine-containing lactones represented by the following formula (C):

[Chem. 68]

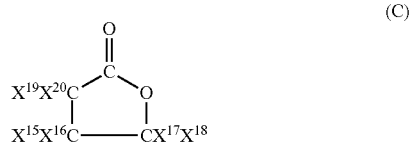

wherein $X^{15}$ to $X^{20}$ are the same as or different from each other, and are each —H, —F, —Cl, —CH$_3$, or a fluorinated alkyl group; and at least one selected from $X^{15}$ to $X^{20}$ is a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. In order to achieve high oxidation resistance and an effect of improving the safety, —CH$_2$CF$_3$ and —CH$_2$CF$_2$CF$_3$ are preferred.

One of $X^{15}$ to $X^{20}$ or a plurality thereof may be replaced by —H, —F, —Cl, —CH$_3$, or a fluorinated alkyl group only when at least one selected from $X^{15}$ to $X^{20}$ is a fluorinated alkyl group. In order to give good solubility of an electrolyte salt, the number of substituents is preferably 1 to 3, more preferably 1 or 2.

The substitution of the fluorinated alkyl group may be at any of the above sites. In order to give a good synthesizing yield, the substitution site is preferably $X^{17}$ and/or $X^{18}$. In particular, $X^{17}$ or $X^{18}$ is preferably a fluorinated alkyl group, especially —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In order to give good solubility of an electrolyte salt, —H is preferred.

In addition to those represented by the above formula, the fluorine-containing lactone may also be a fluorine-containing lactone represented by the following formula (D):

[Chem. 69]

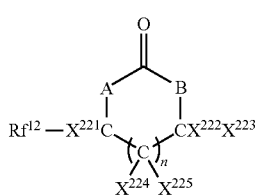

wherein one of A or B is $CX^{226}X^{227}$ (where $X^{226}$ and $X^{227}$ are the same as or different from each other, and are each —H, —F, —Cl, —CF$_3$, —CH$_3$, or an alkylene group in which a hydrogen atom is optionally replaced by a halogen atom and which optionally contains a hetero atom in the chain) and the other is an oxygen atom; Rf$^{12}$ is a fluorinated alkyl group or fluorinated alkoxy group optionally containing an ether bond; $X^{221}$ and $X^{222}$ are the same as or different from each other, and are each —H, —F, —Cl, —CF$_3$, or CH$_3$; $X^{223}$ to $X^{225}$ are the same as or different from each other, and are each —H, —F, —Cl, or an alkyl group in which a hydrogen atom is optionally replaced by a halogen atom and which optionally contains a hetero atom in the chain; and n=0 or 1.

A preferred example of the fluorine-containing lactone represented by the formula (D) is a 5-membered ring structure represented by the following formula (E):

[Chem. 70]

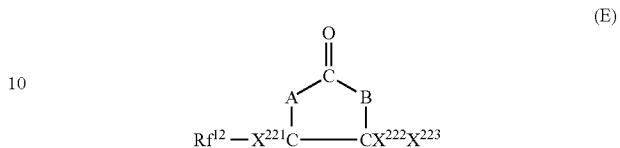

(wherein A, B, Rf$^{12}$, $X^{221}$, $X^{222}$, and $X^{223}$ are defined as in the formula (D)) because it can be easily synthesized and can have good chemical stability. Further, in relation to the combination of A and B, fluorine-containing lactones represented by the following formula (F):

[Chem. 71]

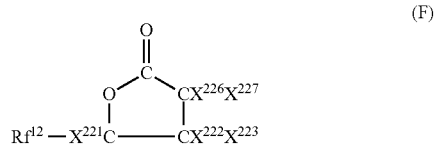

(wherein Rf$^{12}$, $X^{221}$, $X^{222}$, $X^{223}$ $X^{226}$ and $X^{227}$ are defined as in the formula (D)) and fluorine-containing lactones represented by the following formula (G):

[Chem. 72]

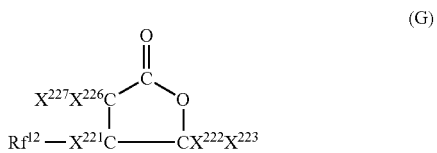

(wherein Rf$^{12}$, $X^{221}$, $X^{222}$, $X^{223}$, $X^{226}$, and $X^{227}$ are defined as in the formula (D)) may be mentioned.

In order to particularly give excellent characteristics such as high permittivity and high withstand voltage, and to improve the characteristics of the electrolyte solution in the invention, for example, to give good solubility of an electrolyte salt and to reduce the internal resistance well, those represented by the following formulae:

[Chem. 73]

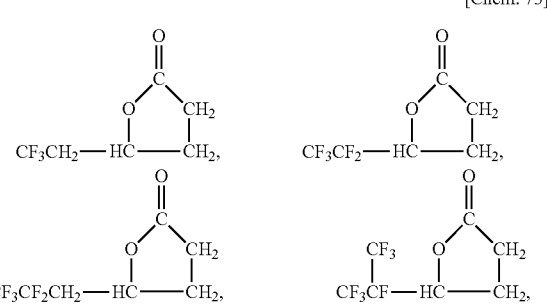

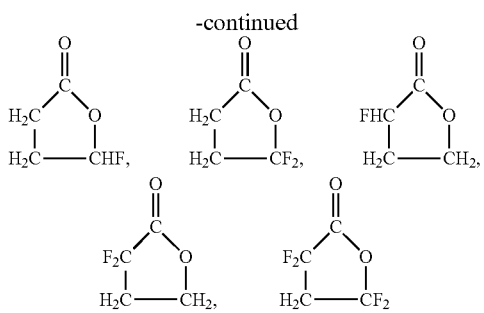

may be mentioned.

The presence of a fluorinated cyclic carboxylate can lead to, for example, effects of improving the ion conductivity, improving the safety, and improving the stability at high temperature.

Examples of the acyclic carboxylate include those having a carbon number of 3 to 7 in total in the structural formula thereof. Specific examples thereof include methyl acetate, ethyl acetate, n-propyl acetate, isopropyl acetate, n-butyl acetate, isobutyl acetate, t-butyl acetate, methyl propionate, ethyl propionate, n-propyl propionate, isobutyl propionate, n-butyl propionate, methyl butyrate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

In order to improve the ion conductivity owing to viscosity reduction, preferred among these are methyl acetate, ethyl acetate, n-propyl acetate, n-butyl acetate, methyl propionate, ethyl propionate, n-propyl propionate, isopropyl propionate, methyl butyrate, and ethyl butyrate.

The ether compound is preferably a C2-C10 acyclic ether or a C3-C6 cyclic ether.

Examples of the C2-C10 acyclic ether include dimethyl ether, diethyl ether, di-n-butyl ether, dimethoxymethane, methoxyethoxymethane, diethoxymethane, dimethoxyethane, methoxyethoxyethane, diethoxyethane, ethylene glycol di-n-propyl ether, ethylene glycol di-n-butyl ether, diethylene glycol, diethylene glycol dimethyl ether, pentaethylene glycol, triethylene glycol dimethyl ether, triethylene glycol, tetraethylene glycol, tetraethylene glycol dimethyl ether, and diisopropyl ether.

Further, the ether compound may also suitably be a fluorinated ether.

An example of the fluorinated ether is a fluorinated ether (I) represented by the following formula (I):

$$Rf^3\text{---}O\text{---}Rf^4 \qquad (I)$$

(wherein $Rf^3$ and $Rf^4$ are the same as or different from each other, and are each a C1-C10 alkyl group or a C1-C10 fluorinated alkyl group; and at least one selected from $Rf^3$ and $Rf^4$ is a fluorinated alkyl group). The presence of the fluorinated ether (I) allows the electrolyte solution to have improved incombustibility as well as improved stability and safety at high temperature under high voltage.

In the formula (I), at least one selected from $Rf^3$ and $Rf^4$ is a C1-C10 fluorinated alkyl group. In order to allow the electrolyte solution to have further improved incombustibility and further improved stability and safety at high temperature under high voltage, both $Rf^3$ and $Rf^4$ are preferably C1-C10 fluorinated alkyl groups. In this case, $Rf^3$ and $Rf^4$ may be the same as or different from each other.

Particularly preferably, $Rf^3$ and $Rf^4$ are the same as or different from each other, and $Rf^3$ is a C3-C6 fluorinated alkyl group and $Rf^4$ is a C2-C6 fluorinated alkyl group.

If the sum of the carbon numbers of $Rf^3$ and $Rf^4$ is too small, the fluorinated ether may have too low a boiling point. Too large a carbon number of $Rf^3$ or $Rf^4$ may cause low solubility of an electrolyte salt, may start to adversely affect the miscibility with other solvents, and may cause high viscosity, resulting in poor rate characteristics. In order to achieve an excellent boiling point and rate characteristics, advantageously, the carbon number of $Rf^3$ is 3 or 4 and the carbon number of $Rf^4$ is 2 or 3.

The fluorinated ether (I) preferably has a fluorine content of 40 to 75% by mass. The fluorinated ether (I) having a fluorine content within this range may lead to particularly excellent balance between the non-flammability and the miscibility. The above range is also preferred for good oxidation resistance and safety.

The lower limit of the fluorine content is more preferably 45% by mass, still more preferably 50% by mass, particularly preferably 55% by mass. The upper limit thereof is more preferably 70% by mass, still more preferably 66% by mass.

The fluorine content of the fluorinated ether (I) is a value calculated based on the structural formula of the fluorinated ether (I) by the following formula:

{(Number of fluorine atoms×19)/(Molecular weight of fluorinated ether(I))}×100(%).

Examples of $Rf^3$ include $CF_3CF_2CH_2\text{---}$, $CF_3CFHCF_2\text{---}$, $HCF_2CF_2CF_2\text{---}$, $HCF_2CF_2CH_2\text{---}$, $CF_3CF_2CH_2CH_2\text{---}$, $CF_3CFHCF_2CH_2\text{---}$, $HCF_2CF_2CF_2CF_2\text{---}$, $HCF_2CF_2CF_2CH_2\text{---}$, $HCF_2CF_2CH_2CH_2\text{---}$, and $HCF_2CF(CF_3)CH_2\text{---}$. Examples of $Rf^4$ include $\text{---}CH_2CF_2CF_3$, $\text{---}CF_2CFHCF_3$, $\text{---}CF_2CF_2CF_2H$, $\text{---}CH_2CF_2CF_2H$, $\text{---}CH_2CH_2CF_2CF_3$, $\text{---}CH_2CF_2CFHCF_3$, $\text{---}CF_2CF_2CF_2CF_2H$, $\text{---}CH_2CF_2CF_2CF_2H$, $\text{---}CH_2CH_2CF_2CF_2H$, $\text{---}CH_2CF(CF_3)CF_2H$, $\text{---}CF_2CF_2H$, $\text{---}CH_2CF_2H$, and $\text{---}CF_2CH_3$.

Specific examples of the fluorinated ether (I) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

In particular, those having $HCF_2\text{---}$ or $CF_3CFH\text{---}$ at one or each end can provide a fluorinated ether (I) having excellent polarizability and a high boiling point. The boiling point of the fluorinated ether (I) is preferably 67° C. to 120° C., more preferably 80° C. or higher, still more preferably 90° C. or higher.

Such a fluorinated ether (I) may include one or two or more of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCF_2CF_2H$, $CF_3CF_2CH_2OCF_2CF_2H$, and the like.

Advantageously, in order to achieve a high boiling point and good miscibility with other solvents and to give good solubility of an electrolyte salt, the fluorinated ether (I) preferably include at least one selected from the group consisting of $HCF_2CF_2CH_2OCF_2CFHCF_3$ (boiling point: 106° C.), $CF_3CF_2CH_2OCF_2CFHCF_3$ (boiling point: 82° C.), $HCF_2CF_2CH_2OCF_2CF_2H$ (boiling point: 92° C.), and $CF_3CF_2CH_2OCF_2CF_2H$ (boiling point: 68° C.), more preferably at least one selected from the group consisting of $HCF_2CF_2CH_2OCF_2CFHCF_3$ (boiling point: 106° C.), and $HCF_2CF_2CH_2OCF_2CF_2H$ (boiling point: 92° C.).

Examples of the $C_3$-$C_6$ cyclic ether include 1,2-dioxane, 1,3-dioxane, 2-methyl-1,3-dioxane, 4-methyl-1,3-dioxane, 1,4-dioxane, metaformaldehyde, 2-methyl-1,3-dioxolane, 1,3-dioxolane, 4-methyl-1,3-dioxolane, 2-(trifluoroethyl)dioxolane, 2,2-bis(trifluoromethyl)-1,3-dioxolane, and fluorinated compounds thereof. In order to achieve a high ability to solvate with lithium ions and improve the degree of ion dissociation, preferred are dimethoxymethane, diethoxymethane, ethoxymethoxymethane, ethylene glycol n-propyl ether, ethylene glycol di-n-butyl ether, diethylene glycol dimethyl ether, and crown ethers. In order to achieve low viscosity and to give a high ion conductivity, particularly preferred are dimethoxymethane, diethoxymethane, and ethoxymethoxymethane.

Examples of the nitrogen-containing compound include nitrile, fluorine-containing nitrile, carboxylic acid amide, fluorine-containing carboxylic acid amide, sulfonic acid amide, fluorine-containing sulfonic acid amide, acetamide, and formamide. Also, 1-methyl-2-pyrrolidinone, 1-methyl-2-piperidone, 3-methyl-2-oxazilidinone, 1,3-dimethyl-2-imidazolidinone, and N-methylsuccinimide may be used. The nitrile compounds represented by the formulae (1a), (1b), and (1c) are not included in the above nitrogen-containing compounds.

Examples of the boron-containing compound include borates such as trimethyl borate and triethyl borate, boric acid ethers, and alkyl borates.

Examples of the organosilicon-containing compound include $(CH_3)_4$—Si, $(CH_3)_3$—Si—Si$(CH_3)_3$, and silicone oil.

Examples of the fireproof agent (flame retardant) include organophosphates and phosphazene-based compounds. Examples of the organophosphates include fluorine-containing alkyl phosphates, non-fluorine-containing alkyl phosphates, and aryl phosphates. In order to achieve a flame retardant effect even in a small amount, fluorine-containing alkyl phosphates are particularly preferred.

Examples of the phosphazene-based compounds include methoxypentafluorocyclotriphosphazene, phenoxypentafluorocyclotriphosphazene, dimethylaminopentafluorocyclotriphosphazene, diethylaminopentafluorocyclotriphosphazene, ethoxypentafluorocyclotriphosphazene, and ethoxyheptafluorocyclotetraphosphazene.

Specific examples of the fluorine-containing alkyl phosphates include fluorine-containing dialkyl phosphates disclosed in JP H11-233141 A, cyclic alkyl phosphates disclosed in JP H11-283669 A, and fluorine-containing trialkyl phosphates.

Preferred examples of the fireproof agent (flame retardant) include $(CH_3O)_3P\!=\!O$, $(CF_3CH_2O)_3P\!=\!O$, $(HCF_2CH_2O)_3P\!=\!O$, $(CF_3CF_2CH_2)_3P\!=\!O$, and $(HCF_2CF_2CH_2)_3P\!=\!O$.

The surfactant may be any of cationic surfactants, anionic surfactants, nonionic surfactants, and amphoteric surfactants. In order to give good cycle characteristics and rate characteristics, the surfactant is preferably one containing a fluorine atom.

Preferred examples of such a surfactant containing a fluorine atom include fluorine-containing carboxylic acid salts represented by the following formula (30):

$$Rf^5COO^-M^+ \tag{30}$$

(wherein $Rf^5$ is a $C_3$-$C_{10}$ fluorine-containing alkyl group optionally containing an ether bond; $M^+$ is $Li^+$, $Na^+$, $K^+$, or $NHR'_3{}^+$, wherein R's are the same as or different from each other, and are each H or a C1-C3 alkyl group), and fluorine-containing sulfonic acid salts represented by the following formula (40):

$$Rf^6SO_3^-M^+ \tag{40}$$

(wherein $Rf^6$ is a C3-C10 fluorine-containing alkyl group optionally containing an ether bond; $M^+$ is $Li^+$, $Na^+$, $K^+$, or $NHR'_3{}^+$, wherein R's are the same as or different from each other, and are each H or a C1-C3 alkyl group).

In order to reduce the surface tension of the electrolyte solution without impairing the charge and discharge cycle characteristics, the surfactant is preferably present in an amount of 0.01 to 2% by mass of the electrolyte solution.

Examples of the additive for increasing the permittivity include sulfolane, methylsulfolane, γ-butyrolactone, and γ-valerolactone.

Examples of the improver for cycle characteristics and rate characteristics include methyl acetate, ethyl acetate, tetrahydrofuran, and 1,4-dioxane.

The electrolyte solution of the invention may be combined with a polymer material and thereby formed into a gel-like (plasticized), gel electrolyte solution.

Examples of such a polymer material include conventionally known polyethylene oxide and polypropylene oxide, and modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); and composites of any of these fluororesins and any hydrocarbon resin (see JP H11-35765 A, JP H11-86630 A) In particular, polyvinylidene fluoride or a vinylidene fluoride-hexafluoropropylene copolymer is preferably used as a polymer material for a gel electrolyte.

The electrolyte solution of the invention may also contain an ion conductive compound disclosed in Japanese Patent Application No. 2004-301934.

This ion conductive compound is an amorphous fluorine-containing polyether compound having a fluorine-containing group at a side chain and is represented by the following formula (101):

$$A\text{-}(D)\text{-}B \tag{101}$$

wherein D is represented by the following formula (201):

$$\text{-}(D1)_n\text{-}(FAE)_m\text{-}(AE)_p\text{-}(Y)_q\text{-} \tag{201}$$

[wherein D1 is an ether unit containing a fluorine-containing ether group at a side chain and is represented by the following formula (2a):

[Chem. 74]

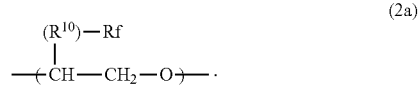

(2a)

(wherein Rf is a fluorine-containing ether group optionally containing a crosslinkable functional group; and $R^{10}$ is a group or a bond that links Rf and the main chain);

FAE is an ether unit containing a fluorinated alkyl group at a side chain and is represented by the following formula (2b):

[Chem. 75]

(2b)

(wherein Rfa is a hydrogen atom or a fluorinated alkyl group optionally containing a crosslinkable functional group; and $R^{11}$ is a group or a bond that links Rfa and the main chain);

AE is an ether unit represented by the following formula (2c):

[Chem. 76]

(2c)

(wherein $R^{13}$ is a hydrogen atom, an alkyl group optionally containing a crosslinkable functional group, an aliphatic cyclic hydrocarbon group optionally containing a crosslinkable functional group, or an aromatic hydrocarbon group optionally containing a crosslinkable functional group; and $R^{12}$ is a group or a bond that links $R^{13}$ and the main chain);

Y is a unit containing at least one selected from the following formulae (2d-1) to (2d-3):

[Chem. 77]

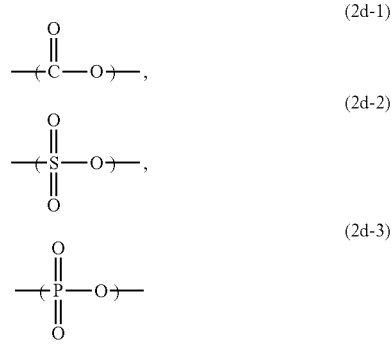

n is an integer of 0 to 200;
m is an integer of 0 to 200;
p is an integer of 0 to 10000;
q is an integer of 1 to 100;
n+m is not 0; and
the bonding order of D1, FAE, AE, and Y is not specified]; and A and B are the same as or different from each other, and are each a hydrogen atom, an alkyl group optionally containing a fluorine atom and/or a crosslinkable functional group, a phenyl group optionally containing a fluorine atom and/or a crosslinkable functional group, a —COOH group, —OR (where R is a hydrogen atom or an alkyl group optionally containing a fluorine atom and/or a crosslinkable functional group), an ester group, or a carbonate group, and when an end of D is an oxygen atom, A and B are each none of a —COOH group, —OR, an ester group, and a carbonate group.

The electrolyte solution of the invention may contain a sulfone-based compound. Preferred as the sulfone-based compound are a C3-C6 cyclic sulfone and a C2-C6 acyclic sulfone. The number of sulfonyl groups in one molecule is preferably 1 or 2.

Examples of the cyclic sulfone include monosulfone compounds such as trimethylene sulfones, tetramethylene sulfones, and hexamethylene sulfones; disulfone compounds such as trimethylene disulfones, tetramethylene disulfones, and hexamethylene disulfones. In order to give good permittivity and viscosity, more preferred among these are tetramethylene sulfones, tetramethylene disulfones, hexamethylene sulfones, and hexamethylene disulfones, particularly preferred are tetramethylene sulfones (sulfolanes).

The sulfolanes are preferably sulfolane and/or sulfolane derivatives (hereinafter, also abbreviated as "sulfolanes" including sulfolane). The sulfolane derivatives are preferably those in which one or more hydrogen atoms binding to any carbon atom constituting the sulfolane ring is replaced by a fluorine atom or an alkyl group.

In order to achieve high ion conductivity and high input and output, preferred among these are 2-methylsulfolane, 3-methylsulfolane, 2-fluorosulfolane, 3-fluorosulfolane, 2,2-difluorosulfolane, 2,3-difluorosulfolane, 2,4-difluorosulfolane, 2,5-difluorosulfolane, 3,4-difluorosulfolane, 2-fluoro-3-methylsulfolane, 2-fluoro-2-methylsulfolane, 3-fluoro-3-methylsulfolane, 3-fluoro-2-methylsulfolane, 4-fluoro-3-methylsulfolane, 4-fluoro-2-methylsulfolane, 5-fluoro-3-methylsulfolane, 5-fluoro-2-methylsulfolane, 2-fluoromethylsulfolane, 3-fluoromethylsulfolane, 2-difluoromethylsulfolane, 3-difluoromethylsulfolane, 2-trifluoromethylsulfolane, 3-trifluoromethylsulfolane, 2-fluoro-3-(trifluoromethyl)sulfolane, 3-fluoro-3-(trifluoromethyl)sulfolane, 4-fluoro-3-(trifluoromethyl)sulfolane, 3-sulfolene, 5-fluoro-3-(trifluoromethyl)sulfolane, and the like.

Examples of the acyclic sulfone include dimethyl sulfone, ethyl methyl sulfone, diethyl sulfone, n-propyl methyl sulfone, n-propyl ethyl sulfone, di-n-propyl sulfone, isopropyl methyl sulfone, isopropyl ethyl sulfone, diisopropyl sulfone, n-butyl methyl sulfone, n-butyl ethyl sulfone, t-butyl methyl sulfone, t-butyl ethyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethyl monofluoromethyl sulfone, ethyl difluoromethyl sulfone, ethyl trifluoromethyl sulfone, perfluoroethyl methyl sulfone, ethyl trifluoroethyl sulfone, ethyl pentafluoroethyl sulfone, di(trifluoroethyl)sulfone, perfluorodiethyl sulfone, fluoromethyl-n-propyl sulfone, difluoromethyl-n-propyl sulfone, trifluoromethyl-n-propyl sulfone, fluoromethyl isopropyl sulfone, difluoromethyl isopropyl sulfone, trifluoromethyl isopropyl sulfone, trifluoroethyl-n-propyl sulfone, trifluoroethyl isopropyl sulfone, pentafluoroethyl-n-propyl sulfone, pentafluoroethyl isopropyl sulfone, trifluoroethyl-n-butyl sulfone, trifluoroethyl-t-butyl sulfone, pentafluoroethyl-n-butyl sulfone, and pentafluoroethyl-t-butyl sulfone.

In order to achieve high ion conductivity and high input and output, preferred among these are dimethyl sulfone, ethyl methyl sulfone, diethyl sulfone, n-propyl methyl sulfone, isopropyl methyl sulfone, n-butyl methyl sulfone, t-butyl methyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethyl monofluoromethyl sulfone, ethyl difluoromethyl sulfone, ethyl trifluoromethyl sulfone, ethyl pentafluoroethyl sulfone, trifluoromethyl-n-propyl sulfone, trifluoromethyl isopropyl sulfone, trifluoroethyl-n-butyl sulfone, trifluoroethyl-t-butyl sulfone, trifluoromethyl-n-butyl sulfone, trifluoromethyl-t-butyl sulfone, and the like.

The sulfone-based compound may be present in any amount that does not significantly impair the effects of the invention. The amount is usually 0.3% by volume or more, preferably 0.5% by volume or more, more preferably 1% by volume or more, while usually 40% by volume or less, preferably 35% by volume or less, more preferably 30% by volume or less, in 100% by volume of the solvent. The sulfone-based compound in an amount within the above range can easily achieve an effect of improving the cycle characteristics and the durability such as storage characteristics, can lead to an appropriate range of the viscosity of a non-aqueous electrolyte solution, can eliminate a reduction in electric conductivity, and can lead to appropriate ranges of the input and output characteristics and charge and discharge rate characteristics of a non-aqueous electrolyte secondary battery.

The electrolyte solution of the invention may further contain a different additive, if necessary. Examples of the different additive include metal oxides and glass.

The electrolyte solution of the invention preferably contains 5 to 200 ppm of hydrogen fluoride (HF). The presence of HF can promote formation of a film of the aforementioned additive. Too small an amount of HF tends to impair the ability to form a film on the negative electrode, impairing the characteristics of an electrochemical device. Too large an amount of HF tends to impair the oxidation resistance of the electrolyte solution due to the influence by HF. The electrolyte solution of the invention, even when containing HF in an amount within the above range, causes no reduction in the recovery capacity ratio of the battery after high-temperature storage of an electrochemical device.

The amount of HF is more preferably 10 ppm or more, still more preferably 20 ppm or more. The amount of HF is also more preferably 100 ppm or less, still more preferably 80 ppm or less, particularly preferably 50 ppm or less.

The amount of HF can be determined by neutralization titration.

The electrolyte solution of the invention is preferably prepared by any method using the aforementioned components.

The electrolyte solution of the invention is an electrolyte solution used for a lithium ion secondary battery.

The invention also relates to a lithium ion secondary battery containing the electrolyte solution of the invention. The lithium ion secondary battery of the invention has low resistance and excellent cycle characteristics.

The lithium ion secondary battery of the invention includes a positive electrode, a negative electrode, and the aforementioned electrolyte solution.

<Positive Electrode>

The positive electrode includes a positive electrode active material layer containing a positive electrode active material and a current collector.

The positive electrode active material may be any material that can electrochemically occlude and release lithium ions. Examples thereof include lithium-containing transition metal complex oxides, lithium-containing transition metal phosphoric acid compounds, sulfides, and conductive polymers. Preferred among these as the positive electrode active material are lithium-containing transition metal complex oxides and lithium-containing transition metal phosphoric acid compounds. Particularly preferred is a lithium-containing transition metal complex oxide that generates high voltage.

The transition metal of the lithium-containing transition metal complex oxide is preferably V, Ti, Cr, Mn, Fe, Co, Ni, Cu, or the like. Specific examples thereof include lithium-cobalt complex oxides such as $LiCoO_2$, lithium-nickel complex oxides such as $LiNiO_2$, lithium-manganese complex oxides such as $LiMnO_2$, $LiMn_2O_4$, and $Li_2MnO_4$, and those obtained by substituting some of transition metal atoms as main components of these lithium transition metal complex oxides with another element such as Na, K, B, F, Al, Ti, V, Cr, Mn, Fe, Co, Li, Ni, Cu, Zn, Mg, Ga, Zr, Si, Nb, Mo, Sn, or W. Specific examples of those obtained by substitution include $LiNi_{0.5}Mn_{0.5}O_2$, $LiNi_{0.85}Co_{0.10}Al_{0.05}O_2$, $LiNi_{0.5}Co_{0.2}Mn_{0.3}O_2$, $LiNi_{0.6}Co_{0.2}Mn_{0.2}O_2$, $LiNi_{0.33}Co_{0.33}Mn_{0.33}O_2$, $LiNi_{0.45}Co_{0.10}Al_{0.45}O_2$, $LiMn_{1.8}Al_{0.2}O_4$, and $LiMn_{1.5}Ni_{0.5}O_4$.

The lithium-containing transition metal complex oxide is preferably any of $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$ each of which has a high energy density even at high voltage.

The transition metal of the lithium-containing transition metal phosphoric acid compound is preferably V, Ti, Cr, Mn, Fe, Co, Ni, Cu, or the like. Specific examples thereof include iron phosphates such as $LiFePO_4$, $Li_3Fe_2(PO_4)_3$, and $LiFeP_2O_7$, cobalt phosphates such as $LiCoPO_4$, and those obtained by substituting some of transition metal atoms as main components of these lithium transition metal phosphoric acid compounds with another element such as Al, Ti, V, Cr, Mn, Fe, Co, Li, Ni, Cu, Zn, Mg, Ga, Zr, Nb, or Si.

Examples of the lithium-containing transition metal complex oxide include lithium-manganese spinel complex oxides represented by the formula: $Li_aMn_{2-b}M^1{}_bO_4$ (wherein $0.9 \le a$; $0 \le b \le 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge), lithium-nickel complex oxides represented by the formula: $LiNi_{1-c}M^2{}_cO_2$ (wherein $0 \le c \le 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge), and lithium-cobalt complex oxides represented by the formula: $LiCo_{1-d}M^3{}_dO_2$ (wherein $0 \le d \le 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge).

In order to provide a high-power lithium ion secondary battery having a high energy density, preferred is $LiCoO_2$, $LiMnO_2$, $LiNiO_2$, $LiMn_2O_4$, $LiNi_{0.5}Co_{0.15}Al_{0.05}O_2$, or $LiNi_{1/3}Co_{1/3}Mn_{1/3}O_2$.

Other examples of the positive electrode active material include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

Examples of the sulfides include compounds having a 2D lamellar structure such as $TiS_2$ and $MoS_2$, and chevrel compounds having a strong 3D skeletal structure such as those represented by the formula: $Me_xMo_6S_8$ (wherein Me is a transition metal such as Pb, Ag, and Cu). Examples thereof also include simple sulfur and organolithium sulfides represented by $LiS_x$.

Examples of the conductive polymers include p-doped conductive polymers and n-doped conductive polymers. Examples of the conductive polymers include polyacetylene-based polymers, polyphenylene-based polymers, heterocyclic polymers, ionic polymers, ladder-shaped polymers, and network polymers.

In order to improve the continuous charge characteristics, the positive electrode active material preferably contains lithium phosphate. Lithium phosphate may be used in any manner, and is preferably used in admixture with the positive electrode active material. The lower limit of the amount of lithium phosphate used is preferably 0.1% by mass or more, more preferably 0.3% by mass or more, still more preferably 0.5% by mass or more, relative to the sum of the amounts of the positive electrode active material and lithium phosphate. The upper limit thereof is preferably 10% by mass or less, more preferably 8% by mass or less, still more preferably 5% by mass or less.

To a surface of the positive electrode active material may be attached a substance having a composition different from the positive electrode active material. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

Such a substance may be attached to a surface of the positive electrode active material by, for example, a method of dissolving or suspending the substance in a solvent, impregnating the solution or suspension into the positive electrode active material, and drying the impregnated material; a method of dissolving or suspending a precursor of the substance in a solvent, impregnating the solution or suspension into the positive electrode active material, and heating the material and the precursor to cause a reaction therebetween; or a method of adding the substance to a precursor of the positive electrode active material and simultaneously sintering the materials. In the case of attaching carbon, for example, a carbonaceous material in the form of activated carbon may be mechanically attached to the surface afterward.

For the amount of the substance attached to the surface in terms of the mass relative to the amount of the positive electrode active material, the lower limit thereof is preferably 0.1 ppm or more, more preferably 1 ppm or more, still more preferably 10 ppm or more, while the upper limit thereof is preferably 20% or less, more preferably 10% or less, still more preferably 5% or less. The substance attached to the surface can reduce oxidation of the electrolyte solution on the surface of the positive electrode active material, improving the battery life. Too small an amount of the substance may fail to sufficiently provide this effect. Too large an amount thereof may hinder the entrance and exit of lithium ions, increasing the resistance.

Particles of the positive electrode active material may have any shape conventionally used, such as a bulky shape, a polyhedral shape, a spherical shape, an ellipsoidal shape, a plate shape, a needle shape, or a pillar shape. The primary particles may agglomerate to form secondary particles.

The positive electrode active material has a tap density of preferably 0.5 g/cm$^3$ or higher, more preferably 0.8 g/cm$^3$ or higher, still more preferably 1.0 g/cm$^3$ or higher. The positive electrode active material having a tap density below the lower limit may cause an increased amount of a dispersion medium required and increased amounts of a conductive material and a binder required in formation of the positive electrode active material layer, as well as limitation on the packing fraction of the positive electrode active material in the positive electrode active material layer, resulting in limitation on the battery capacity. A complex oxide powder having a high tap density enables formation of a positive electrode active material layer with a high density. The tap density is preferably as high as possible and has no upper limit, in general. Still, too high a tap density may cause diffusion of lithium ions in the positive electrode active material layer with the electrolyte solution serving as a diffusion medium to function as a rate-determining step, easily impairing the load characteristics. Thus, the upper limit of the tap density is preferably 4.0 g/cm$^3$ or lower, more preferably 3.7 g/cm$^3$ or lower, still more preferably 3.5 g/cm$^3$ or lower.

In the invention, the tap density is determined as a powder packing density (tap density) g/cm$^3$ when 5 to 10 g of the positive electrode active material powder is packed into a 10-ml glass graduated cylinder and the cylinder is tapped 200 times with a stroke of about 20 mm.

The particles of the positive electrode active material have a median size d50 (or a secondary particle size when the primary particles agglomerate to form secondary particles) of preferably 0.3 μm or greater, more preferably 0.5 μm or greater, still more preferably 0.8 μm or greater, most preferably 1.0 μm or greater, while preferably 30 μm or smaller, more preferably 27 μm or smaller, still more preferably 25 μm or smaller, most preferably 22 μm or smaller. The particles having a median size below the lower limit may fail to provide a product with a high tap density. The particles having a median size greater than the upper limit may cause prolonged diffusion of lithium in the particles, impairing the battery performance and generating streaks in formation of the positive electrode for a battery, i.e., when the active material and components such as a conductive material and a binder are formed into slurry by adding a solvent and the slurry is applied in the form of a film, for example. Mixing two or more positive electrode active materials having different median sizes d50 can further improve the easiness of packing in formation of the positive electrode.

In the invention, the median size d50 is determined using a known laser diffraction/scattering particle size distribution analyzer. In the case of using LA-920 (Horiba, Ltd.) as the particle size distribution analyzer, the dispersion medium used in the measurement is a 0.1% by mass sodium hexametaphosphate aqueous solution and the measurement refractive index is set to 1.24 after 5-minute ultrasonic dispersion.

When the primary particles agglomerate to form secondary particles, the average primary particle size of the positive electrode active material is preferably 0.05 μm or greater, more preferably 0.1 μm or greater, still more preferably 0.2 μm or greater. The upper limit thereof is preferably 5 μm or smaller, more preferably 4 μm or smaller, still more preferably 3 μm or smaller, most preferably 2 μm or smaller. The primary particles having an average primary particle size greater than the upper limit may have difficulty in forming spherical secondary particles, adversely affecting the powder packing. Further, such primary particles may have a greatly reduced specific surface area, highly possibly impairing the battery performance such as output characteristics. In contrast, the primary particles having an average primary particle size below the lower limit may usually be insufficiently grown crystals, causing poor charge and discharge reversibility, for example.

In the invention, the primary particle size is measured by scanning electron microscopic (SEM) observation. Specifically, the primary particle size is determined as follows. A photograph at a magnification of 10000× is first taken. Any 50 primary particles are selected and the maximum length between the left and right boundary lines of each primary particle is measured along the horizontal line. Then, the average value of the maximum lengths is calculated, which is defined as the primary particle size.

The positive electrode active material has a BET specific surface area of preferably 0.1 m$^2$/g or larger, more preferably 0.2 m$^2$/g or larger, still more preferably 0.3 m$^2$/g or larger. The upper limit thereof is preferably 50 m$^2$/g or smaller, more preferably 40 m$^2$/g or smaller, still more preferably 30 m$^2$/g or smaller. The positive electrode active material having a BET specific surface area smaller than the above range may easily impair the battery performance. The positive electrode active material having a BET specific surface area larger than the above range may less easily have an increased tap density, easily causing a difficulty in applying the material in formation of the positive electrode active material layer.

In the invention, the BET specific surface area is defined by a value determined by single point BET nitrogen adsorption utilizing a gas flow method using a surface area analyzer (e.g., fully automatic surface area measurement device, Ohkura Riken Co., Ltd.), a sample pre-dried in nitrogen stream at 150° C. for 30 minutes, and a nitrogen-helium gas mixture with the nitrogen pressure relative to the atmospheric pressure being accurately adjusted to 0.3.

When the lithium ion secondary battery of the invention is used as a large-size lithium ion secondary battery for hybrid vehicles or distributed generation, it needs to achieve high output. Thus, the particles of the positive electrode active material preferably mainly composed of secondary particles.

The particles of the positive electrode active material preferably include 0.5 to 7.0% by volume of fine particles having an average secondary particle size of 40 μm or smaller and having an average primary particle size of 1 μm or smaller. The presence of fine particles having an average primary particle size of 1 μm or smaller enlarges the contact area with the electrolyte solution and enables more rapid diffusion of lithium ions between the electrode and the electrolyte solution, improving the output performance of the battery.

The positive electrode active material may be produced by any usual method of producing an inorganic compound. In particular, a spherical or ellipsoidal active material can be produced by various methods. For example, a material substance of transition metal is dissolved or crushed and dispersed in a solvent such as water, and the pH of the solution or dispersion is adjusted under stirring to form a spherical precursor. The precursor is recovered and, if necessary, dried. Then, a Li source such as LiOH, Li$_2$CO$_3$, or LiNO$_3$ is added thereto and the mixture is sintered at high temperature, thereby providing an active material.

In production of the positive electrode, the aforementioned positive electrode active materials may be used alone or in any combination of two or more thereof having different compositions at any ratio. Preferred examples of the combination in this case include a combination of LiCoO$_2$ and LiMn$_2$O$_4$ in which part of Mn may optionally be replaced by a different transition metal (e.g., LiNi$_{0.33}$Co$_{0.33}$Mn$_{0.33}$O$_2$), and a combination with LiCoO$_2$ in which part of Co may optionally be replaced by a different transition metal.

In order to achieve a high battery capacity, the amount of the positive electrode active material is preferably 50 to 99.5% by mass, more preferably 80 to 99% by mass, of the positive electrode mixture. The amount of the positive electrode active material in the positive electrode active material layer is preferably 80% by mass or more, more preferably 82% by mass or more, particularly preferably 84% by mass or more. The upper limit thereof is preferably 99% by mass or less, more preferably 98% by mass or less. Too small an amount of the positive electrode active material in the positive electrode active material layer may cause an insufficient electric capacity. In contrast, too large an amount thereof may cause insufficient strength of the positive electrode.

The positive electrode mixture preferably further contains a binder, a thickening agent, and a conductive material.

The binder may be any material that is safe against a solvent to be used in production of the electrode and the electrolyte solution. Examples thereof include resin polymers such as polyethylene, polypropylene, polyethylene terephthalate, polymethyl methacrylate, aromatic polyamide, chitosan, alginic acid, polyacrylic acid, polyimide, cellulose, and nitro cellulose; rubbery polymers such as SBR (styrene-butadiene rubber), isoprene rubber, butadiene rubber, fluoroelastomers, NBR (acrylonitrile-butadiene rubber), and ethylene-propylene rubber; styrene-butadiene-styrene block copolymers and hydrogenated products thereof; thermoplastic elastomeric polymers such as EPDM (ethylene-propylene-diene terpolymers), styrene-ethylene-butadiene-styrene copolymers, and styrene-isoprene-styrene block copolymers and hydrogenated products thereof; soft resin polymers such as syndiotactic-1,2-polybutadiene, polyvinyl acetate, ethylene-vinyl acetate copolymers, and propylene-α-olefin copolymers; fluoropolymers such as polyvinylidene fluoride, polytetrafluoroethylene, vinylidene fluoride copolymer, and tetrafluoroethylene-ethylene copolymers; and polymer compositions having ion conductivity of alkali metal ions (especially, lithium ions). These may be used alone or in any combination of two or more at any ratio.

The amount of the binder, which is expressed as the proportion of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, polyvinylpyrrolidone, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, Ketjen black, channel black, furnace black, lamp black, and thermal black, and amorphous carbon, including needle coke, carbon nanotube, fullerene, and VGCF. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, the conductive material in an amount more than the above range may cause a low battery capacity.

The solvent for forming slurry may be any solvent that can dissolve or disperse therein the positive electrode active material, the conductive material, and the binder, as well as a thickening agent used as appropriate. The solvent may be either an aqueous solvent or an organic solvent. Examples of the aqueous medium include water and solvent mixtures of an alcohol and water. Examples of the organic medium include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropylamine; ethers such as diethyl ether, propylene oxide, and tetrahydrofuran (THF); amides such as N-methylpyrrolidone (NMP), dimethyl formamide, and dimethyl acetamide; and aprotic polar solvents such as hexamethyl phospharamide and dimethyl sulfoxide.

Examples of the material of the current collector for a positive electrode include metal materials such as aluminum, titanium, tantalum, stainless steel, and nickel, and alloys thereof; and carbon materials such as carbon cloth and carbon paper. Preferred is any metal material, especially aluminum or an alloy thereof.

In the case of a metal material, the current collector may be in the form of metal foil, metal cylinder, metal coil, metal plate, metal film, expanded metal, punched metal, metal foam, or the like. In the case of a carbon material, it may be in the form of carbon plate, carbon film, carbon cylinder, or the like. Preferred among these is a metal film. The film may be in the form of mesh, as appropriate. The film may have any thickness, and the thickness is usually 1 µm or greater, preferably 3 µm or greater, more preferably 5 µm or greater, while usually 1 mm or smaller, preferably 100 µm or smaller, more preferably 50 µm or smaller. The film having a thickness smaller than the above range may have insufficient strength as a current collector. In contrast, the film having a thickness greater than the above range may have poor handleability.

In order to reduce the electric contact resistance between the current collector and the positive electrode active material layer, the current collector also preferably has a conductive aid applied on the surface thereof. Examples of the conductive aid include carbon and noble metals such as gold, platinum, and silver.

The ratio between the thicknesses of the current collector and the positive electrode active material layer may be any value, and the ratio {(thickness of positive electrode active material layer on one side immediately before injection of electrolyte solution)/(thickness of current collector)} is preferably 20 or lower, more preferably 15 or lower, most preferably 10 or lower. The ratio is also preferably 0.5 or higher, more preferably 0.8 or higher, most preferably 1 or higher. The current collector and the positive electrode active material layer showing a ratio higher than the above range may cause the current collector to generate heat due to Joule heating during high-current-density charge and discharge. The current collector and the positive electrode active material layer showing a ratio lower than the above range may cause an increased ratio by volume of the current collector to the positive electrode active material, reducing the battery capacity.

The positive electrode may be produced by a usual method. An example of the production method is a method in which the positive electrode active material is mixed with the aforementioned binder, thickening agent, conductive material, solvent, and other components to form a slurry-like positive electrode mixture, and then this mixture is applied to a current collector, dried, and pressed so as to be densified.

The densification may be achieved using a manual press or a roll press, for example. The density of the positive electrode active material layer is preferably 1.5 g/cm$^3$ or higher, more preferably 2 g/cm$^3$ or higher, still more preferably 2.2 g/cm$^3$ or higher, while preferably 5 g/cm$^3$ or lower, more preferably 4.5 g/cm$^3$ or lower, still more preferably 4 g/cm$^3$ or lower. The positive electrode active material layer having a density higher than the above range may cause low permeability of the electrolyte solution toward the vicinity of the interface between the current collector and the active material, and poor charge and discharge characteristics particularly at a high current density, failing to provide high output. The positive electrode active material layer having a density lower than the above range may cause poor conductivity between the active materials and increase the battery resistance, failing to provide high output.

In order to improve the stability at high output and high temperature in the case of using the electrolyte solution of the invention, the area of the positive electrode active material layer is preferably large relative to the outer surface area of an external case of the battery. Specifically, the total area of the positive electrode is preferably 15 times or more, more preferably 40 times or more, greater than the surface area of the external case of the secondary battery. For closed, square-shaped cases, the outer surface area of an external case of the battery herein means the total area calculated from the dimensions of length, width, and thickness of the case portion into which a power-generating element is packed except for a protruding portion of a terminal. For closed, cylinder-like cases, the outer surface area of an external case of the battery herein means the geometric surface area of an approximated cylinder of the case portion into which a power-generating element is packed except for a protruding portion of a terminal. The total area of the positive electrode herein means the geometric surface area of the positive electrode mixture layer opposite to a mixture layer including the negative electrode active material. For structures including a current collector foil and positive electrode mixture layers on both sides of the current collector, the total area of the positive electrode is the sum of the areas calculated on the respective sides.

The positive electrode plate may have any thickness. In order to achieve a high capacity and high output, the lower limit of the thickness of the mixture layer on one side of the current collector excluding the thickness of the base metal foil is preferably 10 µm or greater, more preferably 20 µm or greater, while preferably 500 µm or smaller, more preferably 450 µm or smaller.

To a surface of the positive electrode plate may be attached a substance having a composition different from the positive electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

<Negative Electrode>

The negative electrode includes a negative electrode active material layer containing a negative electrode active material and a current collector.

The negative electrode material may be any one that can electrochemically occlude and release lithium ions. Specific examples thereof include carbon materials, alloyed materials, lithium-containing metal complex oxide materials, and conductive polymers. These may be used alone or two or more thereof may be used in any combination.

Examples of the negative electrode active material include carbonaceous materials that can occlude and release lithium such as pyrolysates of organic matter under various pyrolysis conditions, artificial graphite, and natural graphite; metal oxide materials that can occlude and release lithium such as tin oxide and silicon oxide; lithium metals; various lithium alloys; and lithium-containing metal complex oxide materials. Two or more of these negative electrode active materials may be used in admixture with each other.

The carbonaceous material that can occlude and release lithium is preferably artificial graphite produced by high-temperature treatment of easily graphitizable pitch from various materials, purified natural graphite, or a material obtained by surface treatment on such graphite with pitch or other organic matter and then carbonization of the surface-treated graphite. In order to achieve a good balance between the initial irreversible capacity and the high-current-density charge and discharge characteristics, the carbonaceous material is more preferably selected from carbonaceous materials obtained by heat-treating natural graphite, artificial graphite, artificial carbonaceous substances, or artificial graphite substances at 400° C. to 3200° C. once or more; carbonaceous materials which allow the negative electrode active material layer to include at least two or more carbonaceous matters having different crystallinities and/or have an interface between the carbonaceous matters having the different crystallinities; and carbonaceous materials which allow the negative electrode active material layer to have an interface between at least two or more carbonaceous matters having different orientations. These carbonaceous materials may be used alone or in any combination of two or more at any ratio.

Examples of the carbonaceous materials obtained by heat-treating artificial carbonaceous substances or artificial graphite substances at 400° C. to 3200° C. once or more include coal-based coke, petroleum-based coke, coal-based pitch, petroleum-based pitch, and those prepared by oxidizing these pitches; needle coke, pitch coke, and carbon materials prepared by partially graphitizing these cokes; pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The metal material (excluding lithium-titanium complex oxides) to be used as the negative electrode active material may be any compound that can occlude and release lithium, and examples thereof include simple lithium, simple metals and alloys that constitute lithium alloys, and oxides, carbides, nitrides, silicides, sulfides, and phosphides thereof. The simple metals and alloys constituting lithium alloys are preferably materials containing any of metal and semi-metal elements in Groups 13 and 14, more preferably simple metal of aluminum, silicon, and tin (hereinafter, referred to as "specific metal elements"), and alloys and compounds containing any of these atoms. These materials may be used alone or in combination of two or more at any ratio.

Examples of the negative electrode active material containing at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of the compounds. Such a simple metal, alloy, or metal compound used as the negative electrode active material can lead to a high-capacity battery.

Examples thereof further include compounds in which any of the above composite compounds are complexly bonded with several elements such as simple metals, alloys, and nonmetal elements. Specifically, in the case of silicon or tin, for example, an alloy of this element and a metal that does not serve as a negative electrode may be used. In the case of tin, for example, a composite compound including a combination of 5 or 6 elements, including tin, a metal (excluding silicon) that serves as a negative electrode, a metal that does not serve as a negative electrode, and a nonmetal element, may be used.

Specific examples thereof include simple Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_6Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiO_v$ ($0<v\le2$), LiSiO, simple tin, $SnSiO_3$, LiSnO, $Mg_2Sn$, and $SnO_w$ ($0<w\le2$).

Examples thereof further include composite materials of Si or Sn used as a first constitutional element, and second and third constitutional elements. The second constitutional element is at least one selected from cobalt, iron, magnesium, titanium, vanadium, chromium, manganese, nickel, copper, zinc, gallium, and zirconium, for example. The third constitutional element is at least one selected from boron, carbon, aluminum, and phosphorus, for example.

In order to achieve a high battery capacity and excellent battery characteristics, the metal material is preferably simple silicon or tin (which may contain trace impurities), $SiO_v$ ($0<v\le2$), $SnO_w$ ($0\le w\le2$), a Si—Co—C composite material, a Si—Ni—C composite material, a Sn—Co—C composite material, or a Sn—Ni—C composite material.

The lithium-containing metal complex oxide material to be used as the negative electrode active material may be any material that can occlude and release lithium. In order to achieve good high-current-density charge and discharge characteristics, materials containing titanium and lithium are preferred, lithium-containing metal complex oxide materials containing titanium are more preferred, and complex oxides of lithium and titanium (hereinafter, abbreviated as "lithium titanium complex oxides") are still more preferred. In other words, use of a spinel-structured lithium titanium complex oxide in the negative electrode active material for an electrolyte battery is particularly preferred because this can markedly reduce the output resistance.

Preferred examples of the lithium titanium complex oxides include compounds represented by the following formula:

$$Li_xTi_yM_zO_4$$

wherein M is at least one element selected from the group consisting of Na, K, Co, Al, Fe, Ti, Mg, Cr, Ga, Cu, Zn, and Nb.

In order to achieve a good balance of the battery performance, particularly preferred among the above compositions are those satisfying any of the following:
(i) $1.2 \leq x \leq 1.4$, $1.5 \leq y \leq 1.7$, $z=0$
(ii) $0.9 \leq x \leq 1.1$, $1.9 \leq y \leq 2.1$, $z=0$
(iii) $0.7 \leq x \leq 0.9$, $2.1 \leq y \leq 2.3$, $z=0$.

Particularly preferred representative composition of the compound is $Li_{4/3}Ti_{5/3}O_4$ corresponding to the composition (i), $Li_1Ti_2O_4$ corresponding to the composition (ii), and $Li_{4/5}Ti_{11/5}O_4$ corresponding to the composition (iii). Preferred examples of the structure satisfying $Z \neq 0$ include $Li_{4/3}Ti_{4/3}Al_{1/3}O_4$.

The negative electrode mixture preferably further contains a binder, a thickening agent, and a conductive material.

Examples of the binder include the same binders as those mentioned for the positive electrode. The proportion of the binder is preferably 0.1% by mass or more, more preferably 0.5% by mass or more, particularly preferably 0.6% by mass or more, while preferably 20% by mass or less, more preferably 15% by mass or less, still more preferably 10% by mass or less, particularly preferably 8% by mass or less, relative to the negative electrode active material. The binder at a proportion relative to the negative electrode active material higher than the above range may lead to an increased proportion of the binder which fails to contribute to the battery capacity, causing a low battery capacity. The binder at a proportion lower than the above range may cause lowered strength of the negative electrode.

In particular, in the case of using a rubbery polymer typified by SBR as a main component, the proportion of the binder is usually 0.1% by mass or more, preferably 0.5% by mass or more, more preferably 0.6% by mass or more, while usually 5% by mass or less, preferably 3% by mass or less, more preferably 2% by mass or less, relative to the negative electrode active material. In the case of using a fluoropolymer typified by polyvinylidene fluoride as a main component, the proportion of the binder is usually 1% by mass or more, preferably 2% by mass or more, more preferably 3% by mass or more, while usually 15% by mass or less, preferably 10% by mass or less, more preferably 8% by mass or less, relative to the negative electrode active material.

Examples of the thickening agent include the same thickening agents as those mentioned for the positive electrode. The proportion of the thickening agent is usually 0.1% by mass or higher, preferably 0.5% by mass or higher, still more preferably 0.6% by mass or higher, while usually 5% by mass or lower, preferably 3% by mass or lower, still more preferably 2% by mass or lower, relative to the negative electrode active material. The thickening agent at a proportion relative to the negative electrode active material lower than the above range may cause significantly poor easiness of application. The thickening agent at a proportion higher than the above range may cause a small proportion of the negative electrode active material in the negative electrode active material layer, resulting in a low capacity of the battery and high resistance between the negative electrode active materials.

Examples of the conductive material of the negative electrode include metal materials such as copper and nickel; and carbon materials such as graphite and carbon black.

The solvent for forming slurry may be any solvent that can dissolve or disperse the negative electrode active material and the binder, as well as a thickening agent and a conductive material used as appropriate. The solvent may be either an aqueous solvent or an organic solvent.

Examples of the aqueous solvent include water and alcohols. Examples of the organic solvent include N-methylpyrrolidone (NMP), dimethyl formamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phospharamide, dimethyl sulfoxide, benzene, xylene, quinoline, pyridine, methyl naphthalene, and hexane.

Examples of the material of the current collector for a negative electrode include copper, nickel, and stainless steel. In order to easily process the material into a film and to minimize the cost, copper foil is preferred.

The current collector usually has a thickness of 1 μm or greater, preferably 5 μm or greater, while usually 100 μm or smaller, preferably 50 μm or smaller. Too thick a negative electrode current collector may cause an excessive reduction in capacity of the whole battery, while too thin a current collector may be difficult to handle.

The negative electrode may be produced by a usual method. An example of the production method is a method in which the negative electrode material is mixed with the aforementioned binder, thickening agent, conductive material, solvent, and other components to form a slurry-like mixture, and then this mixture is applied to a current collector, dried, and pressed so as to be densified. In the case of using an alloyed material, a thin film layer containing the above negative electrode active material (negative electrode active material layer) may be produced by vapor deposition, sputtering, plating, or the like.

The electrode formed from the negative electrode active material may have any structure. The negative electrode active material existing on the current collector preferably has a density of 1 g·cm$^{-3}$ or higher, more preferably 1.2 g·cm$^3$ or higher, particularly preferably 1.3 g·cm$^3$ or higher, while preferably 2.2 g·cm$^{-3}$ or lower, more preferably 2.1 g cm$^3$ or lower, still more preferably 2.0 g·cm$^{-3}$ or lower, particularly preferably 1.9 g·cm$^3$ or lower. The negative electrode active material existing on the current collector having a density higher than the above range may cause destruction of the negative electrode active material particles, resulting in a high initial irreversible capacity and poor high-current-density charge and discharge characteristics due to reduction in permeability of the electrolyte solution toward the vicinity of the interface between the current collector and the negative electrode active material. The negative electrode active material having a density below the above range may cause poor conductivity between the negative electrode active materials, high battery resistance, and a low capacity per unit volume.

The thickness of the negative electrode plate is a design matter in accordance with the positive electrode plate to be used, and may be any value. The thickness of the mixture layer excluding the thickness of the base metal foil is usually 15 μm or greater, preferably 20 μm or greater, more preferably 30 μm or greater, while usually 300 μm or smaller, preferably 280 μm or smaller, more preferably 250 μm or smaller.

To a surface of the negative electrode plate may be attached a substance having a composition different from the negative electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

The lithium ion secondary battery of the invention preferably further includes a separator.

The separator may be formed from any known material and may have any known shape as long as the resulting separator is stable to the electrolyte solution and is excellent in a liquid-retaining ability. The separator is preferably in the form of a porous sheet or a nonwoven fabric which is formed from a material stable to the electrolyte solution of the invention, such as resin, glass fiber, or inorganic matter, and which has an excellent liquid-retaining ability.

Examples of the material of a resin or glass-fiber separator include polyolefins such as polyethylene and polypropylene, aromatic polyamide, polytetrafluoroethylene, polyether sulfone, and glass filters. These materials may be used alone or in any combination of two or more at any ratio, for example, in the form of a polypropylene/polyethylene bilayer film or a polypropylene/polyethylene/polypropylene trilayer film. In order to achieve good permeability of the electrolyte solution and a good shut-down effect, the separator is preferably a porous sheet or a nonwoven fabric formed from a polyolefin such as polyethylene or polypropylene.

The separator may have any thickness, and the thickness is usually 1 μm or greater, preferably 5 μm or greater, more preferably 8 μm or greater, while usually 50 μm or smaller, preferably 40 μm or smaller, more preferably 30 μm or smaller. The separator thinner than the above range may have poor insulation and mechanical strength. The separator thicker than the above range may cause not only poor battery performance such as poor rate characteristics but also a low energy density of the whole electrolyte battery.

The separator which is a porous one such as a porous sheet or a nonwoven fabric may have any porosity. The porosity is usually 20% or higher, preferably 35% or higher, more preferably 45% or higher, while usually 90% or lower, preferably 85% or lower, more preferably 75% or lower. The separator having a porosity lower than the above range tends to have high film resistance, causing poor rate characteristics. The separator having a porosity higher than the above range tends to have low mechanical strength, causing poor insulation.

The separator may also have any average pore size. The average pore size is usually 0.5 μm or smaller, preferably 0.2 μm or smaller, while usually 0.05 μm or larger. The separator having an average pore size larger than the above range may easily cause short circuits. The separator having an average pore size smaller than the above range may have high film resistance, causing poor rate characteristics.

Examples of the inorganic matter include oxides such as alumina and silicon dioxide, nitrides such as aluminum nitride and silicon nitride, and sulfates such as barium sulfate and calcium sulfate, each in the form of particles or fibers.

The separator is in the form of a thin film such as a nonwoven fabric, a woven fabric, or a microporous film. The thin film favorably has a pore size of 0.01 to 1 μm and a thickness of 5 to 50 μm. Instead of the above separate thin film, the separator may have a structure in which a composite porous layer containing particles of the above inorganic matter is disposed on a surface of one or each of the positive and negative electrodes using a resin binder. For example, alumina particles having a 90% particle size of smaller than 1 μm may be applied to the respective surfaces of the positive electrode with fluororesin used as a binder to form a porous layer.

<Battery Design>

The electrode group may be either a laminate structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group proportion) is usually 40% or higher, preferably 50% or higher, while usually 90% or lower, preferably 80% or lower.

The electrode group proportion lower than the above range may cause a low battery capacity. The electrode group proportion higher than the above range may cause small void space in the battery. Thus, if the battery temperature rises to high temperature and thereby the components swell and the liquid fraction of the electrolyte solution exhibits high vapor pressure to raise the internal pressure, the battery characteristics such as charge and discharge repeatability and high-temperature storageability may be impaired and a gas-releasing valve for releasing the internal pressure toward the outside may be actuated.

The current collecting structure may be any structure. In order to more effectively improve the high-current-density charge and discharge performance by the electrolyte solution of the invention, the current collecting structure is preferably a structure which reduces the resistances at wiring portions and jointing portions. Such reduction in internal resistance can particularly favorably lead to the effects achieved with the electrolyte solution of the invention.

In an electrode group having the laminate structure, the metal core portions of the respective electrode layers are preferably bundled and welded to a terminal. If an electrode has a large area, the internal resistance is high. Thus, multiple terminals may preferably be disposed in the electrode so as to reduce the resistance. In an electrode group having the wound structure, multiple lead structures may be disposed on each of the positive electrode and the negative electrode and bundled to a terminal. This can reduce the internal resistance.

The external case may be made of any material that is stable to an electrolyte solution to be used. Specific examples thereof include metals such as nickel-plated steel plates, stainless steel, aluminum and aluminum alloys, and magnesium alloys, and a layered film (laminate film) of resin and aluminum foil. In order to reduce the weight, a metal such as aluminum or an aluminum alloy or a laminate film is favorably used.

An external case made of metal may have a sealed-up structure formed by welding the metal by laser welding, resistance welding, or ultrasonic welding, or a caulking structure using the metal with a resin gasket in between. An external case made of a laminate film may have a sealed-up structure formed by hot-melting resin layers. In order to improve the sealability, a resin which is different from the resin of the laminate film may be disposed between the resin layers. Especially, in the case of forming a sealed-up structure by hot-melting the resin layers with current collecting terminals in between, metal and resin are to be bonded. Thus, the resin to be disposed between the resin layers is favorably a resin having a polar group or a modified resin having a polar group introduced therein.

The lithium ion secondary battery of the invention may have any shape, such as a cylindrical shape, a square shape, a laminate shape, a coin shape, or a large-size shape. The shapes and the structures of the positive electrode, the negative electrode, and the separator may be changed in accordance with the shape of the battery.

A module including the lithium ion secondary battery of the invention is also one aspect of the invention.

In a preferred embodiment, the lithium ion secondary battery includes a positive electrode, a negative electrode, and the aforementioned electrolyte solution, the positive electrode including a positive electrode current collector and a positive electrode active material layer containing a positive electrode active material, the positive electrode active material containing Mn. The lithium ion secondary battery including a positive electrode active material layer that contains a positive electrode active material containing Mn can have much better high-temperature storage characteristics.

In order to provide a high-power lithium ion secondary battery having a high energy density, preferred as the positive electrode active material containing Mn are $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$.

The amount of the positive electrode active material in the positive electrode active material layer is preferably 80% by mass or more, more preferably 82% by mass or more, particularly preferably 84% by mass or more. The upper limit of the amount thereof is preferably 99% by mass or less, more preferably 98% by mass or less. Too small an amount of the positive electrode active material in the positive electrode active material layer may lead to an insufficient electric capacity. In contrast, too large an amount thereof may lead to insufficient strength of the positive electrode.

The positive electrode active material layer may further contain a conductive material, a thickening agent, and a binder.

The binder may be any material that is safe against a solvent to be used in production of electrodes and the electrolyte solution. Examples thereof include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, NBR (acrylonitrile-butadiene rubber), fluoroelastomer, ethylene-propylene rubber, styrene-butadiene-styrene block copolymers and hydrogenated products thereof, EPDM (ethylene-propylene-diene terpolymers), styrene-ethylene-butadiene-ethylene copolymers, styrene-isoprene-styrene block copolymers and hydrogenated products thereof, syndiotactic-1,2-polybutadiene, polyvinyl acetate, ethylene-vinyl acetate copolymers, propylene-α-olefin copolymers, fluorinated polyvinylidene fluoride, tetrafluoroethylene-ethylene copolymers, and polymer compositions having ion conductivity of alkali metal ions (especially, lithium ions). These substances may be used alone or in any combination of two or more at any ratio.

The amount of the binder, which is expressed as the proportion of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, and amorphous carbon, including needle coke. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, conductive material in an amount more than the above range may cause a low battery capacity.

In order to further improve the high-temperature storage characteristics, the positive electrode current collector is preferably formed from a valve metal or an alloy thereof. Examples of the valve metal include aluminum, titanium, tantalum, and chromium. The positive electrode current collector is more preferably formed from aluminum or an alloy of aluminum.

In order to further improve the high-temperature storage characteristics of the lithium ion secondary battery, a portion in contact with the electrolyte solution among portions electrically coupled with the positive electrode current collector is also preferably formed from a valve metal or an alloy thereof. In particular, the external case of the battery and a portion that is electrically coupled with the positive electrode current collector and is in contact with the non-aqueous electrolyte solution among components accommodated in the external case of the battery, such as leads and a safety valve, are preferably formed from a valve metal or an alloy thereof. Stainless steel coated with a valve metal or an alloy thereof may also be used.

The positive electrode may be produced by the aforementioned method. An example of the production method is a method in which the positive electrode active material is mixed with the aforementioned binder, thickening agent, conductive material, solvent, and other components to form a slurry-like positive electrode mixture, and then this mixture is applied to a positive electrode current collector, dried, and pressed so as to be densified.

The structure of the negative electrode is as described above.

The electrolyte solution of the invention is useful as an electrolyte solution for large-size lithium ion secondary batteries for hybrid vehicles or distributed generation.

EXAMPLES

The invention is described with reference to examples, but the examples are not intended to limit the invention.

Examples and Comparative Examples (Synthesis of EMImBOB)

To a reaction vessel charged with dehydrated dichloromethane and 1-ethyl-3-methyl imidazolium chloride was added lithium bis(oxalato)borate, whereby the components were reacted. The resulting mixture was concentrated under reduced pressure and purified by silica gel column chromatography to provide a compound (EMImBOB) represented by the following formula.

[Chem. 78]

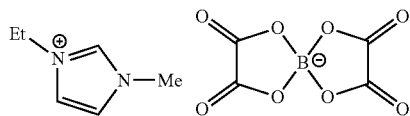

(Synthesis of BMImBOB)

A compound (BMImBOB) represented by the following formula was synthesized in the same manner as described above, except that the starting material was changed from 1-ethyl-3-methyl imidazolium chloride to 1-butyl-3-methyl imidazolium chloride.

[Chem. 79]

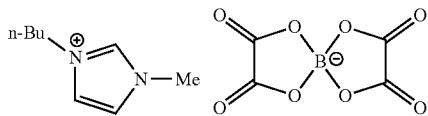

(Preparation of Electrolyte Solution)

Ethylene carbonate (EC), ethyl methyl carbonate (EMC), and dimethyl carbonate (DMC) were mixed at a volume ratio of 30/30/40. To the mixture were added ion sources such that the ions in the resulting electrolyte solution had the respective concentrations according to Table 1, whereby a non-aqueous electrolyte solution was obtained. Specific amounts of the materials were as follows.

In Example 1, $4.0 \times 10^{-4}$ M of the compound (I) and 1.0 M of $LiPF_6$ were added.

In Example 2, $4.0 \times 10^{-3}$ M of the compound (I) and 1.0 M of $LiPF_6$ were added.

In Example 3, $2.0 \times 10^{-2}$ M of the compound (I) and 1.0 M of $LiPF_6$ were added.

In Example 4, $4.0 \times 10^{-2}$ M of the compound (I) and 1.0 M of $LiPF_6$ were added.

In Example 5, $8.0 \times 10^{-2}$ M of the compound (I) and 1.0 M of $LiPF_6$ were added.

In Example 6, $2.0 \times 10^{-1}$ M of the compound (I) and 1.0 M of $LiPF_6$ were added.

In Example 7, $4.0 \times 10^{-1}$ M of the compound (I) and 1.0 M of $LiPF_6$ were added.

In Example 8, $4.8 \times 10^{-1}$ M of the compound (I) and 1.0 M of $LiPF_6$ were added.

In Example 9, $2.0 \times 10^{-2}$ M of the compound (II) and 1.0 M of $LiPF_6$ were added.

In Examples 12 and 13, $2.0 \times 10^{-2}$ M of the compound (I) and 1.0 M of $LiPF_6$ were added.

In Examples 14 to 20, $2.0 \times 10^{-2}$ M of the compound (II) and 1.0 M of $LiPF_6$ were added.

The abbreviations in Table 1 are as follows. BOB:

[Chem. 80]

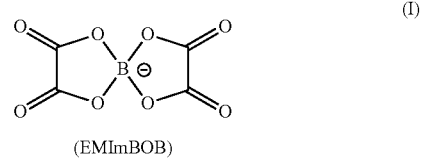

[Chem. 81]

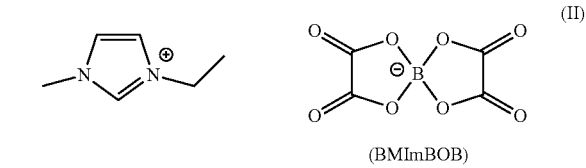

[Chem. 82]

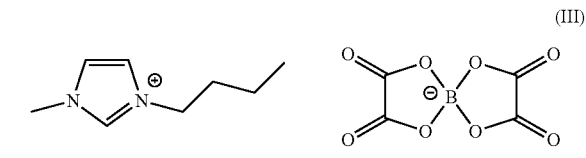

[Chem. 83]

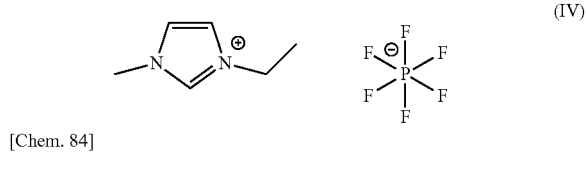

[Chem. 84]

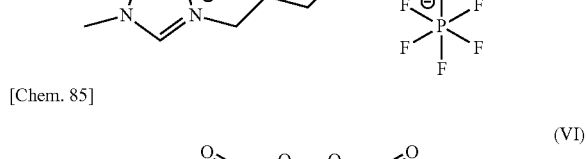

[Chem. 85]

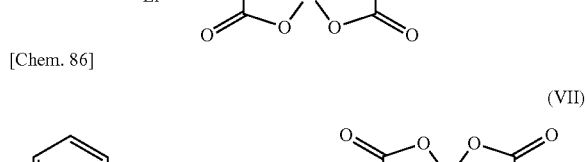

[Chem. 86]

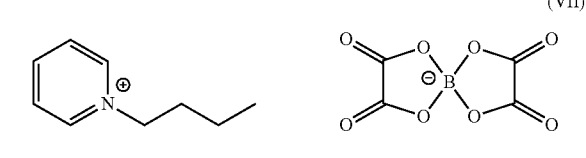

-continued

 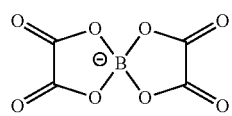

[Chem. 87]

VC: vinylene carbonate
VEC: vinyl ethylene carbonate
FEC: fluoroethylene carbonate
DFEC: difluoroethylene carbonate
(Production of Aluminum Laminate-Type Lithium Ion Secondary Battery)
[Production of Positive Electrode]

First, 93% by mass of $Li(Ni_{1/3}Mn_{1/3}Co_{1/3})O_2$ (NMC) serving as a positive electrode active material, 3% by mass of acetylene black serving as a conductive material, and 4% by mass of polyvinylidene fluoride (PVdF) serving as a binding agent were mixed in a N-methylpyrrolidone solvent to form slurry. The resulting slurry was applied to one surface of 15-µm-thick aluminum foil with a conductive aid applied thereto in advance, and dried. The workpiece was then roll-pressed using a press and cut to provide a piece including an active material layer having a width of 50 mm and a length of 30 mm and an uncoated portion having a width of 5 mm and a length of 9 mm. This piece was used as a positive electrode.
[Production of Negative Electrode]

First, 98 parts by mass of a carbonaceous material (graphite) was mixed with 1 part by mass of an aqueous dispersion of sodium carboxymethyl cellulose (concentration of sodium carboxymethyl cellulose: 1% by mass) and 1 part by mass of an aqueous dispersion of styrene-butadiene rubber (concentration of styrene-butadiene rubber: 50% by mass) respectively serving as a thickening agent and a binder. The components were mixed using a disperser to form slurry. The resulting slurry was applied to 10-µm-thick copper foil and dried. The workpiece was rolled using a press and cut to provide a piece including an active material layer having a width of 52 mm and a length of 32 mm and an uncoated portion having a width of 5 mm and a length of 9 mm. This piece was used as a negative electrode.
[Production of Aluminum Laminate Cell]

The above positive electrode and negative electrode were placed to face each other with a 20-µm-thick porous polyethylene film (separator) in between. The non-aqueous electrolyte solution prepared above was filled thereinto and the non-aqueous electrolyte solution was made to sufficiently permeate into the components such as the separator. The workpiece was then sealed, pre-charged, and aged, whereby a lithium ion secondary battery was produced.
(Determination of Battery Characteristics)
[High-Temperature Cycle Characterisitc Test]

The lithium ion secondary battery produced above in a state of being sandwiched and pressed between plates was subjected to constant current/constant voltage charge (hereinafter, referred to as CC/CV charge) (0.1 C cut off) to 4.3 V at a current corresponding to 1 C and at 60° C., and then discharged to 3 V at a constant current of 1 C. This was counted as one cycle, and the discharge capacity at the third cycle was used to determine the initial discharge capacity. The cycles were again performed, and the discharge capacity after the 200th cycle was defined as the capacity after cycles. The ratio of the discharge capacity after the 200th cycle to the initial discharge capacity was determined. This value was defined as the cycle capacity retention (%).

(Discharge capacity after the 200th cycle)÷(Initial discharge capacity)×100=Capacity retention (%)

The results are shown in Table 1.
[Evaluation of IV Resistance]

The battery after evaluation of initial discharge capacity was charged at a constant current of 1 C and at 25° C. so as to have a capacity that is half the initial discharge capacity. The battery was then discharged at 2.0 C, and the voltage at the 10th second was measured. The resistance was calculated from the voltage drop during discharge, which was defined as the IV resistance. The results are shown in Table 1.

TABLE 1

| | Ion in electrolyte solution | | | | Ion source added | | Other additive | | Cycle capacity retention (%) | IV resistance (Ω) |
|---|---|---|---|---|---|---|---|---|---|---|
| | Imidazolium (M) | BOB (M) | $PF_6^-$ (M) | $Cl^-$ (ppm) | | | Kind | Amount (mass %) | | |
| Example 1 | $4.0 \times 10^{-4}$ | $4.0 \times 10^{-4}$ | 1.0 | 0.050 | (I) | $LiPF_6$ | | | 87 | 2.3 |
| Example 2 | $4.0 \times 10^{-3}$ | $4.0 \times 10^{-3}$ | 1.0 | 0.50 | (I) | $LiPP_6$ | | | 88 | 2.0 |
| Example 3 | $2.0 \times 10^{-2}$ | $2.0 \times 10^{-2}$ | 1.0 | 2.5 | (I) | $LiPF_6$ | | | 91 | 1.9 |
| Example 4 | $4.0 \times 10^{-2}$ | $4.0 \times 10^{-2}$ | 1.0 | 5.0 | (I) | $LiPF_6$ | | | 93 | 1.8 |
| Example 5 | $8.0 \times 10^{-2}$ | $8.0 \times 10^{-2}$ | 1.0 | 10 | (I) | $LiPF_6$ | | | 92 | 2.0 |
| Example 6 | $2.0 \times 10^{-1}$ | $2.0 \times 10^{-1}$ | 1.0 | 25 | (I) | $LiPF_6$ | | | 91 | 2.2 |
| Example 7 | $4.0 \times 10^{-1}$ | $4.0 \times 10^{-1}$ | 1.0 | 50 | (I) | $LiPF_6$ | | | 90 | 2.4 |
| Example 8 | $4.8 \times 10^{-1}$ | $4.8 \times 10^{-1}$ | 1.0 | 60 | (I) | $LiPF_6$ | | | 84 | 3.7 |
| Example 9 | $2.0 \times 10^{-2}$ | $2.0 \times 10^{-2}$ | 1.0 | 2.5 | (II) | $LiPF_6$ | | | 91 | 1.7 |
| Example 10 | $2.0 \times 10^{-2}$ | $2.0 \times 10^{-2}$ | 1.0 | 2.5 | (III) (V) | $LiPF_6$ | | | 88 | 2.3 |
| Example 11 | $2.0 \times 10^{-2}$ | $2.0 \times 10^{-2}$ | 1.0 | 2.5 | (IV) (V) | $LiPF_6$ | | | 86 | 2.5 |
| Example 12 | $2.0 \times 10^{-2}$ | $2.0 \times 10^{-2}$ | 1.0 | 500 | (I) | $LiPF_6$ | | | 83 | 3.4 |
| Example 13 | $2.0 \times 10^{-2}$ | $2.0 \times 10^{-2}$ | 1.0 | 0.0050 | (I) | $LiPF_6$ | | | 85 | 2.4 |
| Example 14 | $2.0 \times 10^{-2}$ | $2.0 \times 10^{-2}$ | 1.0 | 2.5 | (II) | $LiPF_6$ | Succinio anhydride | 1.0 | 91 | 2.1 |
| Example 15 | $2.0 \times 10^{-2}$ | $2.0 \times 10^{-2}$ | 1.0 | 2.5 | (II) | $LiPF_6$ | Maleic anhydride | 1.0 | 93 | 3.8 |
| Example 16 | $2.0 \times 10^{-2}$ | $2.0 \times 10^{-2}$ | 1.0 | 2.5 | (II) | $LiPF_6$ | VC | 1.0 | 90 | 3.7 |
| Example 17 | $2.0 \times 10^{-2}$ | $2.0 \times 10^{-2}$ | 1.0 | 2.5 | (II) | $LiPF_6$ | Adiponitrile | 1.0 | 88 | 4.1 |
| Example 18 | $2.0 \times 10^{-2}$ | $2.0 \times 10^{-2}$ | 1.0 | 2.5 | (II) | $LiPF_6$ | FEC | 1.0 | 93 | 2.7 |
| Example 19 | $2.0 \times 10^{-2}$ | $2.0 \times 10^{-2}$ | 1.0 | 2.5 | (II) | $LiPF_6$ | VEC | 1.0 | 90 | 3.1 |

TABLE 1-continued

| | Ion in electrolyte solution | | | | | Other additive | | Cycle capacity | IV |
|---|---|---|---|---|---|---|---|---|---|
| | Imidazolium (M) | BOB (M) | PF$_6^-$ (M) | Cl$^-$ (ppm) | Ion source added | Kind | Amount (mass %) | retention (%) | resistance (Ω) |
| Example 20 | 2.0 × 10$^{-2}$ | 2.0 × 10$^{-2}$ | 1.0 | 2.5 | (II) LiPF$_6$ | DFEC | 1.0 | 92 | 3.6 |
| Comparative Example 1 | — | 2.0 × 10$^{-2}$ | 1.0 | 2.5 | (VI) LiPF$_6$ | | | 66 | 4.2 |
| Comparative Example 2 | — | 2.0 × 10$^{-2}$ | 1.0 | 2.5 | (VII) LiPF$_6$ | | | 41 | 5.4 |
| Comparative Example 3 | — | 2.0 × 10$^{-2}$ | 1.0 | 2.5 | (V) LiPF$_6$ | | | 83 | 4.1 |
| Comparative Example 4 | 2.0 × 10$^{-2}$ | — | 1.0 | 2.5 | (IV) LiPF$_6$ | | | 69 | 3.8 |
| Comparative Example 5 | — | — | 1.0 | — | LiPF$_6$ | | | 66 | 5.1 |

The invention claimed is:

1. An electrolyte solution for a lithium ion secondary battery, comprising a compound (1) represented by the following formula (1):

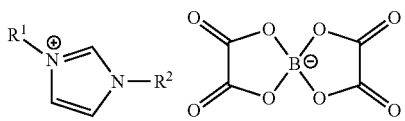

wherein R$^1$ and R$^2$ are each independently a C1-C4 alkyl group optionally containing an ether bond, and
wherein chloride ion is present at a concentration of 1.0×10$^{-6}$ to 1.0×10$^3$ ppm, and
the compound (1) is present in an amount of 4.0×10$^{-6}$ to 3.2×10$^{-1}$ mol/L relative to the electrolyte solution.

2. The electrolyte solution for a lithium ion secondary battery according to claim 1,
wherein at least one selected from R$^1$ and R$^2$ in the formula (1) is a methyl group.

3. The electrolyte solution for a lithium ion secondary battery according to claim 1,
wherein the compound (1) is at least one selected from the group consisting of a compound (1-a) represented by the following formula (1-a):

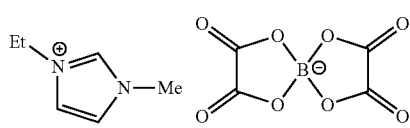 [SMILES: CC[n+]1ccn(C)c1 ; O=C1O[B-]2(OC1=O)OC(=O)C(=O)O2]

and a compound (1-b) represented by the following formula (1-b):

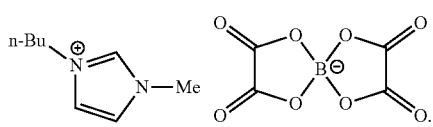

4. An electrolyte solution for a lithium ion secondary battery, comprising an imidazolium cation (1-1) represented by the following formula (1-1), a bis(oxalato)borate anion, and a hexafluorophosphate anion, the formula (1-1) being

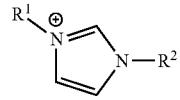

wherein R$^1$ and R$^2$ are each independently a C1-C4 alkyl group optionally containing an ether bond, and
wherein chloride ion is present at a concentration of 1.0×10$^{-6}$ to 1.0×10$^3$ ppm,
the imidazolium cation (1-1) is present at a concentration of 1.0×10$^{-5}$ to 3.0×10$^{-1}$ mol/L, and
the bis(oxalato)borate anion is present at a concentration of 1.0×10$^{-5}$ to 3.0×10$^{-1}$ mol/L.

5. The electrolyte solution for a lithium ion secondary battery according to claim 4,
wherein at least one selected from R$^1$ and R$^2$ in the formula (1-1) is a methyl group.

6. The electrolyte solution for a lithium ion secondary battery according to claim 4,
wherein the imidazolium cation (1-1) is at least one selected from the group consisting of an imidazolium cation (1-1a) represented by

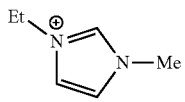

and an imidazolium cation (1-1b) represented by

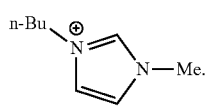

7. The electrolyte solution for a lithium ion secondary battery according to claim 4,
wherein the hexafluorophosphate anion is present at a concentration of 0.01 to 1.5 mol/L.

8. A lithium ion secondary battery comprising the electrolyte solution according to claim 1.

9. A module comprising the lithium ion secondary battery according to claim 8.

10. A lithium ion secondary battery comprising the electrolyte solution according to claim 4.

11. A module comprising the lithium ion secondary battery according to claim 10.

* * * * *